United States Patent [19]
Caput et al.

[11] Patent Number: 5,382,518
[45] Date of Patent: Jan. 17, 1995

[54] URATE OXIDASE ACTIVITY PROTEIN, RECOMBINANT GENE CODING THEREFOR, EXPRESSION VECTOR, MICRO-ORGANISMS AND TRANSFORMED CELLS

[75] Inventors: Daniel Caput, Toulouse; Pascual Ferrara, Villefranche de Lauragais; Jean-Claude Guillemot, Toulouse; Mourad Kaghad, Ramonville St. Agne; Richard Legoux, Caraman; Gérard Loison, Toulouse; Elisabeth Larbre, Avignon; Johannes Lupker, Castanet-Tolosan; Pascal Leplatois, Cuq Toulza; Marc Salome, Castanet-Tolosan; Patrick Laurent, Pechbusque, all of France

[73] Assignee: Sanofi, Paris, France

[21] Appl. No.: 920,519

[22] PCT Filed: Jul. 13, 1990

[86] PCT No.: PCT/FR90/00532
§ 371 Date: Apr. 25, 1991
§ 102(e) Date: Apr. 25, 1991

[87] PCT Pub. No.: WO91/00909
PCT Pub. Date: Jan. 24, 1991

Related U.S. Application Data

[63] Continuation of Ser. No. 659,408, Apr. 25, 1991, abandoned.

[30] Foreign Application Priority Data

Dec. 29, 1989 [FR] France .................. 89 17466
Feb. 6, 1990 [FR] France .................. 90 01368
Jul. 13, 1990 [FR] France .................. 89 09550

[51] Int. Cl.[6] ................ C12N 9/00; C12P 21/00
[52] U.S. Cl. ................... 435/191; 435/69.1
[58] Field of Search ............ 435/69.1, 191, 10, 12

[56] References Cited

U.S. PATENT DOCUMENTS 3,810,820 5/1974 Laboureur et al. .......... 435/191
4,431,739 2/1984 Riggs ....................... 435/69.1

OTHER PUBLICATIONS

Reddy et al. Proc Natl. Acad. Sci USA (1988) vol. 85 pp. 9081-9085.
Nielsen et al. Proc Natl. Acad Sci USA (1983) vol. 80 pp. 5198-5202.
Mansson-Rahemtulla et al Biochemistry vol. 27 pp. 233-239 issued Jan. 12, 1988.
Nakagawa et al Biochem Biophy. Res. Comm vol. 127(1) pp. 8-14 Feb. 28, 1985.
Janson Trends in Biotechnology vol. 2(2) 31-38 1984.
Berton et al Jour. Biol Chem vol. 264(10) pp. 5564-5568 issued Apr. 5, 1989.

Primary Examiner—Robert A. Wax
Assistant Examiner—David Schmickel
Attorney, Agent, or Firm—Foley & Lardner

[57] ABSTRACT

The invention concerns a new urate oxidase activity protein which has the following sequence:

| | | | | | | | | |
|---|---|---|---|---|---|---|---|---|
| | Ser | Ala | Val | Lys | Ala | Ala | Arg | Tyr | Gly |
| Lys | Asp | Asn | Val | Arg | Val | Tyr | Lys | Val | His |
| Lys | Asp | Glu | Lys | Thr | Gly | Val | Gln | Thr | Val |
| Tyr | Glu | Met | Thr | Val | Cys | Val | Leu | Leu | Glu |
| Gly | Glu | Ile | Glu | Thr | Ser | Tyr | Thr | Lys | Ala |
| Asp | Asn | Ser | Val | Ile | Val | Ala | Thr | Asp | Ser |
| Ile | Lys | Asn | Thr | Ile | Tyr | Ile | Thr | Ala | Lys |
| Gln | Asn | Pro | Val | Thr | Pro | Pro | Glu | Leu | Phe |
| Gly | Ser | Ile | Leu | Gly | Thr | His | Phe | Ile | Glu |
| Lys | Tyr | Asn | His | Ile | His | Ala | Ala | His | Val |
| Asn | Ile | Val | Cys | His | Arg | Trp | Thr | Arg | Met |
| Asp | Ile | Asp | Gly | Lys | Pro | His | Pro | His | Ser |
| Phe | Ile | Arg | Asp | Ser | Glu | Glu | Lys | Arg | Asn |
| Val | Gln | Val | Asp | Val | Val | Glu | Gly | Lys | Gly |
| Ile | Asp | Ile | Lys | Ser | Ser | Leu | Ser | Gly | Leu |
| Thr | Val | Leu | Lys | Ser | Thr | Asn | Ser | Gln | Phe |
| Trp | Gly | Phe | Leu | Arg | Asp | Glu | Tyr | Thr | Thr |
| Leu | Lys | Glu | Thr | Trp | Asp | Arg | Ile | Leu | Ser |
| Thr | Asp | Val | Asp | Ala | Thr | Trp | Gln | Trp | Lys |
| Asn | Phe | Ser | Gly | Leu | Gln | Glu | Val | Arg | Ser |
| His | Val | Pro | Lys | Phe | Asp | Ala | Thr | Trp | Ala |
| Thr | Ala | Arg | Glu | Val | Thr | Leu | Lys | Thr | Phe |
| Ala | Glu | Asp | Asn | Ser | Ala | Ser | Val | Gln | Ala |
| Thr | Met | Tyr | Lys | Met | Ala | Glu | Gln | Ile | Leu |
| Ala | Arg | Gln | Gln | Leu | Ile | Glu | Thr | Val | Glu |
| Tyr | Ser | Leu | Pro | Asn | Lys | His | Tyr | Phe | Glu |
| Ile | Asp | Leu | Ser | Trp | His | Lys | Gly | Leu | Gln |
| Asn | Thr | Gly | Lys | Asn | Ala | Glu | Val | Phe | Ala |

(Abstract continued on next page.)

| -continued | | | | | | | | | |
|---|---|---|---|---|---|---|---|---|---|
| Pro | Gln | Ser | Asp | Pro | Asn | Gly | Leu | Ile | Lys |
| Cys | Thr | Val | Gly | Arg | Ser | Ser | Leu | Lys | Ser |
| Lys | Leu | | | | | | | | | optionally preceeded by a methionine, or in that it may present a degree of substantial homology with this sequence.

The invention is also aimed at medicines containing this protein as well as the genetic engineering implements to obtain it.

9 Claims, 15 Drawing Sheets

ELUTION PROFILE BY MEASUREMENT OF THE OPTICAL DENSITY AT 218 nm
OF THE PRODUCT OF TRYPTIC DIGESTION OF URATE OXIDASE

ELUTION PROFILE BY MEASUREMENT OF THE OPTICAL DENSITY AT 218 nm OF THE PRODUCT OF DIGESTION OF URATE OXIDASE WITH PROTEASE V8

FIG. 3

```
   1 AAACCCTCACTGCCTCTCTCATTCCTTCCG GTGCCCCCGATCCTCAATCCAACTTGTACA   60
  61 TACTTCTCCAACTCTCTGCTATATCCTTC   ATATTCCCATACTACAAGATGTCCGCAGTA  120
 121 AAAGCAGCCCGCTACGGCAAGGACAATGTC  CGCGGTCTACAAGGTTCACAAGGACGAGAAG  180
 181 ACCGGTGTCCAGACGGTGTACGAGATGACC  GTCTGTGTGCTTCTGGAGGGTGAGATTGAG  240
 241 ACCTTCTTACACCAAGGCCGACAACAGCGTC ATTGTCGCAACGACTCCATTAAGAACACC   300
 301 ATTTACATCACCGCCAAGCAGAACCCCGTT  ACTCCTCCCGAGCTGTTCGCTCCATCCTG   360
 361 GGCACACACTTCATTGAGAAGTACAACCAC  ATCCATGCCGCTCACGTCAACATTGTCTGC  420
 421 CACCGCTGGACCCGGATGGACATTGACGGC  AAGCCACACCCTCACTCCTTCATCCGCGAC  480
            A*
 481 AGCGAGGAGAAGCGGGAATGTGCAGGTGGAC GTGGTCGAGGGCAAGGGCATCGATATCAAG  540
 541 TCGTCTCTCGTCCGGCCTCAGTTCCTGAAG  AGCACCAACTCGCAGTTCCTGGGGCTTCCTG  600
 601 CGTGACGAGTACACCAGTTAAGGAGACC    TGGGACCGTATCCTGAGCACCGACGTCGAT  660
 661 GCCACTTGGCAGTGGAAGAATTTCAGTGGA  CTCCAGGAGGTCCGCTCGCACGTGCCTAAG  720
 721 TTCGATGCTACTGGGCCACTGCTCGCGAG   GTCACTCTGAAGACTTTTGCTGAAGATAAC  780
 781 AGTGCCAGCGTGCAGCCACTATGTACAAG   ATGGCAGAGAGCAAATCCTGGCGCGCCAGCAG 840
 841 CTGATCGAGACTGTCGAGTACTCGTTGCCT  AACAAGCACTATTTCGAAATCGACCTGAGC  900
    G*
 901 TGGCACAAGGGCCTCCAAAACACCGGCAAG  AACGCCGAGTCTTCGCTCCTCAGTCGGAC   960
 961 CCCAACGGTCTGATCAAGTGTACCGTCGGC  CGGTCCTCTGAAGTCTAAATTGTAAACC  1020
1021 AACATGATTCTCACGTTCCGGAGTTTCCAA  GGCAAACTGTATATAGTCTGGGATAGGGTA 1080
1081 TAGCATTCATTCACTTGTTTTACTTCCA    AAAAAAAAAA....              
```

NUCLEOTIDE SEQUENCE OF CLONE 9C AND OF PART OF CLONE 9A

 : START OF CLONE 9A

FIG. 4A

```
109 ATGTCCGCAGTAAAAGCAGCCCGCTACGGC AAGGACAATGTCCGCGTCTACAAGGTTCAC 168
  1 MetSerAlaValLysAlaAlaArgTyrGly LysAspAsnValArgValTyrLysValHis  20

169 AAGGACGAGAAGACCGGTGTCCAGACGGTG TACGAGATGACCGTCTGTGTGCTTCTGGAG 228
 21 LysAspGluLysThrGlyValGlnThrVal TyrGluMetThrValCysValLeuLeuGlu  40

229 GGTGAGATTGAGACCTCTTACACCAAGGCC GACAACAGGTCATTGTGCAACCGACTCC   288
 41 GlyGluIleGluThrSerTyrThrLysAla AspAsnSerValIleValAlaAlaThrAspSer 60
                                                  V3
289 ATTAAGAACACCATTTACATCACCGCCAAG CAGAACCCCGTTACTCCTCCCGAGCTGTTC 348
 61 IleLysAsnThrIleTyrIleThrAlaLys GlnAsnProValThrProProGluLeuPhe  80
                                             T32/T33
349 GGCTCCATCCTGGGCACACACTTCATTGAG AAGTACAACCACATCCATGCCGCTCACGTC 408
 81 GlySerIleLeuGlyThrHisPheIleGlu LysTyrAsnHisIleHisAlaAlaHisVal 100

409 AACATTGTCTGCCACCGCTGGACCCGGATG GACATTGACGGCAAGCCACACCCTCACTCC 468
101 AsnIleValCysHisArgTrpThrArgMet AspIleAspGlyLysProHisProHisSer 120

469 TTCATCCGGACACAGGAGGAGAAGGGGAAT GTGCAGGTGGACGTGGTCAGGTAGTGAAGGGC 528
121 PheIleArgAspSerGluLysGlyAsn    ValGlnValAspValValGluValLysGly 140
                 V5/V6                                T17
529 ATCGATATCAAGTCGTCTGTCCGGCCTG ACCGTGCTGAAGAGCACCAACTCGCAGTTC 588
141 IleAspIleLysSerSerLeuSerGlyLeu ThrValLeuLysSerThrAsnSerGlnPhe 160
                                                           T31
589 TGGGGCTTCCTGCGTGACGAGTACACCACA CTTAAGGAGACCTGGGACCGTATCCTGAGC 648
161 TrpGlyPheLeuArgAspGluTyrThrThr LeuLysGluThrTrpAspArgIleLeuSer 180

649 ACCGACGTCGATGCCACTTGGCAGTGGAAG AATTTCAGTGGACTCCAGGAGGTCCGCTCG 708
181 ThrAspValAspAlaThrTrpGlnTrpLys AsnPheSerGlyLeuGlnGluValArgSer 200
                 T28                            T20
```

```
↑ FROM FIG. 4A                                                          FROM FIG. 4A ↑

709 CACGTGCTAAGTTCGATGCTACCTGGCC   ACTGCTCGCGAGGTCACTCTGAAGACTTTT 768
201 HisValProLysPheAspAlaThrTrpAla ThrAlaArgGluValThrLeuLysThrPhe 220
                    T23                         →

769 GCTGAAGATAACAGTGCCAGCGTGCAGGCC ACTATGTACAAGATGGCAGAGCAAATCCTG 828
221 AlaGluAspAsnSerAlaSerValGlnAla ThrMetTyrLysMetAlaGluGlnIleLeu 240
                    V2              →

829 GCGGCGCCAGCAGCTGATCGAGACTGTGAG TACTCGTTGCCTAACAAGCACTATTTCGAA 888
241 AlaArgGlnGlnLeuIleGluThrValGlu TyrSerLeuProAsnLysHisTyrPheGlu 260
                                                              T29/
                    V1

889 ATCGACCTGAGCTGGCACAAGGGCCTCCAA AACACCGGCAAGAACGCCGAGGTCTTCGCT 948
261 IleAspLeuSerTrpHisLysGlyLeuGln AsnThrGlyLysAsnAlaGluValPheAla 280
                        →
                    T27

949 CCTCAGTCGGACCCCAACGGTCTGATCAAG TGTACCGTGGGCCGGTCCTCTCTGAAGTCT 1008
281 ProGlnSerAspProAsnGlyLeuIleLys CysThrValGlyArgSerSerLeuLysSer 300

1009 AAATTGTAA
301  LysLeuEnd
```

DNA SEQUENCE OPENED BY ATG IN POSITION 109 IN FIGURE 3
AND POLYPEPTIDE CODED FOR.
THE SEQUENCED PEPTIDES OBTAINED BY HYDROLYSIS OF A. FLAVUS
URATE OXIDASE WITH TRYPSIN AND PROTEASE V8 ARE SHOWN BY
ARROWS OPPOSITE THE POLYPEPTIDE CODED FOR, ACCORDING TO

→ : TRYPTIC PEPTIDE
--- : PEPTIDE OBTAINED BY HYDROLYSIS WITH
      PROTEASE V8.

URATE OXIDASE ACTIVITY PROTEIN, RECOMBINANT GENE CODING THEREFOR, EXPRESSION VECTOR, MICRO-ORGANISMS AND TRANSFORMED CELLS

This application is a continuation of application Ser. No. 07/659,408, filed Apr. 25, 1991, now abandoned.

The invention relates to a novel protein possessing urate oxidase activity; the invention also concerns the drugs containing this protein as well as the genetic engineering tools for producing that protein and notably the recombinant gene coding for that protein, the expression vector carrying that gene and the eukaryotic cells or the prokaryotic microorganisms transformed by this expression vector.

Urate oxidase (EC 1.7.3.3.), which is also called uricase, is an enzyme of the purine degradation pathway. This enzyme does not exist in primates (such as man), birds, a few reptiles or most insects. It is also non-existent in some dogs (such as the dalmatian).

In man, the purine bases—adenine and guanine are—converted to xanthine. The xanthine is oxidized by xanthine oxidase to form uric acid according to the following reaction:

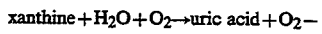

xanthine + $H_2O$ + $O_2$ → uric acid + $O_2-$

The $O_2-$ radical, which is the substrate for superoxide dismutase, is converted by the latter to hydrogen peroxide.

Uric acid, a metabolite present in blood, is normally found essentially in the form of the soluble monosodium salt. However, in certain people, it may happen that the uric acid precipitates and forms calculi. Hyperuricemia, which is an increase in the amount of uric acid circulating in the blood, causes uric acid to deposit in the cartilaginous tissues, leading to gout. Hyperuricemia can also have consequences on the kidneys: an excess of uric acid in the urine and in the kidneys can result in uric acid nephrolithiasis, i.e. the accumulation of renal calculi, which are very painful and can damage the kidney. These calculi are composed of uric acid possibly associated with phosphate and oxalate salts. Overproduction of uric acid can have a variety of origins: congenital metabolic defects, Lesch-Nyhan syndrome, excess ingestion of purine or proteins, treatments with uricosuric drugs, treatments of the hemopathies, particularly the cancerous hemopathies by cytolytic agents (chemotherapy) or by radiotherapy. (Gutman, A. B. and YU, T. F. (1968) Am. J. Med. 45-756-779).

Urate oxidase, the enzyme which catalyzes the degradation of uric acid to allantoin (a compound which is much more soluble than uric acid and does not crystallize at the concentrations reached in biological fluids), therefore has therapeutic value. Used in injections, it has a large number of advantages in the treatment of hyperuricemia and nephrolithiasis: speed of the hypouricemic effect (reduction of hyperuricemia of the order of 50% in less than 24 h), better protection of the kidney against lithiasis compared with other drugs such as allopurinol (a xanthine oxidase inhibitor), etc. At the present time, this enzyme is mainly used as adjuvant for the cytolytic agents in chemotherapy.

The urate oxidase currently used as a drug is obtained by a method comprising the culture of a mycelium of Aspergillus flavus and isolation of the urate oxidase from the culture medium by extraction, together with several steps for purifying this protein. This method, which makes it possible to obtain urate oxidase of high purity, nevertheless has disadvantages. In fact, the physiology and especially the genetics of A. flavus are not easy to work with (WOLOSHUK et al. (1989) Applied environ. microbiol., vol. 55, p. 86-90). It is therefore impossible to obtain strains which produce this enzyme in substantial amounts. Furthermore, A. flavus is liable to produce aflatoxins, which are sometimes difficult to separate off. The purified product should consequently be checked to ensure that it is free from these toxins.

There is therefore a need for a purer urate oxidase of A. flavus as well as for genetic engineering tools and techniques whereby these disadvantages can be overcome.

The Applicant purified the urate oxidase extracted from A. flavus, named thereafter the urate oxidase extract, up to a purity degree higher than that already known for this protein; the Applicant also determined the partial sequence of that protein and built two pools of labelled probes able to hybridize with the nucleotides coding for two portions of that protein. It then constructed an expression vector comprising this cDNA, transformed a strain of E. coli K12 with the latter, cultivated said strain and verified that the lyzate of the cells contained a recombinant protein of the expected molecular weight, which possesses urate oxidase activity (capacity to degrade uric acid allantoîne).

The Applicant also constructed several vectors for expression in eukaryotic cells, comprising a recombinant gene coding for urate oxidase whose sequence contains variations, relative to the isolated cDNA, introduced for the purpose of inserting codons which are customary in eukaryotic cells, transformed different eukaryotic cells with the aid of these vectors, cultivated said cells in a small volume as well as in a larger volume (fermenter), and found that the lyzates of the cells contained a substantial proportion of a recombinant protein of the expected molecular weight, possessing urate oxidase activity. It purified this recombinant protein and partially characterized it, comparatively towards the urate oxidase extract.

Therefore, the present invention relates to a novel protein possessing a specific urate oxidase activity of at least 16 U/mg, which has the following sequence (SEQUENCE ID NO. 1):

| Ser | Ala | Val | Lys | Ala | Ala | Arg | Tyr | Gly | Lys |
|-----|-----|-----|-----|-----|-----|-----|-----|-----|-----|
| Asp | Asn | Val | Arg | Val | Tyr | Lys | Val | His | Lys |
| Asp | Glu | Lys | Thr | Gly | Val | Gln | Thr | Val | Tyr |
| Glu | Met | Thr | Val | Cys | Val | Leu | Leu | Glu | Gly |
| Glu | Ile | Glu | Thr | Ser | Tyr | Thr | Lys | Ala | Asp |
| Asn | Ser | Val | Ile | Val | Ala | Thr | Asp | Ser | Ile |
| Lys | Asn | Thr | Ile | Tyr | Ile | Thr | Ala | Lys | Gln |
| Asn | Pro | Val | Thr | Pro | Pro | Glu | Leu | Phe | Gly |
| Ser | Ile | Leu | Gly | Thr | His | Phe | Ile | Glu | Lys |
| Tyr | Asn | His | Ile | His | Ala | Ala | His | Val | Asn |
| Ile | Val | Cys | His | Arg | Trp | Thr | Arg | Met | Asp |
| Ile | Asp | Gly | Lys | Pro | His | Pro | His | Ser | Phe |
| Ile | Arg | Asp | Ser | Glu | Glu | Lys | Arg | Asn | Val |
| Gln | Val | Asp | Val | Val | Glu | Gly | Lys | Gly | Ile |
| Asp | Ile | Lys | Ser | Ser | Leu | Ser | Gly | Leu | Thr |
| Val | Leu | Lys | Ser | Thr | Asn | Ser | Gln | Phe | Trp |
| Gly | Phe | Leu | Arg | Asp | Glu | Tyr | Thr | Thr | Leu |
| Lys | Glu | Thr | Trp | Asp | Arg | Ile | Leu | Ser | Thr |
| Asp | Val | Asp | Ala | Thr | Trp | Gln | Trp | Lys | Asn |
| Phe | Ser | Gly | Leu | Gln | Glu | Val | Arg | Ser | His |
| Val | Pro | Lys | Phe | Asp | Ala | Thr | Trp | Ala | Thr |
| Ala | Arg | Glu | Val | Thr | Leu | Lys | Thr | Phe | Ala |
| Glu | Asp | Asn | Ser | Ala | Ser | Val | Gln | Ala | Thr |
| Met | Tyr | Lys | Met | Ala | Glu | Gln | Ile | Leu | Ala |
| Arg | Gln | Gln | Leu | Ile | Glu | Thr | Val | Glu | Tyr |

| | | | | | | | | |
|---|---|---|---|---|---|---|---|---|
| Ser | Leu | Pro | Asn | Lys | His | Tyr | Phe | Glu | Ile |
| Asp | Leu | Ser | Trp | His | Lys | Gly | Leu | Gln | Asn |
| Thr | Gly | Lys | Asn | Ala | Glu | Val | Phe | Ala | Pro |
| Gln | Ser | Asp | Pro | Asn | Gly | Leu | Ile | Lys | Cys |
| Thr | Val | Gly | Arg | Ser | Ser | Leu | Lys | Ser | Lys |
| Leu, | | | | | | | | | | optionally preceded by a methionine or which present a substantial degree of homology with that sequence.

Preferably the specific urate oxidase activity of the invention protein is of about 30 U/mg.

A preferred protein of that type is the protein, which, by analysis on a bidimensional gel, presents a spot of molecular mass of about 33.5 kDa and an isoelectric point around 8.0, representing at least 90% of the protein mass.

Preferably the purity degree of the invention protein, determined by liquid chromatography on aC8 grafted silica column, is higher than 80%.

An interesting protein of that type is the protein having an isoelectric point of 8.0. Preferably the amino-terminal serine of that protein carries a blocking group, having preferably a mass around 43 units of atomic mass, such as for example the acetyl group.

The present invention also relates to the drug which contains the invention protein in combination with a pharmaceutically acceptable carrier. The invention protein may advantageously replace, in its different uses, the urate oxidase extract possessing a specific urate oxidase activity of about 8 U/mg, which is sold in the injectable form under the trade mark "Uricozyme" (Vidal 1990).

The invention also relates to a recombinant gene which comprises a DNA sequence coding for the protein having the following sequence (SEQUENCE ID NO. 2):

| | | | | | | | | | | | | | | | |
|---|---|---|---|---|---|---|---|---|---|---|---|---|---|---|---|
| Met | Ser | Ala | Val | Lys | Ala | Ala | Arg | Tyr | Gly | Lys | Asp | Asn | Val | Arg | Val | Tyr |
| Lys | Val | His | Lys | Asp | Glu | Lys | Thr | Gly | Val | Gln | Thr | Val | Tyr | Glu | Met | Thr |
| Val | Cys | Val | Leu | Leu | Glu | Gly | Glu | Ile | Glu | Thr | Ser | Tyr | Thr | Lys | Ala | Asp |
| Asn | Ser | Val | Ile | Val | Ala | Thr | Asp | Ser | Ile | Lys | Asn | Thr | Ile | Tyr | Ile | Thr |
| Ala | Lys | Gln | Asn | Pro | Val | Thr | Pro | Pro | Glu | Leu | Phe | Gly | Ser | Ile | Leu | Gly |
| Thr | His | Phe | Ile | Glu | Lys | Tyr | Asn | His | Ile | His | Ala | Ala | His | Val | Asn | Ile |
| Val | Cys | His | Arg | Trp | Thr | Arg | Met | Asp | Ile | Asp | Gly | Lys | Pro | His | Pro | His |
| Ser | Phe | Ile | Arg | Asp | Ser | Glu | Gln | Arg | Asn | Val | Gln | Val | Asp | Val | Val | Val |
| Glu | Gly | Lys | Gly | Ile | Asp | Ile | Lys | Ser | Ser | Leu | Ser | Gly | Leu | Thr | Val | Leu |
| Lys | Ser | Thr | Asn | Ser | Gln | Phe | Trp | Gly | Phe | Leu | Arg | Asp | Glu | Tyr | Thr | Thr |
| Leu | Lys | Glu | Thr | Trp | Asp | Arg | Ile | Leu | Ser | Thr | Asp | Val | Asp | Ala | Thr | Trp |
| Gln | Trp | Lys | Asn | Phe | Ser | Gly | Leu | Gln | Glu | Val | Arg | Ser | His | Val | Pro | Lys |
| Phe | Asp | Ala | Thr | Trp | Ala | Thr | Ala | Arg | Glu | Val | Thr | Leu | Lys | Thr | Phe | Ala |
| Glu | Asp | Asn | Ser | Ala | Ser | Val | Gln | Ala | Thr | Met | Tyr | Lys | Met | Ala | Glu | Gln |
| Ile | Leu | Ala | Arg | Gln | Gtn | Leu | Ile | Glu | Thr | Val | Glu | Tyr | Ser | Leu | Pro | Asn |
| Lys | His | Tyr | Phe | Glu | Ile | Asp | Leu | Ser | Trp | His | Lys | Gly | Leu | Gln | Asn | Thr |
| Gly | Lys | Asn | Ala | Glu | Val | Phe | Ala | Pro | Gln | Ser | Asp | Pro | Asn | Gly | Leu | Ile |
| Lys | Cys | Thr | Val | Gly | Arg | Ser | Ser | Leu | Lys | Ser | Lys | Leu | | | | |

Because of the degeneracy of the genetic code, there are a large number of DNA sequences coding for a protein whose sequence corresponds to the formula given above. One preferred DNA sequence, particularly appropriate for an expression in the prokaryotic microorganisms, is as follows (SEQUENCE ID NO. 3):

| | | | | |
|---|---|---|---|---|
| ATGTCTGCGG | TAAAAGCAGC | GCGCTACGGC | AAGGACAATG | TTCGCGTCTA |
| CAAGGTTCAC | AAGGACGAGA | AGACCGGTGT | CCAGACGGTG | TACGAGATGA |
| CCGTCTGTGT | GCTTCTGGAG | GGTGAGATTG | AGACCTCTTA | CACCAAGGCC |
| GACAACAGCG | TCATTGTCGC | AACCGACTCC | ATTAAGAACA | CCATTTACAT |
| CACCGCCAAG | TAGAACCCCG | TTACTCCTCC | CGAGCTGTTC | GGCTCCATCC |
| TGGGCACACA | CTTCATTGAG | AAGTACAACC | ACATCCATGC | CGCTCACGTC |
| AACATTGTCT | GCCACCGCTG | GACCCGGATG | GACATTGACG | GCAAGCCACA |
| CCCTCACTCC | TTCATCCGCG | ACAGCGAGGA | GAAGCGGAAT | GTGCAGGTGG |
| ACGTGGTCGA | GGGCAAGGGC | ATCGATATCA | AGTCGTCTCT | GTCCGGCCTG |
| ACCGTGCTGA | AGAGCACCAA | CTCGCAGTTC | TGGGGCTTCC | TGCGTGACGA |
| GTACACCACA | CTTAAGGAGA | CCTGGGACCG | TATCCTGAGC | ACCGACGTCG |
| ATGCCACTTG | GCAGTGGAAG | AATTTCAGTG | GACTCCAGGA | GGTCCGCTCG |
| CACGTGCCTA | AGTTCGATGC | TACCTGGGCC | ACTGCTCGCG | AGGTCACTCT |
| GAAGACTTTT | GCTGAAGATA | ACAGTGCCAG | CGTGCAGGCC | ACTATGTACA |
| AGATGGCAGA | GCAAATCCTG | GCGCGCCAGC | AGCTGATCGA | GACTGTCGAG |
| TACTCGTTGC | CTAACAAGCA | CTATTTCGAA | ATCGACCTGA | GCTGGCACAA |
| GGGCCTCCAA | AACACCGGCA | AGAACGCCGA | GGTCTTCGCT | CCTCAGTCGG |
| ACCCCAACGG | TCTGATCAAG | TGTACCGTCG | GCCGGTCCTC | TCTGAAGTCT |
| AAATTG. | | | | |

Another preferred DNA sequence, which is particularly suitable for expression in eukaryotic cells, such as yeast, is as follows (SEQUENCE ID NO. 4):

| | | | | |
|---|---|---|---|---|
| ATGTCTGCTG | TTAAGGCTGC | TAGATACGGT | AAGGACAACG | TTAGAGTCTA |
| CAAGGTTCAC | AAGGACGAGA | AGACCGGTGT | CCAGACGGTG | TACGAGATGA |
| CCGTCTGTGT | GCTTCTGGAG | GGTGAGATTG | AGACCTCTTA | CACCAAGGCC |
| GACAACAGCG | TCATTGTCGC | AACCGACTCC | ATTAAGAACA | CCATTTACAT |
| CACCGCCAAG | CAGAACCCCG | TTACTCCTCC | CGAGCTGTTC | GGCTCCATCC |
| TGGGCACACA | CTTCATTGAG | AAGTACAACC | ACATCCATGC | CGCTCACGTC |
| AACATTGTCT | GCCACCGCTG | GACCCGGATG | GACATTGACG | GCAAGCCACA |

-continued

| | | | | |
|---|---|---|---|---|
| CCCTCACTCC | TTCATCCGCG | ACAGCGAGGA | GAAGCGGAAT | GTGCAGGTGG |
| ACGTGGTCGA | GGGCAAGGGC | ATCGATATCA | AGTCGTCTCT | GTCCGGCCTG |
| ACCGTGCTGA | AGAGCACCAA | CTCGCAGTTC | TGGGGCTTCC | TGCGTGACGA |
| GTACACCACA | CTTAAGGAGA | CCTGGGACCG | TATCCTGAGC | ACCGACGTCG |
| ATGCCACTTG | GCAGTGGAAG | AATTTCAGTG | GACTCCAGGA | GGTCCGCTCG |
| CACGTGCCTA | AGTTCGATGC | TACCTGGGCC | ACTGCTCGCG | AGGTCACTCT |
| GAAGACTTTT | GCTGAAGATA | ACAGTGCCAG | CGTGCAGGCC | ACTATGTACA |
| AGATGGCAGA | GCAAATCCTG | GCGCGCCAGC | AGCTGATCGA | GACTGTCGAG |
| TACTCGTTGC | CTAACAAGCA | CTATTTCGAA | ATCGACCTGA | GCTGGCACAA |
| GGGCCTCCAA | AACACCGGCA | AGAACGCCGA | GGTCTTCGCT | CCTCAGTCGG |
| ACCCCAACGG | TCTGATCAAG | TGTACCGTCG | GCCGGTCCTC | TCTGAAGTCT |
| AAATTG. | | | | |

Another preferred DNA sequence, which is notably suitable for expression in animal cells, is as follows (SEQUENCE ID NO. 6):

| | | | | |
|---|---|---|---|---|
| | 5′-ATGTC | CGCAGTAAAA | GCAGCCCGCT | ACGGCAAGGA |
| CAATGTCCGC | GTCTACAAGG | TTCACAAGGA | CGAGAAGACC | GGTGTCCAGA |
| CGGTGTACGA | GATGACCGTC | TGTGTGCTTC | TGGAGGGTGA | GATTGAGACC |
| TCTTACACCA | AGGCCGACAA | CAGCGTCATT | GTCGCAACCG | ACTCCATTAA |
| GAACACCATT | TACATCACCG | CCAAGCAGAA | CCCCGTTACT | CCTCCCGAGC |
| TGTTCGGCTC | CATCCTGGGC | ACACACTTCA | TTGAGAAGTA | CAACCACATC |
| CATGCCGCTC | ACGTCAACAT | TGTCTGCCAC | CGCTGGACCC | GGATGGACAT |
| TGACGGCAAG | CCACACCCTC | ACTCCTTCAT | CCGCGACAGC | GAGGAGAAGC |
| GGAATGTGCA | GGTGGACGTG | GTCGAGGGCA | AGGGCATCGA | TATCAAGTCG |
| TCTCTGTCCG | GCCTGACCGT | GCTGAAGAGC | ACCAACTCGC | AGTTCTGGGG |
| CTTCCTGCGT | GACGAGTACA | CCACACTTAA | GGAGACCTGG | GACCGTATCC |
| TGAGCACCGA | CGTCGATGCC | ACTTGGCAGT | GGAAGAATTT | CAGTGGACTC |
| CAGGAGGTCC | GCTCGCACGT | GCCTAAGTTC | GATGCTACCT | GGGCCACTGC |
| TCGCGAGGTC | ACTCTGAAGA | CTTTTGCTGA | AGATAACAGT | GCCAGCGTGC |
| AGGCCACTAT | GTACAAGATG | GCAGAGCAAA | TCCTGGCGCG | CCAGCAGCTG |
| ATCGAGACTG | TCGAGTACTC | GTTGCCTAAC | AAGCACTATT | TCGAAATCGA |
| CCTGAGCTGG | CACAAGGGCC | TCCAAAACAC | CGGCAAGAAC | GCCGAGGTCT |
| TCGCTCCTCA | GTCGGACCCC | AACGGTCTGA | TCAAGTGTAC | CGTCGGCCGG |
| TCCTCTCTGA | AGTCTAAATT | G | | | preceded by a non-translated 5′ sequence favoring expression in animal cells. A preferred non-translated 5′ sequence of this type is the one comprising the sequence (SEQUENCE ID NO. 5) AGCTTGCCGCCACT, located immediately upstream from the sequence described above.

It will be noticed that the protein coded for by the cDNA sequences given above can undergo processing by methionyl aminopeptidase, which cleaves it from its amino-terminal methionine residue.

The invention further relates to an expression vector carrying the above-defined recombinant gene with the means necessary for its expression.

For expression in prokaryotic microorganisms, in particular in *Escherichia coli*, the coding sequence must be inserted into an expression vector containing especially an effective promoter, followed by a ribosome binding site upstream from the gene to be expressed, and also an effective transcription stop sequence downstream from the gene to be expressed. This plasmid must also contain an origin of replication and a selection marker. All these sequences must be chosen as a function of the host cell.

For expression in eukaryotic cells, the expression vector according to the invention carries the above-defined recombinant gene with the means necessary for its expression, for its replication in eukaryotic cells and for selection of the transformed cells. Preferably, this vector carries a selection marker, chosen for example to complement a mutation of the recipient eukaryotic cells, which makes it possible to select those cells which have integrated a large number of copies of the recombinant gene either into their genome or into a multicopy vector.

For expression in animal cells, especially in the cells of Chinese hamster ovaries, CHO, the coding sequence is inserted into a plasmid (for example derived from pBR322) containing two expression units, a first unit, into which the recombinant gene is inserted, before an effective promoter (for example the SV40 early promoter). The sequence around the initiation ATG is preferably chosen as a function of the consensus sequence described by KOZAK (M. KOZAK (1978) Cell, 15, 1109–1123). An intron sequence, for example the intron of mouse α-globin, can be inserted upstream from the recombinant gene, and a sequence containing a polyadenylation site, for example an SV40 polyadenylation sequence, can be inserted downstream from the recombinant gene. The second expression unit contains a selection marker (for example a DNA sequence) coding for dihydrofolate reductase (an enzyme abbreviated hereafter to DHFR). The plasmid is transfected in animal cells, for example DHFR- CHO cells (incapable of expressing DHFR). A line is selected for its methotrexate resistance: it has integrated a large number of copies of the recombinant into its genome and expresses said recombinant gene at a sufficient level.

For expression in eukaryotic cells such as yeast, for example *Saccharomyces cerevisiae*, the coding sequence should be inserted between, on the one hand, sequences recognized as an effective promoter and, on the other hand, a transcription terminator. The array promoter/coding sequence/terminator, which is called an expression cassette, is either cloned in a plasmid vector (single-copy or multicopy) for the yeast, or integrated as a multicopy into the genome of the yeast.

The invention further relates to the eukaryotic cells transformed by the above expression vector. Of value among these eukaryotic cells are strains of the species *Saccharomyces cerevisiae*, in particular those which contain a mutation on one of the genes responsible for the synthesis of leucine or uracil, for example the LEU2 gene or the URA3 gene.

The invention further relates to the animal cells containing this recombinant gene with the means necessary for its expression. Said recombinant gene may, for example, have been introduced into the cells by transfection by the above expression vector, by infection with a virus or a retrovirus carrying said expression vector, or by microinjection.

The invention further relates to the process for producing a recombinant urate oxidase which comprises the steps of:
1) cultivating transformed cells as hereinabove defined;
2) producing the lysis of that cells;
3) isolating and purifying the urate oxidase contained in the obtained lysate.

The invention will be understood more clearly with the aid of the Examples below.

Many of the following techniques, which are well known to those skilled in the art, are described in detail in the work by Maniatis et al.: "Molecular cloning: a laboratory manual" published in 1984 by Cold Spring Harbor Press in New York.

BRIEF DESCRIPTION OF THE DRAWINGS

FIG. 3 shows a nucleotide sequence of clone 9C and of part of clone 9A.

FIG. 4 shows a DNA sequence opened by ATG in position 109 in FIG. 3 and polypeptide coded for. The sequenced peptides obtained by lysis of *A. Flavus urate* oxidase with trypsin (⇌) and protease V8 (-··-) are shown by arrows opposite the polypeptide-coded for.

Figure 1:
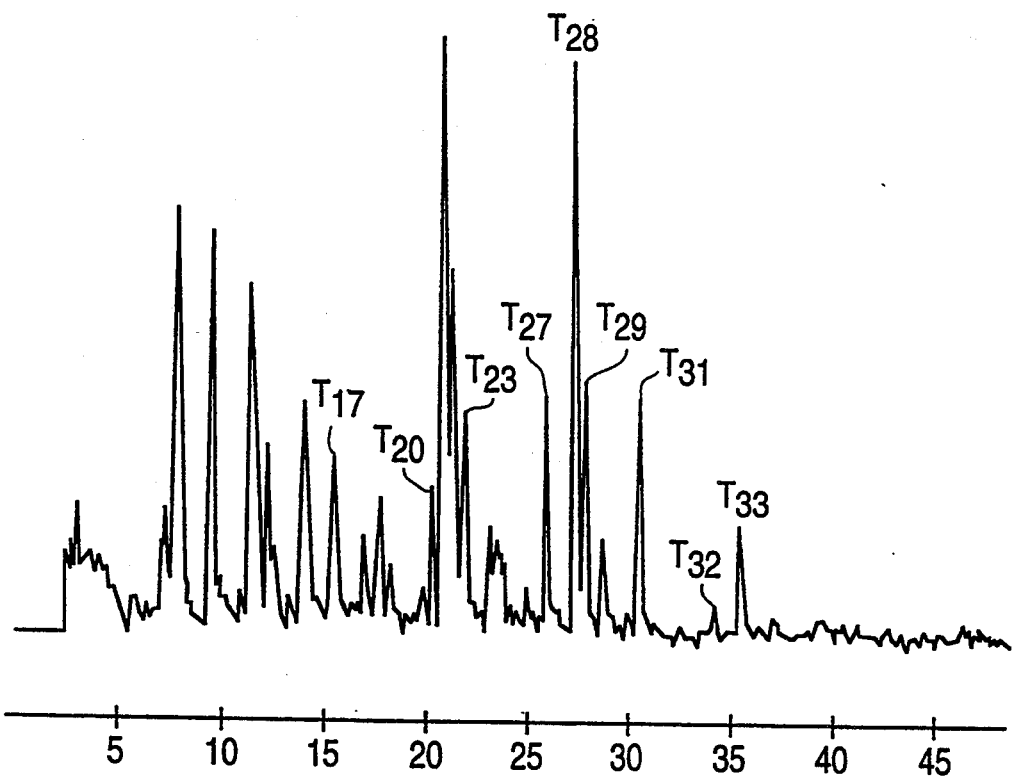
FIG. 1 shows an elution profile by measurement of the optical density at 218 nm of the product of tryptic digestion of urate oxidase.

EXAMPLE 1: Isolation of the messenger RNA's from *Aspergillus flavus*

The strain of *A. flavus* which produces urate oxidase was cultivated under conditions appropriate for the production of urate oxidase, i.e. in a medium containing uric acid and having the following composition: glucose 15 g/l, $MgSO_4.7H_2O$ 1 g/l, $KH_2PO_4$ 0.75 g/l, $CaCO_3$ 1.2 g/l, uric acid 1.2 g/l, KOH 0.5 g/l, soy bean oil 0.66 ml/l, $FeSO_4.7H_2O$ 10 mg/l, $CuSO_4.5H_2O$ 1 mg/l, $ZnSO_4.7H_2O$ 3 mg/l, $MnSO_4.H_2O$ 1 mg/l. The medium is adjusted to pH 7 with $H_2SO_4$ 1M and sterilized at 120° C. for 80 min.

In a 5 l Erlenmeyer flask, 1.5 l of medium are inoculated with about 1 to $3.10^7$ spores.

The culture is incubated for about 40 h at 30° C., with agitation (120 rpm). The mycelium is recovered by filtration on gauze, washed with water and frozen in liquid nitrogen.

15 g of mycelium (wet weight) are thawed, resuspended in 45 ml of lysis buffer and then taken up in the same volume of beads (0.45 μm in diameter). The lysis buffer consists of guanidine thiocyanate 4M, Tris-HCl 10 mM pH 7.6, EDTA 10 mM, β-mercaptoethanol 50 ml/l. The mycelian suspension is ground in a Zellmühler mill (vibrogenic) for 5 min.

The ground material is recovered and the beads are decanted. The supernatant is removed (about 45 ml), brought back to a final concentration of 3M in respect of lithium chloride and stored at 0° C.

After two days, it is centrifuged for 60 min at 10,000 rpm. The supernatant is discarded and the residue is taken up in 40 ml of LiCl 3M and centrifuged again at 10,000 rpm for 1 h 30 min.

The following are added: proteinase K (SIGMA) 40 μg/ml, SDS (0.1% w/v) and EDTA 20 mM. The mixture is incubated at 37° C. for 3 h. Precipitation with 2 volumes of ethanol is followed by washing with 70% ethanol. The residue is taken up in 0.5 ml of TE buffer (Tris-HCl 10 mM, EDTA 1 mM pH 7.5), the mixture is extracted twice with chloroform and precipitation is carried out with ethanol. The RNA's are stored at −80° C. in alcohol.

EXAMPLE 2: Purification of the poly A+ fraction of the RNA's

About 1 mg of RNA is precipitated for 20 min at 4° C. (15,000 rpm) and then washed with 70% ethanol and dried. The residue is taken up in 1 ml of TE buffer and resuspended by agitation in a Vortex. Oligo dT-cellulose type 3 (marketed by Collaborative Research Inc., Biomedicals Product Division) is prepared according to the manufacturer's recommendations. The RNA is deposited on the oligo dT, agitated gently to resuspend the beads and then heated for 1 min at 65° C.

The suspension is adjusted to 0.5M NaCl and then agitated gently for 10 min. It is then centrifuged for 1 min at 1000 rpm, the supernatant is removed and the residue is washed twice with 1 ml of TE buffer containing 0.5M NaCl. The supernatants are removed. The polyadenylated fraction of the RNA's (consisting of the messenger RNA's) is eluted by suspending the beads in 1 ml of TE buffer, then heating this suspension at 60° C. for 1 min and subsequently agitating it for 10 min on a tilting plate. It is then centrifuged for 1 min at 1000 rpm, which makes it possible to recover on the one hand the supernatant containing free mRNA's in solution, and on the other hand the residue of cellulose beads. The above series of operations (starting from elution) is repeated. The supernatants obtained in this way are pooled, the excess beads are removed by centrifugation and the supernatant is precipitated with ethanol containing NaCl in accordance with the usual techniques (Maniatis: op. cit.).

EXAMPLE 3: Building of the cDNA library

The messenger RNA's isolated as described in the previous Example were used to build a cDNA library in vector pTZ19R (marketed by PHARMACIA). This vector is a plasmid comprising a polylinker containing unique restriction sites.

The cloning technique used is the one described by Caput et al. (primer-adapter technique: Caput et al., Proc. Natl. Acad. Sci. (U.S.A.) (1986) 83, 1670–1674).

It consists firstly in digesting the vector with Pst1, adding a polydC tail to the protuberant 3' end and then digesting the resulting plasmids with BamHI. The fragment corresponding to the vector is purified on a column of Sepharose CL4B (Pharmacia). It therefore comprises a polydC tail at one end, the other end being a sticky end of the BamHI type. Secondly, the messenger RNA's are subjected to reverse transcription starting from a primer having the sequence (SEQUENCE ID NO. 7) 5' <GATCCGGGCCCT$_{(12)}$<3. Thus the cDNA's have at their 5' end the sequence GATCC complementary to the BamHI sticky end. The RNA-DNA hybrids obtained by the action of reverse transcriptase are subjected to alkaline hydrolysis, enabling the RNA to be removed. The single-stranded cDNA's are then purified by 2 cycles on a column of Sepharose CL4B and subjected to a treatment with terminal transferase so as to add polydG's at the 3' end. The cDNA's are inserted in single-stranded form into the vector prepared as described above. A second oligonucleotide, the adapter, complementary to the primer, is necessary in order to generate an "open" BamHI site at the 5' end of the cDNA's. After hybridization of the vector, the cDNA and the adapter, the recombinant molecules are circularized by the action of the ligase of phage T4. The single-stranded regions are then repaired by means of the DNA polymerase of phage T4. The plasmid pool obtained in this way is used to transform the MC1061 strain for ampicillin resistance (Casabadan, Chou and Cohen, J. Bact. (1980) 143, pages 971–980.

EXAMPLE 4: Purification of urate oxidase extracted from *A. flavus* and characterization thereof 1) Purification of urate oxidase extracted from *A. flavus*

A preparation of urate oxidase extracted from *A. flavus* (Uricozyme-Laboratoires Clin Midy), having a specific urate oxidase activity of 8 U/ml (the specific urate oxidase activity is the ratio of the urate oxidase activity measured by the test described in Example 9 to the weight of total proteins measured by the Bradford method: Anal. Biochem., 72, 248–254), was repurified by chromatography on a column of Red-agarose 120 grafted agarose (SIGMA), concentration by ultrafiltration and filtration on Ultrogel Aca 44 (IBF), a polyacrylamideagarose gel, according to the following protocol:

Step 1: Affinity chromatography on grafted agarose
Temperature: 4° C.
Column: PHARMACIA K50/30
  diameter=50 mm
  length=33 cm
Resin: Red 120 Agarose (3.000 CL/R-0503 SIGMA)
  (volume of gel=410 ml
  height of gel=20 cm)
Equilibration buffer: glycine/NaOH 20 mM pH 8.3
Elution buffer: glycine/NaOH 20 mM, NaCl 2M pH 8.3
Conditioning flow rate: 250 ml.h$^{-1}$
Operating flow rate: 160 ml.h$^{-1}$
Elution flow rate: 60 ml.h$^{-1}$
  1) Deposit the solution of Uricozyme on the top of the column with the aid of a constant-flow pump.
  2) After adsorption, wash the column with twice its volume of equilibration buffer.
  3) Elute with an ionic strength gradient having the following composition:
    glycine, NaOH, 20 mM pH 8.3/glycine, NaOH, 20 mM+NaCl 2M pH8.3
  The total volume of the gradient is equal to 10 times the volume of the column, divided up equally between the two constituents.
  Chromatographic recording is carried out at λ=280 nm; the urate oxidase pool is collected after combination of the fractions which have a specific urate oxidase activity greater than or equal to 16 U/mg.

Step 2: Concentration of the urate oxidase pool by ultrafiltration with the aid of a Biopass system comprising a 10 kDa ultrafiltration membrane Step 3:
Temperature: 4° C.
Column: PHARMACIA K 50/100
  diameter=50 mm
  length=100 cm
Resin: polyacrylamide-agarose with amine and hydroxyl groups: Ultrogel ACA 44 (IBF)
  volume of gel=1.6 l
  height of gel=80 cm
Equilibration buffer: glycine/NaOH 20 mM pH 8.3
Conditioning flow rate: 40 ml.h$^{-1}$
Operating flow rate: 24 ml.h$^{-1}$
  1) Deposit the concentrated urate oxidase pool on the top of the column with the aid of a constant-flow pump.
  2) After the sample has been deposited, continue to supply the column with the buffer glycine/NaOH 20 mM pH 8.3
  3) After chromatography, wash with NaCl 2M until the UV absorbance value (λ=280 nm)<0.05.
  Store under NaCl 2M at 4° C.
  Chromatographic recording is carried out at λ=280 nm; the urate oxidase pool is collected after combination of the fractions which cojointly have:
    a specific urate oxidase activity greater than or equal to 20 U/mg; and
    only 2 bands in electrophoresis under denaturing conditions (presence of SDS) and with silver nitrate developing (Biorad staining kit), namely:
      a major band of 33–34 kDa
      a minor band of 70–71 kDa.

2) Characterization of purified urate oxidase extracted from *A. flavus* a) Partial sequencing

Direct amino-terminal sequencing of the protein was attempted in order to obtain information on the amino acid sequence of the purified urate oxidase extract, making it possible to synthesize the probes necessary for cloning the cDNA. This sequencing was not successful because of amino-terminal blocking of the protein (cf. f) below).

The following strategy was therefore developed to obtain the partial sequence of urate oxidase:
  cleavage of the protein with proteolytic enzymes (using the enzymes trypsin and protease V8 of *Staphylococcus aureus*
  separation of the resulting polypeptides by reversed phase HPLC
  sequencing of the purified peptides.
α) Hydrolysis of the urate oxidase with trypsin, purification and sequencing of the peptides The urate oxidase, at a concentration of 9 mg/ml in an ammonium carbonate buffer 100 mM pH 8.9, was digested with trypsin (Worthington, TPCK), in a ratio urate oxidase/trypsin of 30/1 by weight, at 30° C. for 24 h. After tryptic hydrolysis, 60 μg of digested urate oxidase were directly injected on to a reversed phase HPLC column of Brownlee G18 grafted silica (column: 10×0.2 cm) equilibrated with acetonitrile 1% (v/v) and trifluoroacetic acid 0.1% (v/v) in water. The peptides were then eluted by a linear gradient of acetonitrile in a solution of trifluoroacetic acid (0.1% v/v) in water, varying from 1% to 60% of acetonitrile in 60 min, at a rate of 150 μl/min. The peptides leaving the column were detected by measurement of the optical density at 218 nm.

The elution profile is shown in FIG. 1, in which the numbers following the letter T (trypsin) correspond to the peaks identified.

Each peak was collected and stored at −20° C. until analyzed on a protein sequencer (model 470 A from Applied Biosystems) equipped with a chromatograph (model 430 A from Applied Biosystems), which continuously analyzes the phenylthiohydantoic derivatives formed, after each degradation cycle. Table I below shows the peptide sequences of the 9 peaks identified which have been assigned SEQUENCE ID NOs. as follows: T 17-SEQUENCE ID NO. 8; T 20-SEQUENCE ID NO. 9; T 23-SEQUENCE ID NO. 10; T 27-SEQUENCE ID NO. 11; T 28-SEQUENCE ID NO. 12; T 29-SEQUENCE ID NO. 13; T 31-SEQUENCE ID NO. 14; T 32-SEQUENCE ID NO. 15; T 33-SEQUENCE ID NO. 16.

β) Hydrolysis of the urate oxidase with protease V8, purification and sequencing of the peptides The urate oxidase, at a concentration of 2 mg/ml in an ammonium acetate buffer 100 mM pH 6.8, was digested with the protease V8 of *Staphylococcus aureus* (Boehringer-Mannheim), in a ratio urate oxidase/protease V8 of 60/1, at 30° C. for 72 h. 160 μg of digested urate oxidase were then injected on to a reversed phase HPLC column of Brownlee G18 grafted silica (column: 10×0.2 cm; particles: 7×0.03 μm), equilibrated with acetonitrile 1% and trifluoroacetic acid 0.1% (v/v) in water. The peptides were then eluted by a linear gradient of acetonitrile in a solution of trifluoroacetic acid in water (0.1% (v/v)), varying from 1% to 60% of acetonitrile in 60 min, at a rate of 150 μl/min. The peptides leaving the column were detected by measurement of the optical density at 218 nm.

Figure 2:
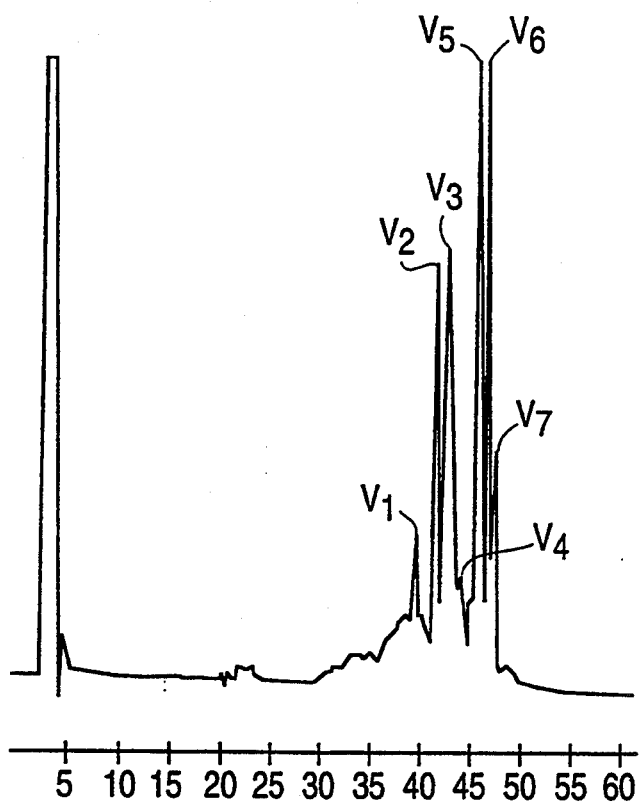
FIG. 2 shows an elution profile by measurement of the optical density at 218 nm of the product of digestion of urate oxidase with protease V8.

The elution profile is shown in FIG. 2, in which the numbers following the letter V (protease V8) correspond to the peaks identified.

Each peak was collected and stored at −20° C. until analyzed on the protein sequencer already mentioned.

Table I below shows the peptide sequences of the 5 peaks identified which have been assigned SEQUENCE ID NOs. as follows: V 1-SEQUENCE ID NO. 17; V 2-SEQUENCE ID NO. 18; V 3-SEQUENCE ID NO. 19; V 5-SEQUENCE ID NO. 20; and V 6-SEQUENCE ID NO. 21.

TABLE I

| | | Sequencing of the products obtained by hydrolysis |
|---|---|---|
| With the aid of trypsin | T 17 | Asn - Val - Gln - Val - Asp - Val - Val - Glu - Gly - Lys |
| | T 20 | Asn - Phe - Ser - Gly - Leu - Gln - Glu - Val |
| | T 23 | Phe - Asp - Ala - Thr - Trp - Ala |
| | T 27 | His - Tyr - Phe - Glu - Ile - Asp - Leu - Ser |
| | T 28 | Ile - Leu - Ser - Thr - Asp - Val - Asp - Ala - Thr - Trp - Gln - Trp - Lys |
| | T 29 | His - Tyr - Phe - Glu - Ile - Asp - Leu - Ser - Trp - His - Lys |
| | T 31 | Ser - Thr - Asn - Ser - Gln - Phe - Trp - Gly - Phe - Leu - Arg |
| | T 32 | Gln - Asn - Pro - Val - Thr - Pro - Pro - Glu - Leu - Phe - Gly - Ser - Ile - Leu - Gly - Thr |
| | T 33 | Gln - Asn - Pro - Val - Thr - Pro - Pro - Glu - Leu - Phe - Gly - Ser - Ile - Leu - Gly - Thr |
| With the aid of protease V8 | V 1 | Tyr - Ser - Leu - Pro - Asn - Lys - His - Tyr - Phe - Glu - Ile - Asp - Leu - Ser - Trp - His - Lys |
| | V 2 | Val - Thr - Leu - Lys - Thr - Phe - Ala - Glu - Asp - Asn - Ser - Ala - Ser - Val - Gln - Ala |
| | V 3 | Thr - Ser - Tyr - Thr - Lys - Ala - Asp - Asn - Ser - Val - Ile - Val - Asp - Thr - Asp - Ser - Ile - Lys - Asn - Thr - Ile - Tyr - Ile - Thr |
| | V 5 | Gly - Lys - Gly - Ile - Asp - Ile - Lys - Ser - Ser - Leu - Ser - Gly - Leu - Thr - Val - Leu - Lys - Ser - Thr - Asn - Ser - Gln - Phe - Trp - Gly - Phe - Leu - Arg |
| | V 6 | Gly - Lys - Gly - Ile - Asp - Ile - Lys - Ser - Ser - Leu - Ser - Gly - Leu - Thr - Val - Leu - Lys | b) Specific activity

The purified urate oxidase extract has a specific activity of about 30 U/mg.

c) Electrophoresis under denaturing conditions

Electrophoresis of the purified urate oxidase extract on polyacrylamide gel in the presence of SDS (sodium dodecylsulfate), followed by silver developing, reveals a high intensity band of about 33–34 kDa and a very low intensity band of about 70–71 kDa.

d) Determination of the isoelectric point

Procedure

Use of ready-to-use gels, namely LKB Ampholines gel plates from Pharmacia with pH ranges of (3.5–9.5) and (5–8).

Deposition of 10 μl of LKB standard proteins (range of isoelectric points of the standard proteins: 3.5–9.5) and 4 μg and 8 μg of purified urate oxidase (on two different lanes).

Run 1 h 30 min, 12 V, 6° C.

Then staining with Coomassie blue (0.1%) in (25% ethanol, 8% acetic acid) to stain the proteins, followed by decolorization with a solution containing 25% of ethanol and 8% of acetic acid (to eliminate the background).

Results: Observation of two close bands (doublet), of isoelectric points 8.1 and 7.9, on each of the two lanes.

e) Two-dimensional gel analysis

Two-dimensional gel analysis makes it possible to separate the proteins in a first stage according to their isoelectric points and in a second stage according to their molecular weights.

Protocol

Sample: solution of purified urate oxidase extract in a glycine buffer 20 mM pH 8.3

Preparation of the sample

Two samples of 5 µg and 10 µg of urate oxidase.

Drying by vacuum centrifugation and taking-up in 5 µl of a lysis buffer having the following composition: urea 2.5M, 3-(3-cholamidopropyl)dimethylammonio-propane-1-sulfonate, CHAPS (Sigma), 2% (v/v), Ampholines amphoterics (LKB) of pH ranges 5–8 and 3.5–9.5, 0.4%, and β-mercaptoethanol 5%.

Isoelectrofocusing gel

Preparation of a solution containing urea 9.5M, CHAPS 5%, LKB Ampholines (pH (3.5–9.5) 1%; pH (5–8) 1%), acrylamide/bisacrylamide (28.4%/1.7%) 3.5% final concentration, $H_2O$.

Filtration and degassing of the solution, followed by addition of 0.075% of tetramethylethylenediamine, Temed (Pharmacia), and 0.015% of ammonium persulfate.

Introduction of the solution into tubes (16×0.12 cm)-polymerization overnight at 20° C.

Cathodic solution: NaOH 0.1M, degassed.
Anodic solution: $H_3PO_4$ 25 mM.
Prerun 45 min at 4 mA (voltage 300 V→1000 V).
Deposition of the samples at the cathode.
Run 19 h at 1000 V and at 20° C.

Demolding of the gels and equilibration for 10 min at 20° C. in a buffer (Tris 0.375M pH 8.8; SDS 3%; dithiothreitol, DTT, 50 mM).

PAGE/SDS denaturing gel

Preparation of a solution containing acrylamide/bisacrylamide (30%/0.8%) 15% final concentration, Tris-HCl (pH 8.8) 0.375M, $H_2O$.

Filtration and degassing of the solution, followed by addition of SDS (0.1%), ammonium persulfate 0.05% and Temed 0.05%.

Polymerization overnight at 4° C. (gel 16×20×0.15 cm).

After equilibration, deposition of the isoelectrofocusing gel on the surface of the PAGE/SDS gel, followed by sealing with agarose.

Electrophoresis buffer: (Tris-HCl 25 mM pH 8.3, glycine 0.192M, SDS 0.1%).

Run 100 mA-6 h at 6° C.

Fixing of the gel in 50% methanol, 10% acetic acid, followed by silver nitrate staining (method of Blum, H., Electrophoresis 1987, 8, p. 93–99).

Scanning of the gel on a Visage 2000 image analyzer from Kodak for determination of the optical density and surface area of each spot and hence for calculation of the quantitative ratio between the spots.

Determination of the molecular weight of the protein by preparation of a two-dimensional gel in the presence of Amersham standard proteins.

Result

Two spots with a molecular weight of the order of 33.5 kDa are observed, one being the majority spot with an isoelectric point of the order of 8.0, intensity 5.2 (representing about 93% of the weight of proteins), and the other being the minority spot with an isoelectric point of the order of 7.4, intensity 0.41 (representing about 7% of the weight of proteins).

f) Determination of the amino-terminal sequence and the mass of the blocking amino-terminal group α) Demonstration of the blocked character of the amino-terminal sequence The amino-terminal sequence was analyzed with the aid of an Applied Biosystem model 470A sequencer coupled with an Applied Biosystem model 120A analyzer of phenylthiohydantoic derivatives. The purified urate oxidase (200 pmol, checked by amino acid analysis) was deposited on the sequencer in the presence of 20 pmol of β-lactoglobulin, a standard protein.

No amino-terminal sequence corresponding to a urate oxidase sequence was detected (by contrast, the amino-terminal sequence of the standard protein was detected, showing that the sequencer was working).

*A. flavus* urate oxidase therefore has the amino-terminal end blocked.

β) Determination of the sequence of an amino-terminal peptide of 32 amino acids and the mass of the blocking amino-terminal group Method: Digestion with cyanogen bromide The purified urate oxidase extract is subjected to gel filtration on Sephadex G25 (PD10-Pharmacia), a gel obtained by crosslinking dextran with epichlorohydrin, equilibrated with a solution containing 7% of formic acid, making it possible to remove the salts and change the buffer. The formic acid concentration is increased to 70% by vacuum centrifugation. Cyanogen bromide is then added to a final concentration of 0.2M and the reaction is allowed to proceed for 20 h under argon, in the absence of light and at room temperature.

Separation by ion exchange chromatography of the peptides derived from digestion of the protein with cyanogen bromide The peptides were separated on an ion exchange column based on mono S hydrophilic resin (Pharmacia).
Buffer A: ammonium acetate 10 mM pH 6.2
Buffer B: ammonium acetate 1M pH 6.2
Flow rate: 0.6 ml/min, peak detection by measurement of the optical density at 278 nm
Gradient: from 0% of B to 100% of B in 30 min-collection of 1 ml fractions The fractions derived from the ion exchange step were analyzed by PAGE/SDS gel according to the method described by Schagger and Von Jagow (1987) Anal. Biochem. 166-p. 368–379.

Purification of the amino-terminal peptide by reversed phase HPLC and analysis thereof by mass spectrometry The peptide derived from the ion exchange step, having a molecular weight of about 4000 Da (on PAGE/SDS gel), was purified on a Beckman Altex C18 column (250×2.1 mm), which is a reversed phase HPLC column based on C18 grafted silica.
Flow rate: 0.3 ml/min, peak detection by measurement of the optical density at 218 nm
Buffer A: $H_2O$/0.1% TFA (trifluoroacetic acid)
Buffer B: acetonitrile/0.1% TFA
Gradient: from 1 to 50% of B in 60 min.

The peptide collected after a first reversed phase HPLC step was repurified on the same reversed phase HPLC column, but with a different gradient.
Gradient: from 1 to 50% of B in 10 min.

The peak collected was subjected to analysis by fast atom bombardment mass spectrometry (FAB/MS) with a glycerol+thioglycerol matrix.

Digestion of the amino-terminal peptide with chymotrypsin and amino acid analysis of the chymotryptic peptides separated by reversed phase HPLC To establish the sequence of the peptide purified by reversed phase HPLC, said peptide was digested with chymotrypsin. The chymotryptic peptides were separated by reversed phase HPLC on a Beckman Altex C18 column (250×2.1 mm).

Flow rate: 0.3 ml/min, peak detection by measurement of the optical density at 218 nm
Buffer A: H2O/0.11% TFA
Buffer B: acetonitrile/0.08% TFA
Gradient: from 1% of B to 50% of B in 60 min-collection of the peeks.

The chymotryptic peptides were identified by amino acid analysis on an Applied Biosystem analyzer (model 420-130A).

Results

The results presented below, which were established after determination of the sequence of the cDNA of *A. flavus* urate oxidase and the deduced amino acid sequence (cf. Example 6), can only be understood in the light of the following:

Analysis of the amino-terminal peptide by mass spectrometry

A difference of about 42 atomic mass units is observed between the two molecular weights determined by mass spectrometry, 3684 and 3666, and the theoretical molecular weights determined from the following sequence (amino acid sequence deduced from the cDNA of *A. flavus* urate oxidase with cleavage of the amino-terminal methionine group and peptide cleavage with cyanogen bromide after the first methionine residue) which corresponds to amino acids 1–31 of SEQUENCE ID NO. 1:

SerAlaValLysAlaAlaArgTyrGly LysAspAsnValArgValTyrLysValHis    (1)
LynAspGluLysThrGlyValGlnThrVal TyrGlu with a carboxy-terminal methionine residue modified by reaction with cyanogen bromide to give either homoserine, 3642, or homoserine lactone, 3624.

There is therefore a blocking group on the amino-terminal serine which accounts for an additional mass of about 42 atomic mass units, probably corresponding to acetylation of said amino-terminal serine (mass of CH3CO—mass of H=42 atomic mass units).

Amino acid analysis of the chymotryptic peptides

This analysis made it possible to show unambiguously that the sequence of the amino-terminal peptide obtained by digestion with cyanogen bromide comprises the sequence (1) described above.

The complete amino acid sequence of urate oxidase is shown hereinafter (SEQUENCE ID NO. 1).

| Ser | Ala | Val | Lys | Ala | Ala | Arg | Tyr | Gly | Lys |
|-----|-----|-----|-----|-----|-----|-----|-----|-----|-----|
| Asp | Asn | Val | Arg | Val | Tyr | Lys | Val | His | Lys |
| Asp | Glu | Lys | Thr | Gly | Val | Gln | Thr | Val | Tyr |
| Glu | Met | Thr | Val | Cys | Val | Leu | Leu | Glu | Gly |
| Glu | Ile | Glu | Thr | Ser | Tyr | Thr | Lys | Ala | Asp |
| Asn | Ser | Val | Ile | Val | Ala | Thr | Asp | Ser | Ile |
| Lys | Asn | Thr | Ile | Tyr | Ile | Thr | Ala | Lys | Gln |

-continued

| Asn | Pro | Val | Thr | Pro | Pro | Glu | Leu | Phe | Gly |
|-----|-----|-----|-----|-----|-----|-----|-----|-----|-----|
| Ser | Ile | Leu | Gly | Thr | His | Phe | Ile | Glu | Lys |
| Tyr | Asn | His | Ile | His | Ala | Ala | His | Val | Asn |
| Ile | Val | Cys | His | Arg | Trp | Thr | Arg | Met | Asp |
| Ile | Asp | Gly | Lys | Pro | His | Pro | His | Ser | Phe |
| Ile | Arg | Asp | Ser | Glu | Glu | Lys | Arg | Asn | Val |
| Gln | Val | Asp | Val | Val | Glu | Gly | Lys | Gly | Ile |
| Asp | Ile | Lys | Ser | Ser | Leu | Ser | Gly | Leu | Thr |
| Val | Leu | Lys | Ser | Thr | Asn | Ser | Gln | Phe | Trp |
| Gly | Phe | Leu | Arg | Asp | Glu | Tyr | Thr | Thr | Leu |
| Lys | Glu | Thr | Trp | Asp | Arg | Ile | Leu | Ser | Thr |
| Asp | Val | Asp | Ala | Thr | Trp | Gln | Trp | Lys | Asn |
| Phe | Ser | Gly | Leu | Gln | Glu | Val | Arg | Ser | His |
| Val | Pro | Lys | Phe | Asp | Ala | Thr | Trp | Ala | Thr |
| Ala | Arg | Glu | Val | Thr | Leu | Lys | Thr | Phe | Ala |
| Glu | Asp | Asn | Ser | Ala | Ser | Val | Gln | Ala | Thr |
| Met | Tyr | Lys | Met | Ala | Glu | Gln | Ile | Leu | Ala |
| Arg | Gln | Gln | Leu | Ile | Glu | Thr | Val | Glu | Tyr |
| Ser | Leu | Pro | Asn | Lys | His | Tyr | Phe | Glu | Ile |
| Asp | Leu | Ser | Trp | His | Lys | Gly | Leu | Gln | Asn |
| Thr | Gly | Lys | Asn | Ala | Glu | Val | Phe | Ala | Pro |
| Gln | Ser | Asp | Pro | Asn | Gly | Leu | Ile | Lys | Cys |
| Thr | Val | Gly | Arg | Ser | Ser | Leu | Lys | Ser | Lys |
| Leu |     |     |     |     |     |     |     |     |     |

EXAMPLE 5: Screening of the bacteria

1) Preparation of the labeled probes

Two pools of probes deduced from amino acid sequences of the protein were synthesized with the aid of a Biosearch 4600 DNA synthesizer. The first pool corresponds to the sequence of residues which correspond to amino acids 1–6 of SEQUENCE ID NO. 11 His-Tyr-Phe-Glu-Ile-Asp (part of the sequence of T 27), i.e. from 5' to 3':

```
    A    T    G    G    G
TCGAT   TC   AA   TA   TG
    T    C    A    A    A
```

This pool in fact consists of $2^4 \times 3 = 48$ different oligonucleotides, representing all the possible combinations.

The second pool corresponds to the sequence of amino acid residues which correspond to amino acids 22–27 of SEQUENCE ID NO. 20 Gln-Phe-Trp-Gly-Phe-Leu (part of the sequence of V 5), i.e. from 5' to 3':

```
  GG    A         G    T
  A    AAGCCCCA   AA   TG
  AA    C         A    C
        T
```

This pool consists of $2^4 \times 4 = 64$ combinations. The probes are labeled with terminal deoxynucleotide transferase (TdT) (marketed by IBI Inc.).

The reaction is carried out on 100 ng of a mixture of oligonucleotides in solution (100 mg/ml) in "Cobalt" reaction buffer (supplied as a 10-fold concentrate by IBI Inc.): 1.4M potassium cacodylate-pH 7.2, 300 mM dithiothreitol, 1 μl of the enzyme terminal deoxynucleotide transferase (IBI Inc.) and 50 μCi of deoxycytidyl triphosphate, dCTP, labeled with P32. The reaction is carried out at 37° C. for 10 min and is then stopped by the addition of 1 μl of EDTA 0.5M. A phenol extraction is carried out and the extract is dialyzed on a column of Biogel P10 polyacrylamide (Biorad: 150-1050).

2) Hybridization and detection of the colonies containing urate oxidase cDNA

About 40,000 colonies are screened by the in situ hybridization technique developed by Grunstein and Hogness (1975, Proc. Natl. Acad. Sci. (U.S.A.), 72, 3961). About 6000 bacteria are plated out in Petri dishes to give isolated colonies. After incubation for 24 h at 37° C., each dish is replicated on 2 filters, each filter being intended to be treated with one of the 2 pools of probes, so that all the colonies obtained are tested with the 2 pools of probes in parallel.

The filters are hybridized with one of the 2 pools of probes in a buffer containing 6×SSC, 10×Denhardt's solution and 100 μg/ml of sonicated and denatured salmon sperm DNA (SIGMA). The hybridization is carried out at a temperature of 42° C. for 16 h. The 6×SSC solution is obtained by diluting a 20×SSC solution. The preparation of the 20×SSC buffer is described by Maniatis, Fritsch and Sambrook (op. cit.). In summary, this buffer contains 175.3 g/l of NaCl and 88.2 g/l of sodium citrate and is adjusted to pH 7 with a few drops of NaOH 10N. The 10×Denhardt's solution contains 1 g of Ficoll, 1 g of polyvinylpyrrolidone and 1 g of human serum albumin per 500 ml of final volume.

After washing in the 6×SSC solution at 42° C. (3 h with 5 changes of bath), the filters are wiped with Joseph paper and subjected to autoradiography. The filters are developed after 16 h. A fraction of about 0.5% of the colonies was found to have hybridized with the 2 pools of probes.

5 colonies from this fraction were taken up and purified. The plasmid DNA was prepared from each of these colonies and this DNA was analyzed by digestion with either BamHI, or HindIII, or both BamHI and HindIII.

After analysis on agarose gel, the 5 plasmids obtained were found to have been linearized by BamHI and by HindIII. The double digestions make it possible to release a fragment corresponding to the whole of the cloned cDNA. The size of this fragment is about 1.2 kb in 3 cases and about 0.9 kb in the other 2 cases. For the following determination, one of the 0.9 kb fragments and one of the 1.2 kb fragments were selected and recloned (see Example 6 below).

EXAMPLE 6: Determination of the sequence of urate oxidase cDNA

On the one hand one of the 0.9 kb fragments (clone 9A) and on the other hand one of the 1.2 kb fragments (clone 9C) were recloned in the DNA of the replicative form of single-stranded phage M13. The DNA of the M13 clones, containing the 0.9 kb fragment on the one hand and the 1.2 kb fragment on the other, was digested with exonuclease so as to generate a series of overlapping M13 clones (procedure: "Cyclone I Biosystem" of IBI). Said clones were sequenced by the dideoxyribonucleotide method (Sanger et al., PNAS-U.S.A.-1977, 14, 5463-5467).

The nucleotide sequence of clone 9C is shown in FIG. 3, which also indicates, with an arrow, the start of clone 9A and, with a nucleotide symbol followed by an asterisk *, the sequenced nucleotides of clone 9A which are not identical to those of clone 9C (when matching the two sequences and the AccI and BamHI restriction sites used in the subsequent constructions (cf. Example 10)).

It is found that the nucleotide sequence of the longer fragment (clone 9C) overlaps that of the shorter fragment (clone 9A) but for two differences (see FIG. 3). One of the differences is quiescent and the other corresponds to a change from a tryptophan residue to a glycine residue. These differences may be due either to differences in the messenger RNA's isolated (cf. Example 2 above) or to errors in the reverse transcriptase used when building the cDNA library (cf. Example 3 above). The sequencing of the genomic DNA of *A. flavus* urate oxidase has made it possible to overcome this ambiguity: it is a tryptophan residue (hence probably an error of the reverse transcriptase.

In the case of the longer fragment, an ATG codon (in position 109 in FIG. 3) opens an open reading frame corresponding to a polypeptide of 302 amino acids, with a molecular weight of about 34,240 Da, whose sequence corresponds to the partial sequence of purified *A. flavus* urate oxidase (cf. Example 4).

FIG. 4 shows the DNA sequence opened by the ATG codon and the polypeptide coded for, and, with arrows opposite the polypeptide coded for, the sequenced peptides (cf. Example 4) obtained by hydrolysis of *A. flavus* urate oxidase with trypsin and protease V8.

It is found that the sequence of the polypeptide terminates in the triplet Ser-Lys-Leu, which is typical of peroxisomal location enzymes (Gould S. J. et al., J. Cell Biology 108 (1989) 1657–1664).

EXAMPLE 7: Construction of an expression vector for urate oxidase cDNA

Plasmid p466, a vector for expression in *E. coli*, was prepared. It comprises a fragment of pBR327 including the origin of replication and the ampicillin resistance gene; it also comprises a synthetic promoter of *E. coli* (R. RODRIGUEZ and M. CHAMBERLIN, "Promoters-Structure and function (1982), Preager), a Shine-Dalgarno sequence followed by a polylinker containing the unique NdeI and KpnI sites, a transcription terminator (derived from phage fd) and the lac i gene.

This plasmid was constructed from an expression plasmid for hGH in *E. coli* (p462) by replacing a fragment carrying the hGH gene with urate oxidase cDNA.

The construction of plasmid p466 will now be described in greater detail in the following account, which will refer to FIGS. 5, 6, 7, 8 and 9.

Figure 5:
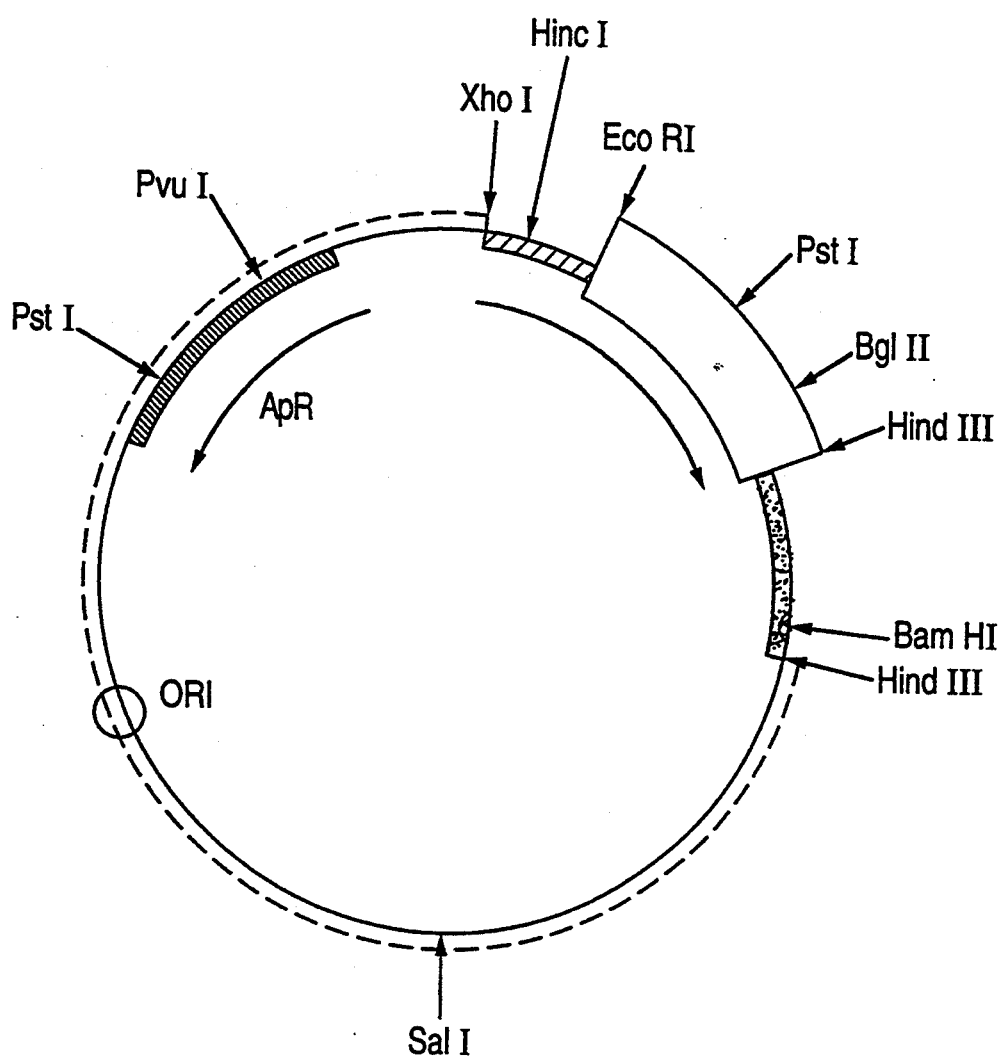
FIG. 5 shows plasmid p163,1.

FIG. 5 shows a restriction map of plasmid p163,1. The different restriction segments are labeled arbitrarily according to the following legend:

▭▭▭▭=DNA segment derived from plasmid pBR322

▭O▭=Location of the origin of replication (ORI)

▬▬▬▬=DNA segment containing the sequence coding for a natural precursor of hGH

▦▦▦▦=DNA segment of phage fd containing a transcription terminator

▨▨▨▨=DNA segment containing a tryptophan-lactose UV5 hybrid promoter-operator

■■■■=DNA segment coding for β-lactamase (ApR: ampicillin resistance)

Figure 6:
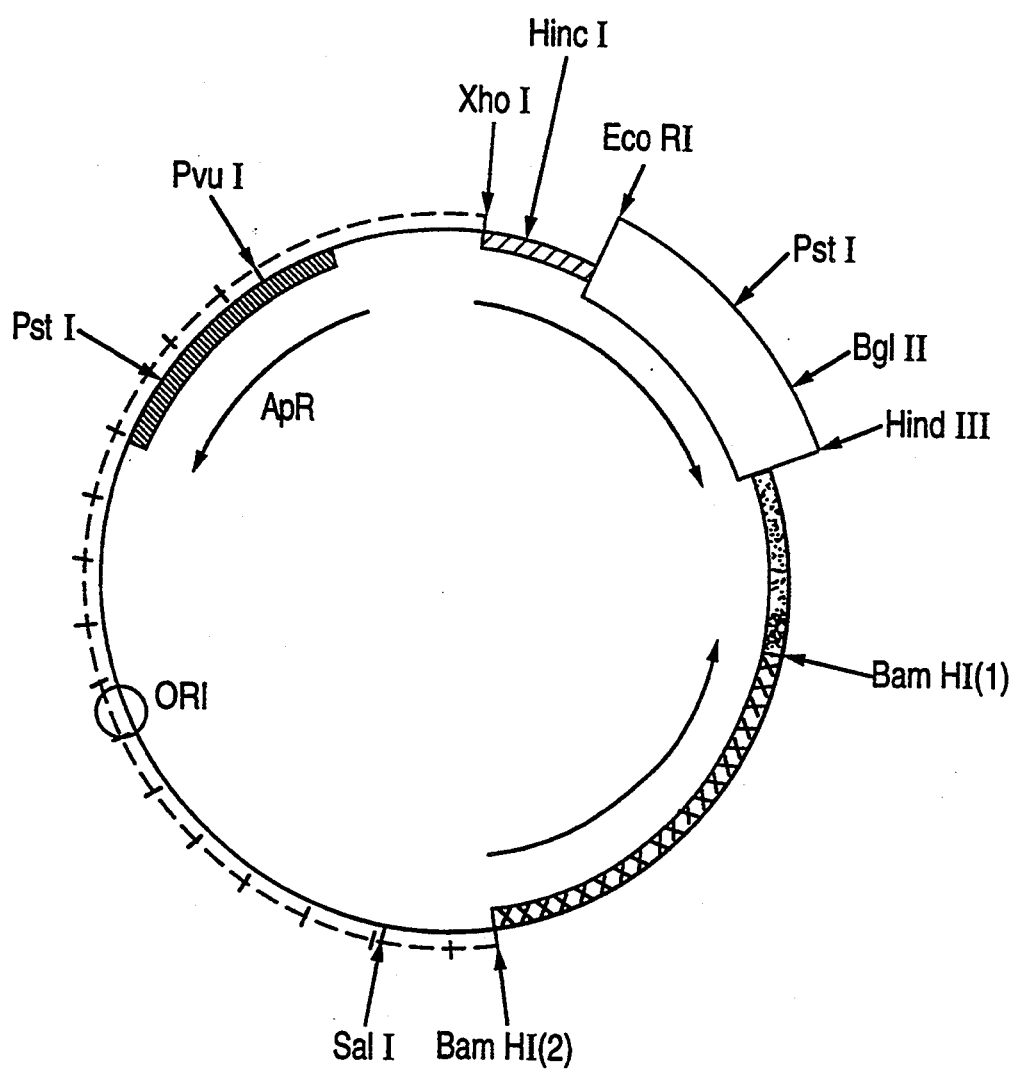
FIG. 6 shows plasmid p160.

FIG. 6 shows the restriction map of plasmid p160, whose PvuI-XhoI-BamHI(1) and PvuI-ORI-BamHI(2) fragments originate respectively from plasmids p163,1 and pBR327 and whose small BamHI(2)-BamHI(1) fragment is fragment 3 described below.

Figure 7:
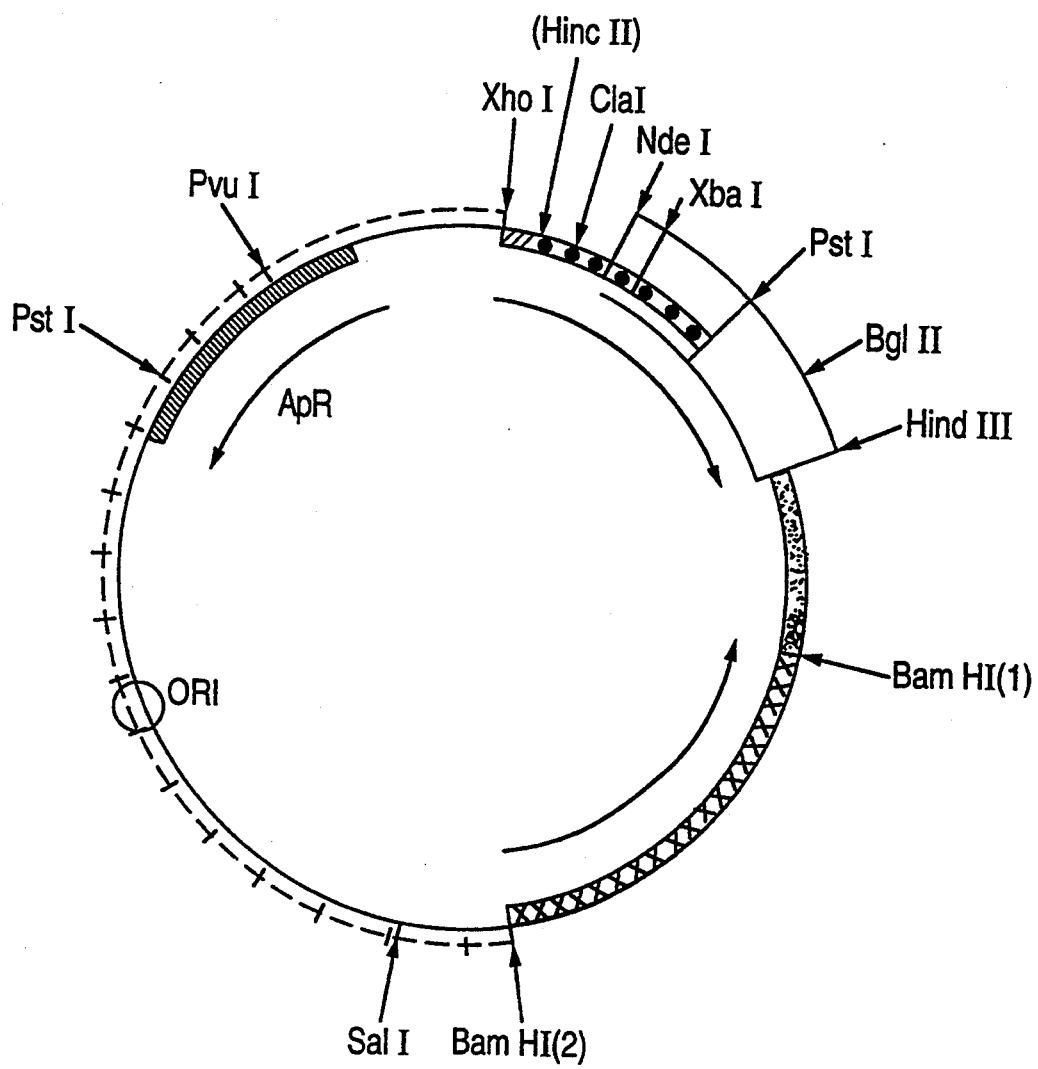
FIG. 7 shows plasmid p373,2.

FIG. 7 shows the restriction map of plasmid p373,2. The different restriction segments are labeled arbitrarily according to the following legend:

=+=+= =PvuI-BamHI sequence derived from plasmid pBR327

====== =PvuI-XhoI sequence derived from plasmid p163,1

▨▨▨▨ =XhoI-HincII sequence derived from plasmid p163,1

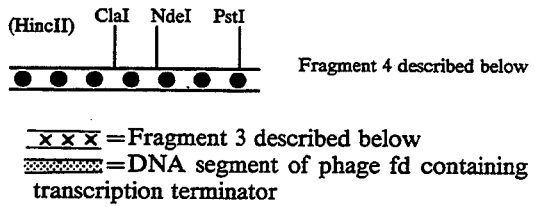

Fragment 4 described below x̄ x̄ x̄ =Fragment 3 described below

▒▒▒▒ =DNA segment of phage fd containing a transcription terminator

Figure 8:
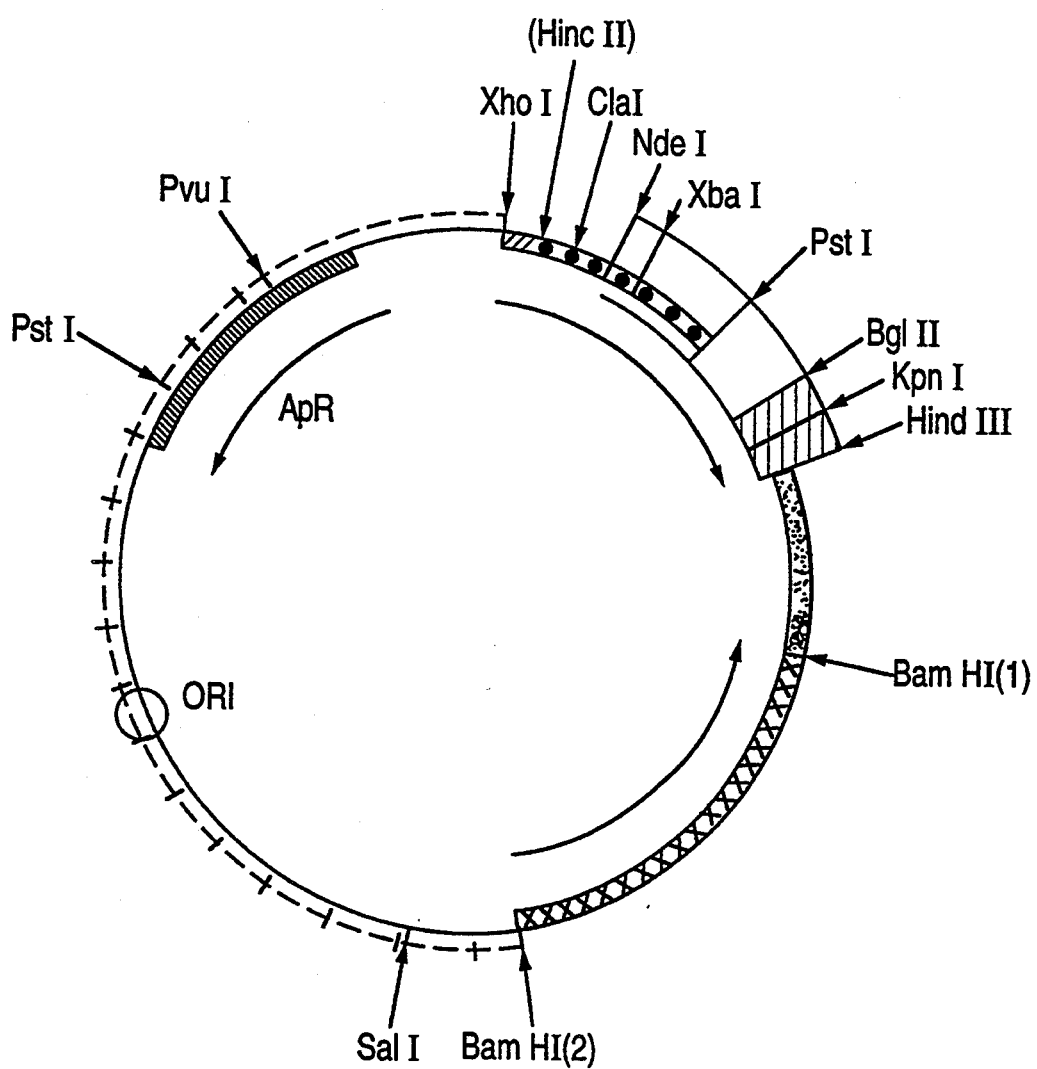
FIG. 8 shows plasmid p462.

FIG. 8 shows a restriction map of plasmid p462, the synthetic BglII-HindIII fragment defined below being represented by: ▨▨▨▨

Figure 9:
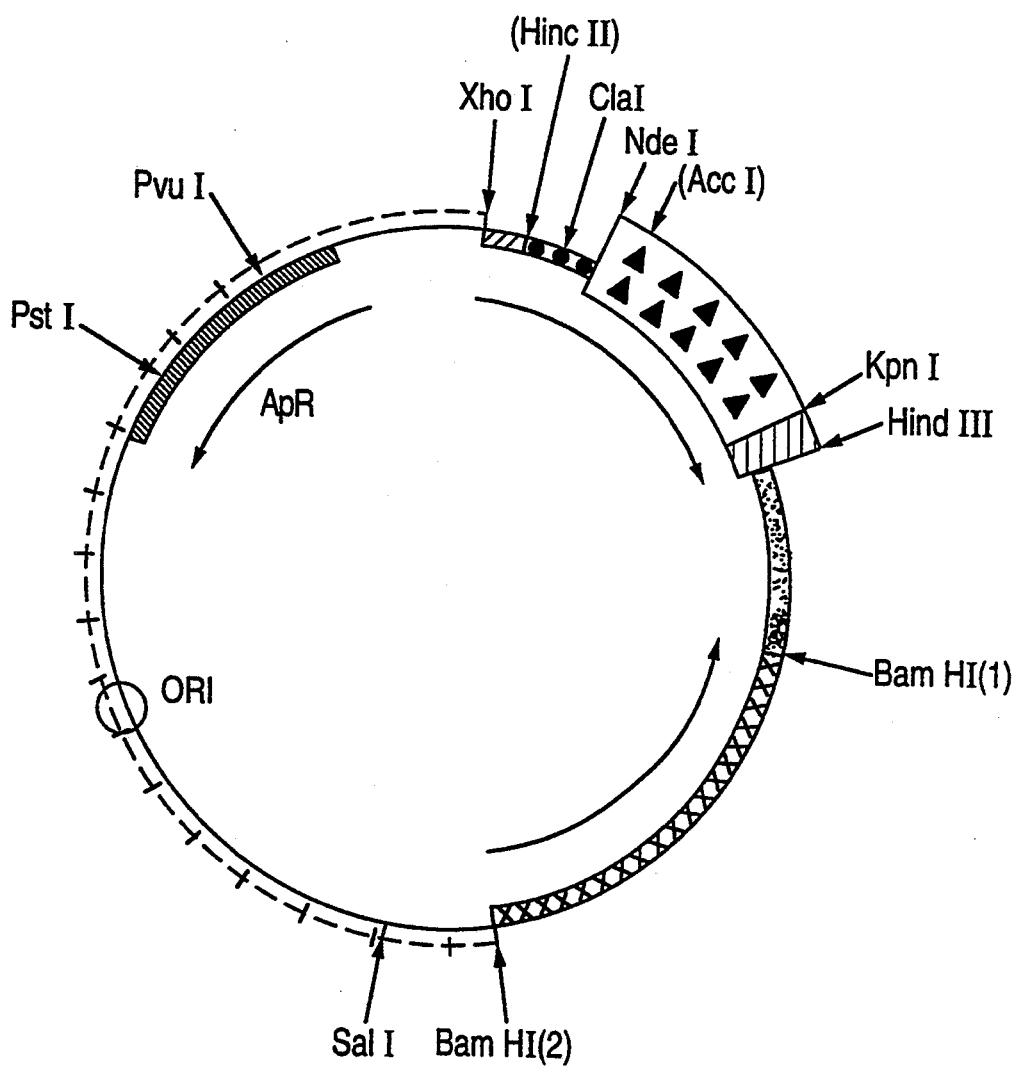
FIG. 9 shows plasmid p466.

FIG. 9 shows a restriction map of plasmid p466, the NdeI-KpnI fragment, comprising the gene coding for urate oxidase, being represented by: ▲▲▲

1) Construction of plasmid p373,2

The strategy employed uses fragments obtained from pre-existing plasmids available to the public, and fragments prepared synthetically by the techniques now in common use. The cloning techniques employed are those described by T. MANIATIS, E. F. FRITSCH and J. SAMBROOK, Cold Spring Harbor Laboratory (1982). The oligonucleotides are synthesized with the aid of a Biosearch 4600 DNA synthesizer.

Plasmid p163,1 (FIG. 5), described in European patent application A-0245138 and deposited in the CNCM under the reference I-530 on Feb. 17, 1986, was digested with the enzymes PvuI and BamHI. This plasmid contains the gene coding for hGH. The PvuI-BamHI fragment-hereafter called fragment 1-containing the site of action of the restriction enzyme XhoI, shown in FIG. 5, was purified.

Likewise, plasmid pBR327, which is well known to those skilled in the art (q.v. SOBERON, X. et al., Gene, 9 (1980) 287–305), was digested with the enzymes PvuI and BamHI. The PvuI-BamHI fragment—hereafter called fragment 2—containing the origin of replication, was purified.

Fragment 3 was then prepared; this is a synthetic BamHI(1)-BamHI(2) fragment containing the lac i gene and its promoter and it has the following sequence (SEQUENCE ID NO. 22), in which the two ends of the strand are identified by the numbers 1 and 2 in order to specify the orientation of the fragment in the plasmids described in FIGS. 6 and 7:

| FRAGMENT 3 |
|---|

BamHI(1)
```
5'     GATCC    GCGGAAGCAT  AAAGTGTAAA  GCCTGGGGTG  CCTAATGAGT
    GAGCTAACTT  ACATTAATTG  CGTTGCGCTC  ACTGCCCGCT  TTCCAGTCGG
    GAAACCTGTC  GTGCCAGCTG  CATTAATGAA  TCGGCCAACG  CGCGGGGAGA
    GGCGGTTTGC  GTATTGGGCG  CCAGGGTGGT  TTTTCTTTTC  ACCAGTGAGA
    CGGGCAACAG  CTGATTGCCC  TTCACCGCCT  GGCCCTGAGA  GAGTTGCAGC
    AAGCGGTCCA  CGCTGGTTTG  CCCCACCACC  CGAAAATCCT  GTTTGATGGT
    GGTTAACGGC  GGGATATAAC  ATGAGCTGTC  TTCGGTATCG  TCGTATCCCA
    CTACCGAGAT  ATCCGCACCA  ACGCGCAGCC  CGGACTCGGT  AATGGCGCGC
    ATTGCGCCCA  GCGCCATCTG  ATCGTTGGCA  ACCAGCATCG  CAGTGGGAAC
    GATGCCCTCA  TTCAGCATTT  GCATGGTTTG  TTGAAAACCG  GACATGGCAC
    TCCAGTCGCC  TTCCCGTTCC  GCTATCGGCT  GAATTTGATT  GCGAGTGAGA
    TATTTATGCC  AGCCAGCCAG  ACGCAGACGC  GCCGAGACAG  AACTTAATGG
    GCCCGCTAAC  AGCGCGATTT  GCTGGTGACC  CAATGCGACC  AGATGCTCCA
    CGCCCAGTCG  CGTACCGTCT  TCATGGGAGA  AAATAATACT  GTTGATGGGT
    GTCTGGTCAG  AGACATCAAG  AAATAACGCC  GGAACATTAG  TGCAGGCAGC
    TTCCACAGCA  ATGGCATCCT  GGTCATCCAG  CGGATAGTTA  ATGATCAGCC
    CACTGACGCG  TTGCGCGAGA  AGATTGTGCA  CCGCCGCTTT  ACAGGCTTCG
    ACGCCGCTTC  GTTCTACCAT  CGACACCACC  ACGCTGGCAC  CCAGTTGATC
    GGCGCGAGAT  TTAATCGCCG  CGACAATTTG  CGACGGCGCG  TGCAGGGCCA
    GACTGGAGGT  GGCAACGCCA  ATCAGCAACG  ACTGTTTGCC  CGCCAGTTGT
    TGTGCCACGC  GGTTGGGAAT  GTAATTCAGC  TCCGCCATCG  CCGCTTCCAC
    TTTTTCCCGC  GTTTTCGCAG  AAACGTGGCT  GGCCTGGTTC  ACCACGCGGG
    AAACGGTCTG  ATAAEAGACA  CCGGCATACT  CTGCGACATC  GTATAACGTT
    ACTGGTTTCA  CATTCACCAC  CCTGAATTGA  CTCTCTTCCG  GGCGCTATCA
    TGCCATACCG  CGAAAGGTTT  TGCGCCATTC  GATGGTGTCC  G           3'
                                                              BamHI(2)
```

Fragments 1, 2 and 3 were then ligated to give plasmid p160, shown in FIG. 6.

This plasmid was partially digested with the restriction enzymes HincII and PstI. The large HincII-PstI fragment, containing the origin of replication and shown in FIG. 6, was then ligated with fragment 4 (SEQUENCE ID NO. 23), shown below, which is a synthetic DNA fragment carrying a sequence coding for the first 44 amino acids of a natural precursor of hGH and, upstream from this sequence, regulatory signals.

FRAGMENT 4

```
                                                                  ClaI
                                                                   ▼
                                          5'  TCGAGCTGACTGACCTGTTGCTTATATTACATCGA
                                                                          NdeI
                                                                           ▼
                                              AGCTCGACTGACTGGACAACGAATATAATGTAGCT
                                                                           ▼
TAGCGTATAATGTGTGGAATTGTGAGCGGATAACAATTTCACACAGTTAACTTTAAGAAGGAGATATACAT
ATCGATATTACACACCTTAACACTCGCCTATTGTTAAAGTGTGTCAATTGAAATTCTTCCTCTATATGTA

ATG GCT ACC GGA TCC CGG ACT AGT CTG CTC GAC TTC CCA ACC ATT CCC TTA TCT AGA CTT TTT
TAC CGA TGG CCT AGG TCA GAC GAG GAC GAT CGA CGG TGG TAA GGG AAT AGA TCT GAA AAA
 M   A   T   G   S   R   T   S   L   L   D   F   P   T   I   P   L   S   R   L   F
-26                                                                Xbal
                                                                    ▼

CCC TGG CTT CAA GAG GGC AGT GCC TTC CGT CTG CAC CAG ATT CCC TTA TCT AGA CTT TTT
GGG ACC GAA GTT CTC CCG TCA CGG AAG GCA GAC GTG GTC TAA GGG AAT AGA TCT GAA AAA
 P   W   L   Q   E   G   S   A   F   R   L   H   Q   I   P   L   S   R   L   F
                                   -1

GAC AAC GCT ATG CTC CGC GCC CAT CGT GCA CTG GAC AAG GAA CTG GCC TTT GAC ACC TAC
CTG TTG CGA TAC GAG GCG CGG GTA GCA CGT GAC CTG TTC CTT GAC CGG AAA CTG TGG ATC
 D   N   A   M   L   R   A   H   R   A   L   D   K   E   L   A   F   D   T   Y
                                                                          PstI
                                                                           ▼
CAG GAG TTT GAA GAA CCA TAT ATC TAG GGT TTC CAG GTG AAG TTC TCA TTC CTG CA
GTC CTC AAA CTT CTT GGT ATA TAG ATC CCA AAG GTC CAC TTC AAG AGT AAG GAC G
 Q   E   F   E   E   P   Y   I   *   G   F   Q   V   K   F   S   F   L
                                                                    44
```

In this fragment, the amino acids are designated by letters according to the following code:

A = Alanine  M = Methionine
C = Cysteine  N = Asparagine
D = Aspartic acid  P = Proline ment derived from this digestion was purified and ligated with a synthetic DNA fragment whose sequence, given below (SEQUENCE ID NO. 25), is intended to reconstitute the end of the hGH gene, followed at the 3' end by the KpnI and SnaBI cloning sites.

```
                  BglII
        GATCTTCAAGCAGACCTACAGCAAGTTCGACACAAACTCACACAACGAT
        ————+————————+————————+————————+————————+————————+
        AAGTTCGTCTGGATGTCGTTCAAGCTGTGTTTGAGTGTGTTGCTA

GACGCACTACTCAAGAACTACGGGCTGCTCTACTGCTTCAGGAAGGACATGGACAAGGTC
        ————+————————+————————+————————+————————+————————+————————+
        CTGCGTGATGAGTTCTTGATGCCCGACGAGATGACGAAGTCCTTCCTGTACCTGTTCCAG

FspI
        GAGACATTCCTGCGCATCGTGCAGTGCCGCTCTGTGGAGGGCAGCTGTGGCTTCTAGTAA
        ————+————————+————————+————————+————————+————————+————————+
        CTCTGTAAGGACGCGTAGCACGTCACGGCGAGACACCTCCCGTCGACACCGAAGATCATT

K   S   HindIII
             p   n
             n   a
             I   BI
        GGTACCCTGCCCTACGTACCA
        ————+————————+————————
        CCATGGGACGGGATGCATGGTTCGA
```

E = Glutamic acid  Q = Glutamine
F = Phenylalanine  R = Arginine
G = Glycine  S = Serine
H = Histidine  T = Threonine
I = Isoleucine  V = Valine
K = Lysine  W = Tryptophan
L = Leucine  Y = Tyrosine The sequences −35 (TTGCTT) and −10 (TATAAT) of the promoter sequence, and the Shine-Dalgarno sequence well known to those skilled in the art, are successively underlined in this fragment.

Plasmid p380,1 was obtained in this way.

Plasmid p380,1 was then digested with the restriction enzymes ClaI and NdeI so as to remove therefrom the small ClaI-NdeI fragment of fragment 4 above and to replace it with the ClaI-NdeI fragment below (SEQUENCE ID NO. 24):

This fragment comprises the BglII and HindIII sticky ends. The novel plasmid formed in this way, p462 (cf. FIG. 8), thus comprises a KpnI site and an NdeI site, which will be used for cloning the fragment containing urate oxidase cDNA in the expression vector.

The hybrid plasmid derived from pTZ19R, carrying urate oxidase cDNA of about 1.2 kb (clone 9C) (see Example 3), comprises a unique KpnI site. This site is located a few base pairs downstream from the cDNA cloning site. Furthermore, urate oxidase cDNA contains an AccI site situated near the 5' end.

The AccI-KpnI fragment, comprising the greater part of this cDNA, was therefore isolated and purified. Two complementary oligonucleotides were also synthesized, whose sequence, given below (SEQUENCE ID NO. 26):

```
5'-TATGTCTGCGGTAAAAGCAGCGCGCTACGGCAAGGACAATGTTCGCGT
   ACAGACGCCATTTTCGTCGCGCGATGCCGTTCCTGTTACAAGCGCAGA-5'
``` is intended to reconstitute the 5' end of the cDNA. This

```
           ClaI
    5' CGATAGCGTATAATGTGTGGAATTGTGAGCGGATAACA
       TATCGCATATTACACACCTTAACACTCGCCTATTGT

NdeI
       ATTTCACACAGTTTTTCGCGAAGAAGGAGATATACA
       TAAAGTGTGTCAAAAAGCGCTTCTTCCTCTATATGTAT  5'
```

The resulting plasmid is plasmid p373,2 (FIG. 7).

2) Construction of plasmid p466

Plasmid p373,2 was subjected to a double digestion with the enzymes BglII and HindIII. The large fragsynthetic fragment obtained in this way has an NdeI end and another AccII end. The fragment and the synthetic sequence were ligated with the expression vector cut by KpnI and by NdeI. This three-fragment ligation makes it possible to obtain the expression vector, called p466, for *E. coli* urate oxidase (cf. FIG. 9). This plasmid was subjected to a series of enzymatic hydrolyses with restriction enzymes, which made it possible to verify the presence of the expected restriction sites, in particular those carried by the gene coding for urate oxidase.

Plasmid p466 therefore contains, by construction, a gene coding for urate oxidase, having the following sequence (SEQUENCE ID NO. 3):

| | | | | |
|---|---|---|---|---|
| ATGTCTGCGG | TAAAAGCAGC | GCGCTACGGC | AAGGACAATG | TTCGCGTCTA |
| CAAGGTTCAC | AAGGACGAGA | AGACCGGTGT | CCAGACGGTG | TACGAGATGA |
| CCGTCTGTGT | GCTTCTGGAG | GGTGAGATTG | AGACCTCTTA | CACCAAGGCC |
| GACAACAGCG | TCATTGTCGC | AACCGACTCC | ATTAAGAACA | CCATTTACAT |
| CACCGCCAAG | CAGAACCCCG | TTACTCCTCC | CGAGCTGTTC | GGCTCCATCC |
| TGGGCACACA | CTTCATTGAG | AAGTACAACC | ACATCCATGC | CGCTCACGTC |
| AACATTGTCT | GCCACCGCTG | GACCCGGATG | GACATTGACG | GCAAGCCACA |
| CCCTCACTCC | TTCATCCGCG | ACAGCGAGGA | GAAGCGGAAT | GTGCAGGTGG |
| ACGTGGTCGA | GGGCAAGGGC | ATCGATATCA | AGTCGTCTCT | GTCCGGCCTG |
| ACCGTGCTGA | AGAGCACCAA | CTCGCAGTTC | TGGGGCTTCC | TGCGTGACGA |
| GTACACCACA | CTTAAGGAGA | CCTGGGACCG | TATCCTGAGC | ACCGACGTCG |
| ATGCCACTTG | GCAGTGGAAG | AATTTCAGTG | GACTCCAGGA | GGTCCGCTCG |
| CACGTGCCTA | AGTTCGATGC | TACCTGGGCC | ACTGCTCGCG | AGGTCACTCT |
| GAAGACTTTT | GCTGAAGATA | ACAGTGCCAG | CGTGCAGGCC | ACTATGTACA |
| AGATGGCAGA | GCAAATCCTG | GCGCGCCAGC | AGCTGATCGA | GACTGTCGAG |
| TACTCGTTGC | CTAACAAGCA | CTATTTCGAA | ATCGACCTGA | GCTGGCACAA |
| GGGCCTCCAA | AACACCGGCA | AGAACGCCGA | GGTCTTCGCT | CCTCAGTCGG |
| ACCCCAACGG | TCTGATCAAG | TGTACCGTCG | GCCGGTCCTC | TCTGAAGTCT |
| AAATTG. | | | | |

(The nucleotides which are different from the nucleotides of the cDNA isolated from *A. flavus* are underlined in the above sequence. These differences were introduced into the synthetic AccI-KpnI fragment so as to have, downstream from the ATG, a nucleotide sequence corresponding more closely to those normally encountered in a prokaryotic gene.)

EXAMPLE 8: Expression of urate oxidase cDNA

The *E. coli* K12 RR1 strain (Bethesda Research Lab. Inc.) was transformed for ampicillin resistance with plasmid p466 and with a negative control plasmid, pBR322. Ampicillin-resistant colonies were obtained in both cases. 1 colony of each type was cultured in a medium (LB+ampicillin 100 μg/ml). After one night at 37° C., with agitation, the two cultures were diluted 100-fold in the medium (LB+ampicillin 100 μg/ml). After culture for 1 h, IPTG (isopropyl-β-D-thiogalactoside) 1 mM is added for 3 h.

Immunodetection of the urate oxidase by Western blot

1) Procedure

An aliquot corresponding to 0.2 ml at OD=1 is taken from the culture medium obtained after induction with IPTG for 3 h. This aliquot is centrifuged and the supernatant is removed. The residue is then subjected to a Western blot—a technique well known to those skilled in the art—which comprises the following steps:

solubilization of the residue by boiling for 10 min in a buffer, called a loading buffer, consisting of Tris-HCl 0.125M pH 6.8, SDS 4%, bromophenol blue 0.002%, glycerol 20%, β-mercaptoethanol 10% (according to the protocol described by LAEMMLI (U. K. LAEMMLI, Nature, 227 (1970) 680–685));

electrophoretic separation of the different proteins contained in the solubilizate, according to the protocol described by LAEMMLI (U. K. LAEMMLI, Nature, 227 (1970) 680–685); and transfer of said proteins contained in the gel on to a nitrocellulose filter (according to the technique of H. TOWBIN et al., Proc. Natl. Acad. Sci. USA 76 (1979) 4350–4354).

Immunodetection, performed according to the technique of BURNETTE (W. W. BURNETTE, Ana. Biochem. 112 (1981) 195–203), involves the following successive operations:

rinsing the nitrocellulose filter for 10 min with a buffer A (Tris-HCl 10 mM, NaCl 170 mM, KCl 1 mM);

bringing the nitrocellulose filter into contact with a buffer B (buffer A with bovine serum albumin added at a rate of 3 g per 100 ml) for 30 min at 37° C.;

bringing the nitrocellulose filter into contact with an immune serum (polyclonal antibodies recognizing *A. flavus* urate oxidase) for 1 h at 37° C.;

rinsing the nitrocellulose filter with buffer B;

bringing the nitrocellulose filter into contact with a solution of protein G, labeled with iodine 125 at a rate of 0.1 microcurie/ml, for 1 h at 37° C.;

rinsing the filter with buffer A;

drying the filter between two absorbent sheets;

bringing the filter into contact with an X-ray film; and developing the film.

2) Results

It is found that the strain transformed by plasmid p466 overproduces a protein with an apparent molecular weight of about 33 kDa, which is recognized by antibodies directed against *A. flavus* urate oxidase and which is absent from the control strain.

EXAMPLE 9: Assay of the urate oxidase activity

An aliquot corresponding to the equivalent of 0.5 ml at OD=1 is taken from the culture medium obtained after induction with IPTG for 3 h under the culture conditions described in the previous Example. This aliquot is centrifuged and the supernatant is removed. The residues are taken up in 1 ml of TEA (triethanolamine) buffer 0.05M pH 8.9. The cell suspension is sonicated twice for 30 s in ice with a W10 ultrasonic sonicator (set to strength 8 and intensity 4). The extracts are centrifuged at 10,000 g for 10 min and the supernatants are used for the assay.

The above operations are carried out for four colonies taken at random from *E. coli* K12 transformed by plasmid p466 (colonies $A_1$, $B_1$, $C_1$ and $D_1$) and one colony transformed by plasmid pBR322.

1) Principle

The conversion of uric acid to allantoin is followed by the decrease in absorbance at 292 nm. The reaction is as follows:

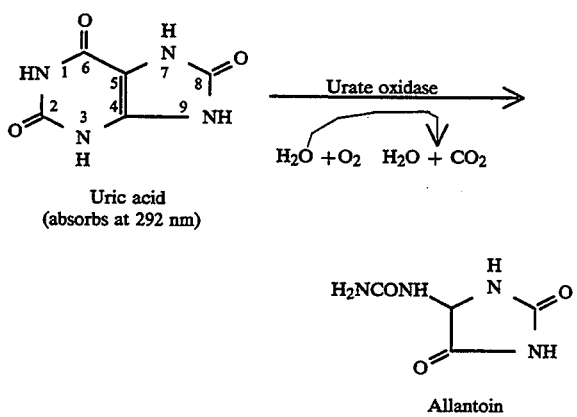

2) Reagents a) TEA 0.05M pH 8.9/EDTA buffer 7.5 g of TEA (reagent for analysis-Prolabo ref. 287.46.266) are dissolved in 400 ml of distilled water;

0.372 g of Complexon III (Merck-ref. 8418) is dissolved in 50 ml of distilled water;

the two solutions are combined and made up to 500 ml (solution 1);

the pH of this solution is adjusted to 8.9 with HCl 0.2N; and the volume is made up to 1000 ml with distilled water (solution 2).

b) Uric acid stock solution 100 mg of uric acid (Carbiochem-ref. 6671) are dissolved in 50 ml of solution 1;

the pH is adjusted to 8.9 with HCl 0.2N; and the volume is made up to 100 ml with distilled water.

The solution obtained can be stored for one week at 4° C.

c) Uric acid substrate solution 1.5 ml of uric acid stock solution (Carbiochem-ref. 6671) are taken and diluted to 100 ml with TEA buffer (reagent for analysis-Prolabo ref. 287.46.266).

This solution must be used the same day.

3) Procedure

The following volumes are introduced into the quartz cell of a spectrophotometer set to 292 nm and thermostated at 30° C.:

600 μl of uric acid substrate solution (preheated to 30° C.) and

100 μl of the above supernatants to which 200 μl of TEA pH 8.9 have been added (preheated to 30° C.).

After mixing, the change in optical density is read off every 30 s for 5 min. ΔE, the variation in optical density per minute, is deduced from these readings.

4) Results

The urate oxidase enzymatic activity A, expressed in U/ml OD 1, is calculated from the ΔE measurement with the aid of the formula $$A = \frac{\Delta E \times V_r \times d}{\epsilon l \times V_{PE}}$$

in which the symbols $V_r$, $d$, $\epsilon l$ and $V_{PE}$ respectively represent the reaction volume (0.9 ml), the dilution factor (2), the extinction coefficient of uric acid at 292 nm (12.5) and the volume of the test sample (0.1 ml).

The results obtained are collated in Table II below:

TABLE II

| E. coli K12 strain transformed by | | Urate oxidase activity (U/ml OD 1) |
|---|---|---|
| pBR322 | | <0.001 |
| | colony A₁ | 0.086 |
| | colony B₁ | 0.119 |
| p466 | | |
| | colony C₁ | 0.135 |
| | colony D₁ | 0.118 |

The above Table clearly shows that the E. coli cells transformed by plasmid p466 are capable of producing urate oxidase activity in the presence of IPTG.

EXAMPLE 10: Construction of three expression vectors for urate oxidase cDNA in yeast: plasmids pEMR469, pEMR473 and pEMR515

The strategy employed uses fragments obtained from pre-existing plasmids available to the public, and fragments prepared synthetically by the techniques now in common use. The cloning techniques employed are those described by T. MANIATIS, E. F. FRITSCH and J. SAMBROOK in "Molecular Cloning, a laboratory manual" (Cold Spring Harbor Laboratory, 1984). The oligonucleotides are synthesized with the aid of a Biosearch 4600 DNA synthesizer.

Figure 10:
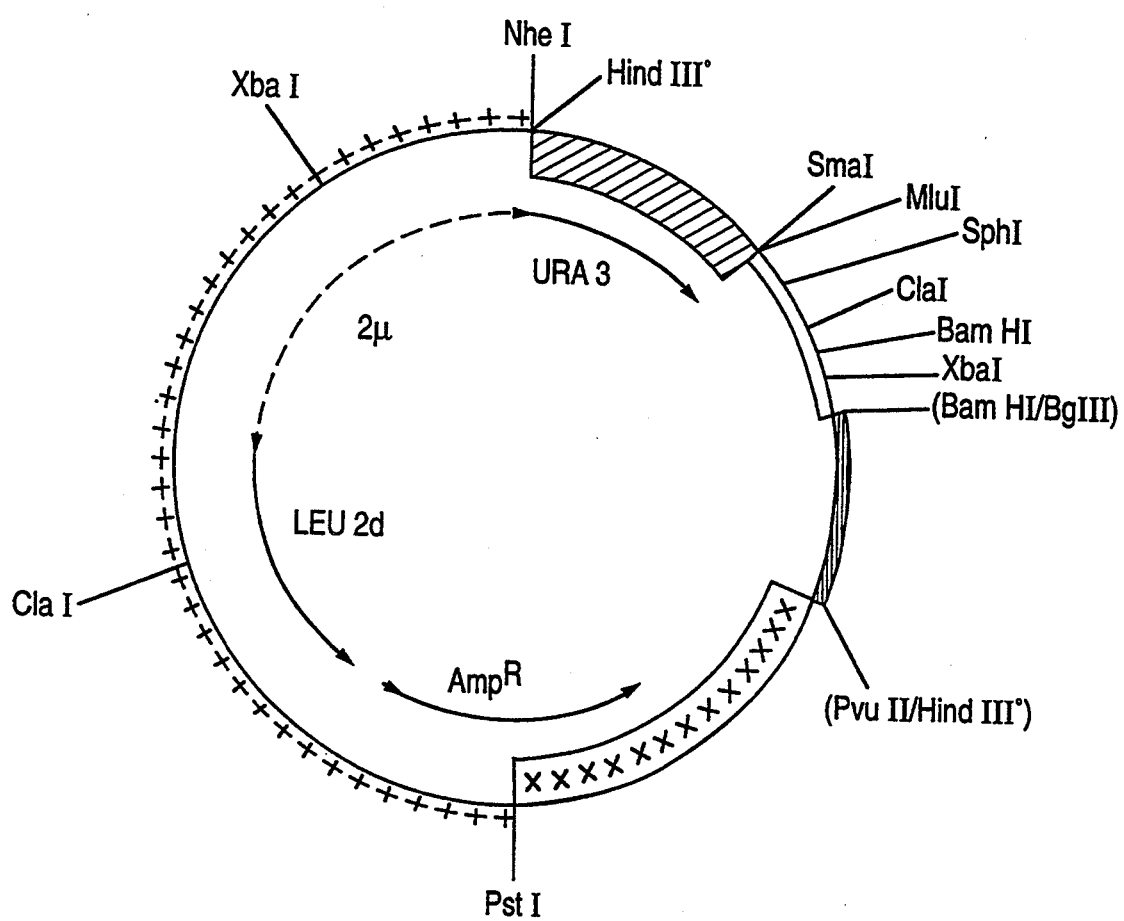
FIG. 10 shows plasmid pEMR414.
Figure 11:
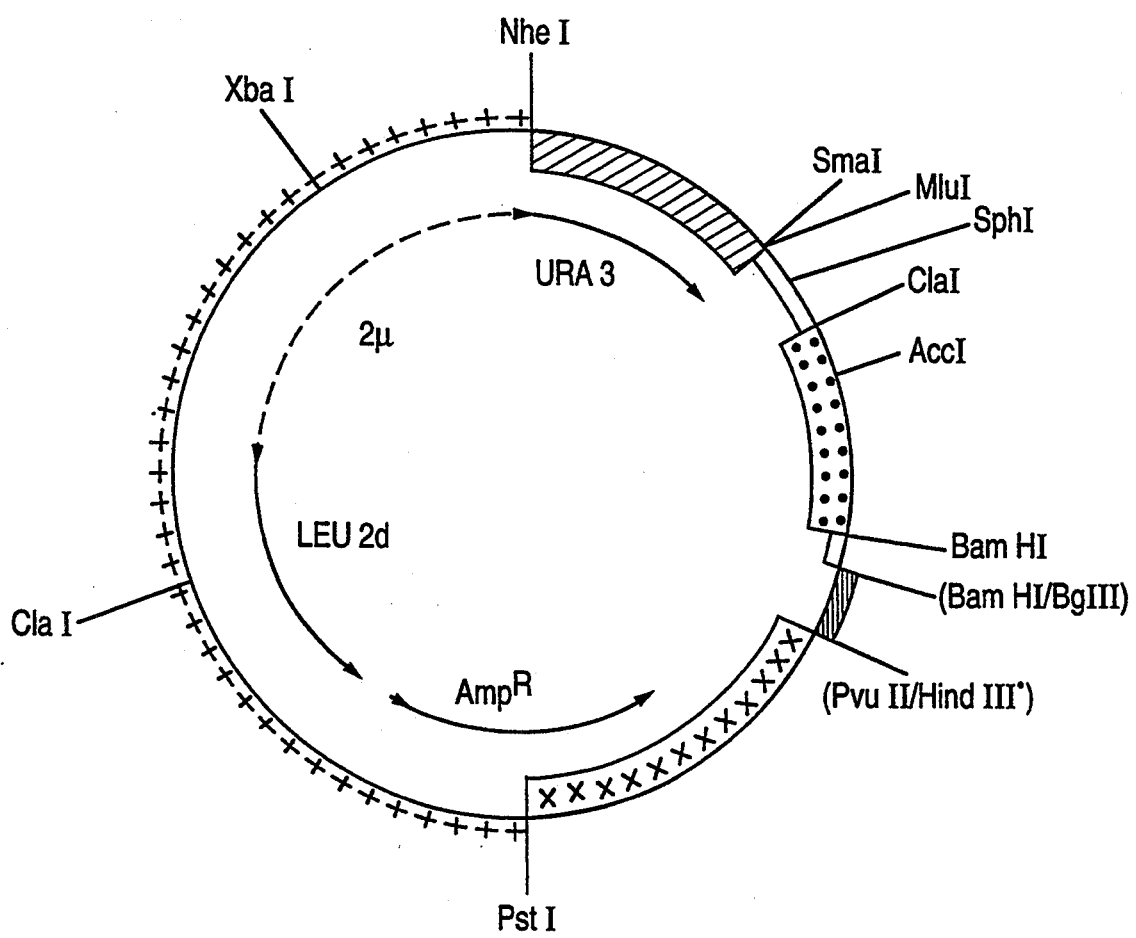
FIG. 11 shows plasmid pEMR469.
Figure 12:
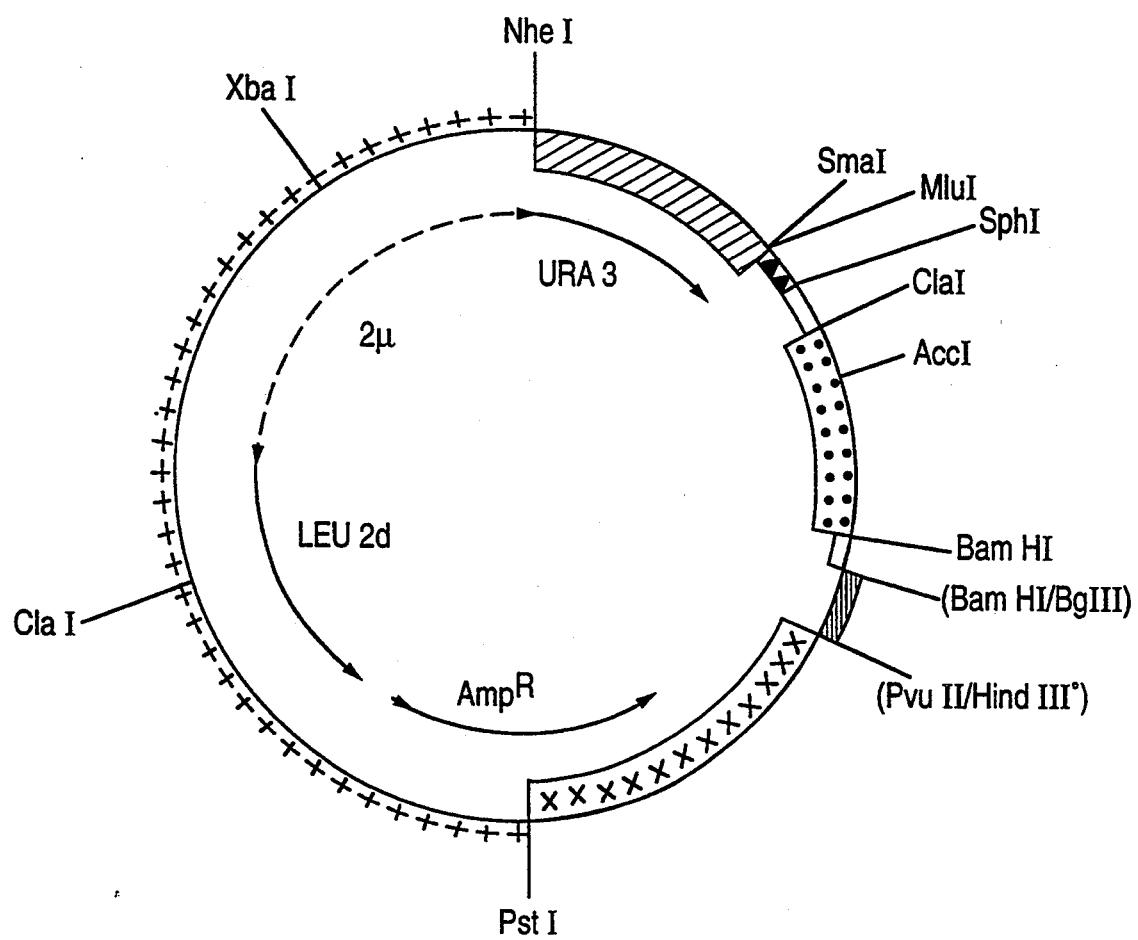
FIG. 12 shows plasmid pEMR473.

The following description will be understood more clearly with reference to FIGS. 10, 11 and 12, which respectively show restriction maps of plasmids pEMR414, pEMR469 and pEMR473. The symbols used in these Figures will be specified in the description below. In the case where a site has been blunted by Klenow polymerase, it carries the index "°"; where the sites have been eliminated by ligation, they are indicated in brackets.

1) Construction of plasmid pEMR469

This plasmid was constructed from the shuttle vector E. coli-yeast pEMR414, constructed by successive ligations of the following components:

the PstI-HindIII° fragment—symbolized by + + + in FIG. 10—of plasmid pJDB207 (BEGGS, 1978: Gene cloning in yeast—p. 175-203 in: Genetic Engineering, vol. 2-WILLIAMSON-Academic Press-London UK) comprising the upstream part of the ampicillin resistance gene Amp^R of pBR322 (Sutcliffe, 1979, Cold Spring Symp. Quart. Biol. 43, 779) and an endogenous 2μ fragment, B form, carrying the LEU2 gene of S. cerevisiae partially modified by the deletion of its promoter (called LEU2d), the locus STB (REP3) and the origin of replication of the 2μ fragment (HARTLEY and DONELSON, 1980, Nature, 286, 860-865). The HindIII end of this fragment has been blunted by the action of Klenow polymerase. It is denoted by HindIII° in FIG. 10.

the HindIII-SmaI fragment—represented by ▨▨▨ in FIG. 10—of chromosome V of yeast containing the URA3 gene with its promoter (ROSE et al., 1984, Gene, 29, p. 113-124). This HindIII-SmaI fragment originates from plasmid pFL1 (CHEVALLIER et al., 1980, Gene 11, 11-19). The HindIII end of this plasmid has been blunted by the action of Klenow polymerase.

an SamI-BamHI fragment—symbolized by ≡≡≡ in FIG. 10—containing a synthetic version of the promoter of the ADH2 gene which differs from the natural version described by RUSSEL and SMITH (RUSSEL et al. (1983) J. Biol. Chem. 258, 2674-2682) only by a few base pairs intended for introducing restriction sites. (The natural sequence could be used with only slightly different results.) The sequence of this fragment is given below (SEQUENCE ID NO. 28):

```
S       M
m       l
a       u
I       I
▼       ▼
GGGACGCGT CT CCT CT GCC GGAA CACC GGG CAT CT CCAACT TAT AAGT T GGAG
    +          +          +          +          +
CCCT GCGC AGAGGAGAC GGCCT T GT GGCCCGT AGAGGT T GAAT ATT C ARCCT C

AAAT AAGAGAAT TT C AGAT T GAGAGAAT GAAAAAAAAAAAAAAAAAAAAAGGC AGAGGAGA
   +          +          +          +          +          +
TTT ATT CT CT TAAAGT CTAACT CT CTT ACT TT TT TT TT TT TT TT TT CCGT CT CCT CT

S
                                           p
                                           h
                                           I
                                           ▼
GCAT AGAAAT GGGGT T C ACT TT TT GGT AAAGCT AT AGCAT GCCT AT C ACAT AT AAAT AGA
   +          +          +          +          +          +
CGT AT CTT TACCCCAAGT GAAAAACCAT TT CGAT AT CGT ACGGAT AGT GT AT ATT T AT CT

GT GCCAGT AGCGACT TT TT T CACACT CGAGAT ACT CTT ACT ACT GCT CT CTT GT T GT TT T
   +          +          +          +          +          +
CACGGT CAT CGCT GAAAAAAGT GT GAGCT CT AT GAGAAT GAT GACGAGAGAACAACAAAA

T AT CACT T CT T GT TT CTT CTT GGT AAAT AGAAT AT CAAGCT ACAAAAAGCAT ACAAT CAA
   +          +          +          +          +          +
AT AGT GAAGAACAAAGAAGAACCATT T AT CTT AT AGT T CGAT GT TT TT CGT AT GT T AGT T

B
X                                                             a
l                                                             m
a                                                             H
I                                                             I
▼                                                             ▼
CT AT C AACT AT T AACT AT AT CGAT ACCAT AT GGAT CCGT CGACT CT AGAGGAT CGT C
   +          +          +          +          +          +
GAT AGT T GAT AAT T GAT AT AGCT AT GGT AT ACCT AGGCAGCT GAGAT CT CCT AGCAG

B
     a
     m
     H
     I
GACT CT AGAG ▼
────────────+
CT GAGAT CT CCT AG
``` the BgIII-HindIII fragment—symbolized by ▬▬▬ in FIG. 10—carrying the 3′ end of the yeast PGK gene. This fragment originates from complete digestion with BgIII of the HindIII fragment of the yeast chromosomal DNA, carrying the PGK gene described by HITZEMAN et al. (1982, Nucleic Acids Res., 10, 7791-7808), which has only one BgIII site. This digestion makes it possible to obtain two HindIII-BgIII fragments of which the smaller, of about 0.4 kb, which carries the 3′ end of the yeast PGK gene, is retained. The sequence of the latter fragment is described by HITZEMANN et al. (op. cit.). The BgIII site is cloned in the BamHI site of the previous fragment (the BamHI and BgIII sites therefore disappearing), and the HindIII site, blunted by the action of Klenow polymerase, is cloned in the PvuII site of the PvuII-PstI fragment of pBR322, described below.

the PvuII-PstI fragment—symbolized by ×̄×̄×̄ in FIG. 10—of pBR322, containing the origin of replication and the downstream part of the ampicillin resistance gene $Amp^R$.

Plasmid pEMR414 formed in this way therefore contains the following components:

an origin of replication and an ampicillin resistance gene $Amp^R$ permitting the replication and selection of the plasmid in *E. coli* cells. These components permit transformation in *E. coli* cells.

an origin of replication for the yeast (ARS), the locus STB and the LEU2 gene of *S. cerevisiae* without promoter and the URA3 gene of *S. cerevisiae* with its promoter. These components permit the replication and selection of the plasmid in *S. cerevisiae* cells and a sufficient partition efficacy in cells containing the endogenous 2μ plasmid.

Plasmid pEMR414 was completely digested with the restriction enzymes NheI and ClaI. The small NheI-ClaI fragment containing the URA3 gene, hereafter called fragment A, was purified.

Plasmid pEMR414 was completely digested with the enzymes NheI and BamHI. The large NheI-BamHI fragment containing especially the LEU2d gene and the origin of replication of plasmid pBR322, hereafter called fragment B, was purified.

al., 1986, Nucl. Ac. Res., vol. 14, 13, pp. 5125–5143) without changing the amino acids coded for. The sequence of this fragment, hereafter called fragment C, is as follows (SEQUENCE ID NO. 29)(the underlined nucleotides are those modified relative to clone 9C):

```
ClaI                                                              AccI
 ▼                                                                 ▼
CGATATACACAATGTCTGCTGTTAAGGCTGCTAGATACGGTAAGGACAACGTTAGAGT
——+————————+————————+————————+————————+————————+——
TATATGTGTTACAGACGACAATTCCGACGATCTATGCCATTCCTGTTGCAATCTCAGA
```

The synthetic ClaI-AccI fragment, containing the start of a gene coding for the protein deduced from the urate oxidase cDNA sequence (clone 9C), was also prepared. This fragment contains modifications, relative to clone 9C, introduced for the purpose of inserting codons which are customary in yeast (q.v. SHARP et al., 1986, Nucl. Ac. Res., vol. 14, 13, pp. 5125–5143)

The plasmid of clone 9C. (cf. FIG. 3) was digested with the enzymes AccI and BamHI. The AccI-BamHI fragment, which contains the end of urate oxidase cDNA, hereafter called fragment D, was purified. This fragment has the following sequence (SEQUENCE ID NO. 30):

```
                                        AccI
                                         ▼
                                        CTACAAGGTTCACAAGGACGAGAAG
                                        ——+————————+————————+
                                        TGTTCCAAGTGTTCCTGCTCTTC

ACCGGTGTCCAGACGGTGTACGAGATGACC          GTCTGTGTGCTTCTGGAGGGTGAGATTGAG
——+————————+————————+                   ——+————————+————————+
TGGCCACAGGTCTGCCACATGCTCTACTGG          CAGACACACGAAGACCTCCCACTCTAACTC

ACCTCTTACACCAAGGCCGACAACAGCGTC          ATTGTCGCAACCGACTCCATTAAGAACACC
——+————————+————————+                   ——+————————+————————+
TGGAGAATGTGGTTCCGGCTGTTGTCGCAG          TAACAGCGTTGGCTGAGGTAATTCTTGTGG

ATTTACATCACCGCCAAGCAGAACCCCGTT          ACTCCTCCCGAGCTGTTCGGCTCCATCCTG
——+————————+————————+                   ——+————————+————————+
TAAATGTAGTGGCGGTTCGTCTTGGGGCAA          TGAGGAGGGCTCGACAAGCCGAGGTAGGAC

GGCACACACTTCATTGAGAAGTACAACCAC          ATCCATGCCGCTCACGTCAACATTGTCTGC
——+————————+————————+                   ——+————————+————————+
CCGTGTGTGAAGTAACTCTTCATGTTGGTG          TAGGTACGGCGAGTGCAGTTGTAACAGACG

CACCGCTGGACCCGGATGGACATTGACGGC          AAGCCACACCCTCACTCCTTCATCCGCGAC
——+————————+————————+                   ——+————————+————————+
GTGGCGACCTGGGCCTACCTGTAACTGCCG          TTCGGTGTGGGAGTGAGGAAGTAGGCGCTG

AGCGAGGAGAAGCGGAATGTGCAGGTGGAC          GTGGTCGAGGGCAAGGGCATCGATATCAAG
——+————————+————————+                   ——+————————+————————+
TCGCTCCTCTTCGCCTTACACGTCCACCTG          CACCAGCTCCCGTTCCCGTAGCTATAGTTC

TCGTCTCTGTCCGGCCTGACCGTGCTGAAG          AGCACCAACTCGCAGTTCTGGGGCTTCCTG
——+————————+————————+                   ——+————————+————————+
AGCAGAGACAGGCCGGACTGGCACGACTTC          TCGTGGTTGAGCGTCAAGACCCCGAAGGAC

CGTGACGAGTACACCACACTTAAGGAGACC          TGGGACCGTATCCTGAGCACCGACGTCGAT
——+————————+————————+                   ——+————————+————————+
GCACTGCTCATGTGGTGTGAATTCCTCTGG          ACCCTGGCATAGGACTCGTGGCTGCAGCTA

GCCACTTGGCAGTGGAAGAATTTCAGTGCA          CTCCAGGAGGTCCGCTCGCACGTGCCTAAG
——+————————+————————+                   ——+————————+————————+
CGGTGAACCGTCACCTTCTTAAAGTCACCT          GAGGTCCTCCAGGCGAGCGTGCACCCATTC

TTCGATGCTACCTGGGCCACTGCTCGCGAG          GTCACTCTCAAGACTTTTGCTGAAGATAAC
——+————————+————————+                   ——+————————+————————+
AAGCTACGATGGACCCGGTGACGAGCGCTC          CAGTGAGACTTCTGAAAACGACTTCTATTC

AGTGCCAGCGTGCAGGCCACTATGTACAAG          ATCCCAGAGCAAATCCTGGCGCGCCAGCAG
——+————————+————————+                   ——+————————+————————+
TCACCGTCGCACGTCCGGTCATACATGTTC          TACCGTCTCGTTTAGGACCGCGCGGTCGTC

CTGATCCAGACTGTCGAGTACTCCTTGCCT          AACAACCACTATTTCGAAATCGACCTCAGC
——+————————+————————+                   ——+————————+————————+
GACTAGCTCTGACAGCTCATCAGCAACCGA          TTGTTCGTGATAAAGCTTTAGCTGGACTCG

TGGCACAAGGGCCTCCAAAACACCCGCAAC          AACGCCGACGTCTTCGCTCCTCAGTCGGAC
——+————————+————————+                   ——+————————+————————+
ACCGTGTTCCCGGAGGTTTTGTGCCCGTTC          TTGCGGCTCCAGAAGCGACGGATCAGCCTG
```

```
CCCAACGGTCTCATCAAGTGTACCGTCGGC
———————+———————————+——————————+
GGGTTGCCAGACTAGTTCACATGGCAGCCG

AACATGATTCTCACGTTCCCGAGTTTCCAA
———————+———————————+——————————+
TTGTACTAAGAGTGCAAGGCCTCAAAGGTT

TAGCATTCATTCACTTGTTTTTACTTCCA
———————+———————————+——————————+
ATCGTAAGTAAGTGAACAAAAATGAAGGT
```

-continued
```
CGGTCCTCTCTCAAGTCTAAATTGTAAACC
———————+———————————+——————————+
GCCAGGAGAGACTTCAGATTTAACATTTCG GGCAAACTGTATATAGTCTGGGATAGGGTA
———————+———————————+——————————+
CCGTTTGACATATATCAGACCCTATCCCAT AAAAAAAAAAAAAAAAAAAAAAAAAAAAAA
———————+———————————+——————————+
TTTTTTTTTTTTTTTTTTTTTTTTTTTTTT
```

```
                              ▽ BamHI
AAAAAAAAAAAAAAAAAAAAAAGGGCCCG
———————+———————————+————
TTTTTTTTTTTTTTTTTTTTTCCCGGGCCT    AG
```

Fragments A, B, C and D were ligated to give plasmid pEMR469 shown in FIG. 11, in which the symbols have the same meanings as in FIG. 10, the novel ClaI-AccI and AccI-BamHI fragments being symbolized by ▒▒▒▒▒.

2) Construction of plasmid pEMR473

Plasmid pEMR469 was completely digested with the enzymes MluI and SphI. The large MluI-SphI fragment, containing the urate oxidase gene, was then ligated with the synthetic fragment, whose sequence is given below, corresponding to a part (200 bp) of the sequence upstream from the TATA component of promoter GAL7 of S. cerevisiae, said part comprising the upstream activation sequences (UAS).

```
M
l
u
I
CGCGTCTATACTTCGGAGCACTGTTGAGCGAAGGCTCATTAGATATATTTTCTGTCAT
——+———————+———————+———————+———————+———————+———————
    AGATATGAAGCCTCGTGACAACTCGCTTCCGAGTAATCTATATAAAAGACAGTA

TTTCCTTAACCCAAAAATAAGGGAGAGGGTCCAAAAAGCGCTCGGACAACTGTTGACCGT
——+———————+———————+———————+———————+———————+———————
AAAGGAATTGGGTTTTTATTCCCTCTCCCAGGTTTTTCGCGAGCCTGTTGACAACTGGCA

GATCCGAAGGACTGGCTATACAGTGTTCACAAAATAGCCAAGCTGAAAATAATGTGTAGC
——+———————+———————+———————+———————+———————+———————
CTAGGCTTCCTGACCGATATGTCACAAGTGTTTTATCGGTTCGACTTTTATTACACATCG

S
                                                          p
                                                          h
                                                          I
CTTTAGCTATGTTCAGTTAGTTTGGCATG
——+———————+———————+————
GAAATCGATACAAGTCAATCAAACC
```

Plasmid pEMR473 obtained in this way is shown in FIG. 12, in which the symbols have the same meanings as in FIG. 11, the novel MluI-SphI fragment introduced being symbolized by ▲ ▲.

3) Construction of plasmid pEMR515

Plasmid pEMR473 was partially digested with the enzyme XbaI and totally digested with the enzyme MluI. The large XbaI-MluI fragment was purified. This fragment contains especially the sequences of the origin of replication and the locus STB of the 2μ fragment, the LEU2d gene, the ampicillin resistance gene Amp$^R$, the origin of replication of pBR322 and the expression cassette for urate oxidase. On the other hand, it contains neither the URA3 gene nor that part of the 2μ fragment which is between the XbaI and NheI sites.

The large XbaI-MluI fragment was recircularized via the following sequence adapter (SEQUENCE ID NO. 32) containing MluI and modified XbaI sticky ends:

```
modified XbaI
▼
  CTAGGCTAGCGGGCCCGCATGCA
      CGATCGCCCGGGCGTACGTGCGC▲
                             MluI
```

Plasmid pEMR515 obtained in this way has only one of the three components of the target FRT site of the recombinase coded for by the FLP gene of the 2μ fragment.

Plasmids pEMR469, pEMR473 and pEMR515 possess the gene coding for urate oxidase, which has the following sequence (SEQUENCE ID NO. 4):

| ATGTCTGCTG | TTAAGGCTGC | TAGATACGGT | AAGGACAACG | TTAGAGTCTA |
| CAAGGTTCAC | AAGGACGAGA | AGACCGGTGT | CCAGACGGTG | TACGAGATGA |
| CCGTCTGTGT | GCTTCTGGAG | GGTGAGATTG | AGACCTCTTA | CACCAAGGCC |
| GACAACAGCG | TCATTGTCGC | AACCGACTCC | ATTAAGAACA | CCATTTACAT |
| CACCGCCAAG | CAGAACCCCG | TTACTCCTCC | CGAGCTGTTC | GGCTCCATCC |

| | | | | |
|---|---|---|---|---|
| TGGGCACACA | CTTCATTGAG | AAGTACAACC | ACATCCATGC | CGCTCACGTC |
| AACATTGTCT | GCCACCGCTG | GACCCGGATG | GACATTGACG | GCAAGCCACA |
| CCCTCACTCC | TTCATCCGCG | ACAGCGAGGA | GAAGCGGAAT | GTGCAGGTGG |
| ACGTGGTCGA | GGGCAAGGGC | ATCGATATCA | AGTCGTCTCT | GTCCGGCCTG |
| ACCGTGCTGA | AGAGCACCAA | CTCGCAGTTC | TGGGGCTTCC | TGCGTGACGA |
| GTACACCACA | CTTAAGGAGA | CCTGGGACCG | TATCCTGAGC | ACCGACGTCG |
| ATGCCACTTG | GCAGTGGAAG | AATTTCAGTG | GACTCCAGGA | GGTCCGCTCG |
| CACGTGCCTA | AGTTCGATGC | TACCTGGGCC | ACTGCTCGCG | AGGTCACTCT |
| GAAGACTTTT | GCTGAAGATA | ACAGTGCCAG | CGTGCAGGCC | ACTATGTACA |
| AGATGGCAGA | GCAAATCCTG | GCGCGCCAGC | AGCTGATCGA | GACTGTCGAG |
| TACTCGTTGC | CTAACAAGCA | CTATTTCGAA | ATCGACCTGA | GCTGGCACAA |
| GGGCCTCCAA | AACACCGGCA | AGAACGCCGA | GGTCTTCGCT | CCTCAGTCGG |
| ACCCCAACGG | TCTGATCAAG | TGTACCGTCG | GCCGGTCCTC | TCTGAAGTCT |
| AAATTG. | | | | |

EXAMPLE 11: Transformation of the EMY761 yeast strain by plasmids pEMR469, pEMR473 and pEMR515-Transformation of the EMY500 and GRF18 yeast strains by plasmid pEMR515-Transformation with selection either for the prototrophy of uracil or for the prototrophy of leucine Three non-isogenic strains of *Saccharomyces cerevisiae* were used as recipient strains:
the EMY761 strain (Matα, leu2, ura3, his3, gal)
the EMY500 strain (Matα, leu2, ura3, pep4)
the GRF18 strain (Matα, leu2, his3)

The GRF18 strain is well known to those skilled in the art (Gerry FINK, MIT, U.S.A.). The EMY761 and EMY500 strains are related to the GRF18 strain. They were obtained by successively crossing the GRF18 strain with a ura3 strain derived from the FL100 strain (deposited in the ATCC under n° 28 383) and with the 20B12 strain (Matα, tsp1, pep4) described by E. W. JONES (E. W. JONES et al. (1977) Genetics, 85, 23).

The GRF18 strain can be obtained by curing plasmid pEMR515 of the GRF18 pEMR515 (leu+) strain deposited in the CNCM under reference n° I-920 on Dec. 28, 1989, and the EMY500 strain can be obtained by curing plasmid pEMR515 of the EMY500 pEMR515 (leu+) strain deposited in the CNCM under reference n° I-919 on Dec. 28, 1989.

These strains contain mutations (leu2 and ura3 capable of being complemented by the LEU2d defective selection marker and the URA3 selection marker, which are present in each of plasmids pEMR469 and pEMR473.

1) Transformation with selection for the prototrophy of uracil

A colony of the EMY761 strain was used to inoculate 100 ml of a medium called liquid YPG medium (cf. Table III below). When the cell density had reached $10^7$ cells per ml, the cells were treated with lithium acetate 0.2M for transformation by a technique well known to those skilled in the art and described by ITO et al. (ITO et al., 1983, J. Bacteriology 153, 163–168).

The EMY761 cells were transformed in parallel with about 1 μg of each of plasmids pEMR469 and pEMR473. The transformed cells are selected for the auxotrophic character of uracil (ura+) on a medium called uracil-free solid medium (cf. Table III below). An EMY761 pEMR469 (ura+) transformed strain and an EMY761 pEMR473 (ura+) transformed strain were thus retained.

2) Transformation with selection for the prototrophy of leucine

The transformation technique used is a variant of that described by Beggs et al. (Beggs et al. (1978) Nature 275, 104–109). It consists in subjecting yeasts to a protoplastization treatment in the presence of an osmotic stabilizer, namely sorbitol at a concentration of 1M.

The precise transformation protocol is specified below:

a) 200 ml of liquid YPG medium (cf. Table III) are inoculated with about $5 \times 10^6$ cells of a culture in the stationary phase, and the culture inoculated in this way is agitated overnight at 30° C.

b) When the density of the culture reaches about $10^7$ cells per ml, the cells are centrifuged at 4000 rpm for 5 min and the residue is washed with sorbitol 1M.

c) The cells are suspended in 5 ml of sorbitol solution 1M containing 25 mM EDTA and 50 mM dithiothreitol, and are incubated for 10 min at 30° C.

d) The cells are washed once with 10 ml of sorbitol 1M and suspended in 20 ml of sorbitol. Zymolase-100T (a preparation obtained by partial purification of *Arthobacter luteus* culture supernatant on an affinity column and containing β-1,3-glucan laminaripentahydrolase, marketed by SEYKAGAKU KOGYO Co. Ltd.) is added up to a final concentration of 20 μg/ml and the suspension is incubated at room temperature for about 15 min.

e) The cells are resuspended in 20 ml of a medium containing sorbitol, called sorbitol YPG medium (cf. Table III below) and incubated for 20 min at 30° C., with gentle agitation.

f) The cells are centrifuged for 3 min at 2500 rpm.

g) The cells are resuspended in 9 ml of transformation formation buffer (sorbitol 1M, Tris-HCl 10 mM pH 7.5 and CaCl$_2$ 10 mM).

h) 0.1 ml of cells and 5 μl of DNA solution (about 5 μg) are added and the suspension obtained is left for 10 to 15 min at room temperature.

i) 1 ml of the following solution is added: polyethylene glycol PEG 4000 20%, Tris-HCl 10 mM pH 7.5 and CaCl$_2$ 10 mM.

j) 0.1 ml of the suspension obtained in i) is poured into a tube containing leucine-free solid regeneration medium (cf. Table III below) which has been melted beforehand and kept liquid at about 45° C. The suspension is poured into a Petri dish containing a solidified layer of 15 ml of leucine-free solid regeneration medium.

k) Step j) is repeated with the remainder of the cell suspension obtained in i).

The transformed strains start to appear after three days.

The EMY761 pEMR469 (leu+), EMY761 pEMR473 (leu+), EMY761 pEMR515 (leu+), GRF18 pEMR515 (leu+) and EMY500 pEMR515 (leu+) transformed strains were thus retained.

---

Principal media used in Examples 11, 12, 13 and 14 uracil-free solid medium 6.7 g of Yeast nitrogen base without Amino Acids (from DIFCO)
5.0 g of casein hydrolyzate (Casamino acids from DIFCO)
10 g of glucose
20 g of agar
Mix all the ingredients in distilled water and make up the final volume to 1 l with distilled water. Autoclave for 15 min at 120° C.

uracil-free liquid medium

Use the formulation of the uracil-free solid medium without the agar. Autoclave for 15 min at 120° C.

leucine-free solid medium 6.7 g of Yeast nitrogen base without Amino Acids (from DIFCO)
20 mg of adenine
20 mg of uracil
20 mg of l-tryptophan
20 mg of l-histidine
20 mg of l-arginine
20 mg of l-methionine
30 mg of l-tyrosine
30 mg of l-isoleucine
30 mg of l-lysine
50 mg of l-phenylalanine
100 mg of l-glutamic acid
150 mg of l-valine
400 mg of l-leucine
20 g of glucose
20 g of agar
Mix all the ingredients in distilled water. Make up the final volume to 1 l with distilled water. Autoclave for 15 min at 120° C. After autoclaving, add 200 mg of l-threonine and 100 mg of l-aspartic acidleucine-free solid regeneration medium Use the formulation of the leucine-free solid medium, mixing in 30 g of agar instead of 20 g and adding 182 g of sorbitol to the mixture.

leucine-free liquid medium

Use the formulation of the leucine-free solid medium without the agar. Autoclave for 15 min at 120° C. After autoclaving, add 200 mg of l-threonine and 100 mg of l-aspartic acid.

liquid YP medium 10 g of yeast extract (Bacto-yeast extract from DIFCO)
20 g of peptone (Bacto-peptone from DIFCO)
Mix the ingredients in distilled water. Make up the final volume to 1 l with distilled water. Autoclave for 15 min at 120° C.

liquid YPG medium

Use the formulation of the liquid YP medium, adding, after autoclaving, glucose at a concentration of 20 g/l.

sorbitol YPG medium

Use the formulation of the liquid YPG medium, adding, after autoclaving, sorbitol at a concentration of 1 M.

ethanol-glycerol YP medium

Use the formulation of the liquid YP medium. After autoclaving, add 10 ml of ethanol 100% (1% final concentration) and 30 g of glycerol.

ethanol-glycerol-galactose YP medium

Use the formulation of the liquid YP medium. After autoclaving, add 10 ml of ethanol 100%, 30 g of glycerol and 30 g of galactose.

---

EXAMPLE 12: Expression, in an Erlenmeyer flask, of urate oxidase cDNA by the EMY761 pEMR469 (ura+), EMY761 pEMR473 (ura+), EMY761 pEMR469 (leu+) and EMY761 pEMR473 (leu+) strains-Immunodetection by Western blot-Assay of the urate oxidase activity and the soluble proteins 1) Expression of urate oxidase cDNA a) Strains selected on uracil-free medium A colony of each of the EMY761 pEMR469 (ura+) and EMY761 pEMR473 (ura+) strains was cultured in 20 ml of uracil-free liquid medium (cf. Table III, Example 11). After one night at 30° C., with agitation, the two cultures were centrifuged for 10 min at 7000 rpm. The residues were taken up in 10 ml of sterile distilled water and centrifuged again for 10 min at 7000 rpm. Expression of the urate oxidase was induced by taking up the cells in 20 ml of ethanol-glycerol YP medium (cf. Table III, Example 11) for the EMY761 pEMR469 (ura+) strain and in 20 ml of ethanol-glycerol-galactose YP medium (cf. Table III, Example 11) for the EMY761 pEMR473 (ura+) strain. The cultures were incubated again at 30° C. for 22 h, with agitation.

b) Strains selected on leucine-free medium

In a first stage, a colony of each of the EMY761 pEMR469 (leu+) and EMY761 pEMR473 (leu+) strains was cultured in 20 ml of leucine-free liquid medium (cf. Table III, Example 11). This made it possible to obtain and maintain a large number of copies of plasmids by carrying out the selection for complementation of the leu2mutation by the LEU2d gene carried by plasmids pEMR469 and pEMR473.

After one night at 30° C., with agitation, the two cultures were centrifuged for 10 min at 7000 rpm. The residues were taken up in 10 ml of sterile distilled water and centrifuged again for 10 min at 7000 rpm. Expression of the urate oxidase was induced by taking up the cells in 20 ml of ethanol-glycerol YP medium for the EMY761 pEMR469 (leu+) strain and in 20 ml of ethanol-glycerol-galactose YP medium (cf. Table III, Example 11) for the EMY761 pEMR473 (leu+) strain. The cultures were incubated again at 30° C. for 22 h, with agitation.

c) Control strain

The non-transformed EMY761 strain, i.e. the EMY761 strain without plasmid, was cultivated as above. It was subjected on the one hand to induction in 10 ml of ethanol-glycerol liquid YP medium and on the other hand to induction in 10 ml of ethanol-glycerol-galactose YP medium.

2) Preparation of the samples a) The cells cultivated in 1a), 1b) and 1c) were centrifuged and the supernatant was removed. The residues were taken up in 10 ml of distilled water and centrifuged for 10 min at 7000 rpm. The residues washed in this way were taken up in about 1 ml of triethyleneamine buffer, TEA, of pH 8.9. About 300 μl of cells taken up in said buffer were lyzed in the presence of glass beads (from 400 to 500 μm in diameter), representing about half the final volume. This mixture was agitated vigorously in a Vortex 4 times for 1 min, the samples being placed in ice for 30 s between grinding operations. The liquid was withdrawn from the tubes with a Pasteur pipette and transferred to a microtube. The glass beads were washed once with about 200 μl of TEA buffer of pH 8.9. The beads were agitated in a Vortex once for 1 min and the liquid was withdrawn with a Pasteur pipette and added to the above lyzate. The lyzate was then centrifuged in a microtube for 5 min at 7000 rpm. The supernatant was cautiously withdrawn and stored at −20° C. for Western blot, assay of the urate oxidase activity and assay of the proteins. The residue of the lyzed cells was stored separately at −20° C. for Western blot (cf. 3) below).

Furthermore, samples of the cultures prepared in 1a) and 1b) were taken in the following manner before induction: 2 ml of culture were centrifuged for 10 min at 7000 rpm. The residues were taken up in 500 μl of distilled water and centrifuged again for 5 min at 7000 rpm. The residues were taken up in about 200 μl of TEA buffer of pH 8.9 and lyzed as above in the presence of glass beads. The supernatants and the residues of the lyzed cells were stored separately at −20° C.

3) Immunodetection of the urate oxidase by Western blot a) Procedure

The residues and the supernatants of the different samples were subjected to a Western blot—a technique well known to those skilled in the art—which comprises the following steps:

- solubilization of the residue by boiling for 10 min in a buffer, called a loading buffer, consisting of Tris-HCl 0.125M pH 6.8, SDS 4%, bromophenol blue 0.002%, glycerol 20%, β-mercaptoethanol 10% (according to the protocol described by LAEMMLI (U. K. LAEMMLI, Nature, 227 (1970) 680–685));
- electrophoretic separation of the different proteins contained in the solubilizate, according to the protocol described by LAEMMLI (U. K. LAEMMLI, Nature, 227 (1970) 680–685); and
- transfer of said proteins contained in the gel on to a nitrocellulose filter (according to the technique of H. TOWBIN et al., Proc. Natl. Acad. Sci. USA 76 (1979) 4350–4354).

Immunodetection, performed according to the technique of BURNETTE (W. W. BURNETTE, Ana. Biochem. 112 (1981) 195–203), involves the following successive operations:

- rinsing the nitrocellulose filter for 10 min with a buffer A (Tris-HCl 10 mM, NaCl 170 mM, KCl 1 mM);
- bringing the nitrocellulose filter into contact with a buffer B (buffer A with bovine serum albumin added at a rate of 3 g per 100 ml) for 30 min at 37° C.;
- bringing the nitrocellulose filter into contact with an immune serum (polyclonal antibodies recognizing A. flavus urate oxidase) for 1 h at 37° C.;
- rinsing the nitrocellulose filter with buffer B;
- bringing the nitrocellulose filter into contact with a solution of protein G, labeled with iodine 125 at a rate of 0.1 microcurie/ml, for 1 h at 37° C.;
- rinsing the filter with buffer A;
- drying the filter between two absorbent sheets;
- bringing the filter into contact with an X-ray film; and
- developing the film.

b) Results

It is found that the EMY761 pEMR469 (ura+), EMY761 pEMR473 (ura+), EMY761 pEMR469 (leu+) and EMY761 pEMR473 (leu+) strains produce a protein with an apparent molecular weight of about 33 kDa, which is recognized by antibodies directed against A. flavus urate oxidase and which is absent from the control strain.

It is also found that the non-induced strains produce none or very little of the protein described above.

Comparison between the amounts of this protein for the residues and the supernatants makes it possible to deduce that about 80% of said protein is in soluble form in the lyzate.

4) Assay of the urate oxidase activity

The urate oxidase activity was measured on the supernatants of the lyzed cells according to the procedure described in Example 9 above.

The results obtained are collated in Table IV below, which specifies the urate oxidase activity in U/ml for each strain induced by glycerol-ethanol, each strain induced by glycerol-ethanol-galactose and each non-induced strain.

TABLE IV

| Strain/Inducer | Urate oxidase activity (U/ml) |
|---|---|
| EMY761/YP ethanol-glycerol-galactose | <0.1 |
| EMY761/YP ethanol-glycerol | <0.1 |
| EMY761 pEMR469 (ura+)/(non-induced) | 0.4 |
| EMY761 pEMR469 (ura+)/YP ethanol-glycerol | 12 |
| EMY761 pEMR469 (leu+)/(non-induced) | 0.17 |
| EMY761 pEMR469 (leu+)/YP ethanol-glycerol | 36 |
| EMY761 pEMR473 (ura+)/(non-induced) | <0.1 |
| EMY761 pEMR473 (ura+)/YP ethanol-glycerol-galactose | 12.5 |
| EMY761 pEMR473 (leu+)/(non-induced) | <0.1 |
| EMY761 pEM473 (leu+)/YP ethanol-glycerol-galactose | 15.3 |

The above Table clearly shows that the yeast cells transformed by these plasmids pEMR469 and pEMR473 are capable of producing urate oxidase activity after induction.

5) Assay of the total soluble proteins in the lyzates

The protein assay kit from BIORAD was used for assaying the total proteins present in the supernatant of the lyzed cells. It is based on the observation that the maximum absorbance of an acid solution of Coomassie brilliant blue g-250 changes from 465 nm to 595 nm when proteins become attached thereto (q.v. Reisner et al., Anal. Biochem., 64, 509 (1975)).

a) Procedure

The following volumes are introduced into the cell of a spectrophotometer set to 595 nm:

10 μl of sample to which 790 μl of distilled water have been added

200 μl of concentrated Dye reagent (Biorad).

The ingredients are mixed and the optical density is read off at 595 nm. A calibration range with increasing concentrations of BSA (bovine serum albumin) was prepared in this way. The unknown concentration of the total proteins in the lyzates is read off on the calibration curve obtained.

b) Results

The main results obtained are collated in Table V below, which specifies the mount (in mg/ml) of total soluble proteins and the percentage of urate oxidase in the total soluble proteins for each strain induced by glycerol-ethanol, each strain induced by glycerol-ethanol-galactose and each non-induced strain (it is assumed here that the specific activity of the recombinant protein is identical to that of the urate oxidase obtained from *A. flavus*: 30 U/mg).

TABLE V

| Strain/Inducer | Total soluble proteins mg/ml | % of urate oxidase in the total soluble proteins |
|---|---|---|
| EMY761/glycerol-ethanol | 5.3 | <0.05 |
| EMY761/glycerol-ethanol-galactose | 5.8 | <0.05 |
| EMY761 pEMR469 (ura+)/non-induced | 8.5 | 0.25 |
| EMY761 pEMR469 (ura+)/glycerol-ethanol | 5.3 | 4.7 |
| EMY761 pEMR469 (leu+)/non-induced | 1.7 | 0.3 |
| EMY761 pEMR469 (leu+)/glycerol-ethanol | 5.9 | 20 |
| EMY761 pEMR473 (ura+)/non-induced | 10.3 | <0.05 |
| EMY761 pEMR473 (ura+)/glycerol-ethanol galactose | 6.5 | 6.4 |
| EMY761 pEMR473 (leu+)/non-induced | 0.5 | <0.05 |
| EMY761 pEMR473 (leu+)/glycerol-ethanol-galactose | 3.9 | 13 |

It is found that the production rate of urate oxidase varies from 5 to 20% according to the transformants and the mode of selection of the transformed strains (leu+).

EXAMPLE 13: Expression, in a 2.5 l fermenter, of urate oxidase cDNA by the EMY761 pEMR473 (ura+) strain 1) Fermentation protocol a) Media
Inoculum medium A colony of the EMY761 pEMR473 (ura+) strain was cultured in 200 ml of uracil-free liquid medium (cf. Table III, Example 11). Culture is continued overnight, with agitation, until the OD is about 3.

| Culture medium A | for 1 l of purified water on an apparatus of the Milli-Q type |
|---|---|
| glucose | 30 g |
| glycerol | 30 g |
| casein hydrolyzate (Casamino acids from DIFCO) | 30 g |
| Yeast Nitrogen Base (from DIFCO) | 15 g |
| Yeast extract (from DIFCO) | 2.5 g |
| K$_2$HPO$_4$ | 3 g |
| MgSO$_4$.7H$_2$O | 0.5 g |

| Additional medium B | for 100 ml of purified water on an apparatus of the Milli-Q type |
|---|---|
| glycerol | 30 g |
| peptone hydrolyzate (Primatone from G. Sheffield) | 30 g |
| Yeast Nitrogen Base (from DIFCO) | 15 g |
| Yeast extract (from DIFCO) | 5 g |
| K$_2$HPO$_4$ | 3 g |
| MgSO$_4$.7H$_2$O | 0.5 g | b) Fermentation parameters
Bioreactor of total volume 2.5 l, equipped with two turbines
Temperature=30° C.
pH=5
Oxygen partial pressure=30 mm Hg
Air flow rate=1 l/min The bioreactor is filled with 1.5 l of medium A and inoculated with 150 ml of the inoculum.

Once the glucose has been exhausted at OD 2.5 to about OD 17, induction is effected by the addition of a volume of 150 ml of galactose at 20% weight/volume. Growth is continued and additional medium B is then added at about OD 30.

Growth continues for about another fifteen hours and the product was harvested at OD 104.

2) Preparation and analysis of the samples

The samples were prepared as described in Example 9 2) a) from the culture in the fermenter. Two samples were taken: the first after 7 h of induction and the second after 22 h of induction.

The following tests, described in Example 9, were performed on these two lyzates obtained after lysis of the cells:
immunodetection by Western blot
assay of the biological activity
assay of the total proteins
The following results were obtained:

a) Immunodetection by Western blot

It is found that the EMY761 pEMR473 (ura+) strain, cultivated in a 2 l fermenter, produces a protein with an apparent molecular weight of 33 kDa, which is recognized by antibodies directed against *A. flavus* urate oxidase (said antibodies being prepared in rabbits by techniques well known to those skilled in the art: q.v. VAITUKAITIS et al. (1981) "Methods in Enzymology", Academic Press, New York, vol. 73, p. 46) and which is absent from the control strain.

b) Assay of the biological activity
The results obtained are collated in Table VI below:

TABLE VI

| Strain/Induction time | U/ml |
|---|---|
| EMY761 pEMR473 (ura+)/7 h | 9 |
| EMY761 pEMR473 (ura+)/22 h | 12.5 |

It is found that the EMY761 pEMR473 (ura+) strain, cultivated in a fermenter, is capable of producing urate oxidase activity after induction.

c) Assay of the total soluble proteins
The results are collated in Table VII below:

TABLE VII

| Strain/Induction time | Total soluble proteins mg/ml | % of urate oxidase in the total soluble proteins |
|---|---|---|
| EMY761 pEMR473 (ura+)/7 h | 5.2 | 5.7 |
| EMY761 pEMR473 (ura+)/21 h | 6.2 | 6.6 |

These results indicate that the rate of synthesis of urate oxidase by the EMY761 pEMR473 (ura+) strain, cultivated in a fermenter, is about 5% of the total proteins of the cell after 7 h and 21 h of induction.

EXAMPLE 14: Expression, in an Erlenmeyer flask, of urate oxidase cDNA by the EMY761 pEMR515 (leu+), EMY500 pEMR515 (leu+) and GRF18 pEMR515 (leu+) strains A colony of each of the above three strains was cultured in 20 ml of leucine-free liquid medium.

After one night at 30° C. with agitation the three cultures were centrifuged for 10 min at 7000 rpm. The cell residues were taken up in 10 ml of sterile distilled water and centrifuged again for 10 min. Expression of the urate oxidase was induced by taking up the cells in 20 ml of ethanol-glycerol-galactose YP medium (cf. Table I, Example 8). The cultures were incubated again at 30° C. for about 20 h, with agitation. The non-transformed host strains were each cultured as controls.

The cells of each of the six cultures are separated out again by centrifugation and the supernatant is removed. The residues were taken up in 10 ml of distilled water and centrifuged for 10 min at 7000 rpm. The residues washed in this way were taken up in about 1 ml of TEA buffer of pH 8.9 and the grinding and removal of the particles by centrifugation were carried out as described in Example 9, 2). The supernatant of each culture is used, as previously, for assaying the urate oxidase and the total proteins. The main results obtained are collated in Table VIII below:

TABLE VIII

| Strain/Culture conditions | Urate oxidase activity (U/ml) | Total soluble proteins (mg/ml) | % of urate oxidase in the soluble proteins |
|---|---|---|---|
| GRF18 pEMR15 (leu+)/a) | <0.1 | 2.2 | <0.05 |
| EMY500 pEMR15 (leu+)/a) | <0.1 | 0.9 | <0.05 |
| EMY761 pEMR515 (leu+)/a) | <0.1 | 1.8 | <0.05 |
| GRF18 pEMR515 (leu+)/b) | 38 | 5.4 | 23 |
| EMY500 pEMR515 (leu+)/b) | 20 | 2.5 | 26 |
| EMY761 pEMR515 (leu+)/b) | 33 | 4.2 | 26 | a): the strains are cultivated in the presence of glucose (non-induction conditions)
b): the strains are cultivated in the absence of glucose and in the presence of galactose (induction)

These results show that a high level of expression of urate oxidase can be obtained with three nonisogenic recipient strains transformed by the expression vector according to the invention.

EXAMPLE 15: Expression in a 2.5 l fermenter of the cDNA of urate oxidase for the EMY500 pEMR515 strain. Purification and partial characterization of the recombinant urate oxidase:

1) Culture in a 2.5 l fermenter of the EMY500 pEMR515 strain:

The culture of the EMY500 pEMR515 strain is carried out in the following manner:

a) Preculture stage in erlenmeyer

A 500 ml erlenmeyer containing 90 ml of a growth medium MCPA, (sterilizable by autoclave) complemented with 1.28 g of MES (2-/N-morpholino/-ethanesulfonic acid: Sigma n° M8250) and 10 ml of a growth medium MCPF (sterilized by ultra filtration) is seeded with 1 ml of a solution of the EMY500 pEMR515 strain in a medium containing 20% glycerol with a number of cells corresponding to an Optical Density of 2.35. The compositions of the media MCPA and MCPF are given hereinafter. After 24 hours of incubation, under stirring at 30° C., the Optical Density of the culture is about 7.

b) Culture phase in fermenter

The above culture is used for seeding a 2.5 l fermenter containing the culture medium having the following composition:

900 ml of MCPA + 200 ml of MCPF

The pH of the culture is regulated by the fermenter to the given value of 5,5. After 6–7 hours of culture at 30° C., 72 ml of a 500 g/l glucose solution is linearly added over a period of 9 hours (namely a total of 36 g of glucose).

c) Expression stage

To the previously described mixture, 100 ml of the expression medium MEPA (sterilizable by autoclave) and 150 ml of the expression medium MEPF (sterilized by ultra filtration) having the following compositions, are added. The culture is then continued for 5 hours. Then 150 ml of a solution containing 30 g of galactose, 15 g of glycerol and 36 g of ethanol are linearly added for 20 hours. An optical density of about 160 is then obtained.

CHEMICAL COMPOSITION OF THE GROWTH AND EXPRESSION MEDIA -
Growth medium MCPA (sterilizable by autoclave)

| | For total 900 ml |
|---|---|
| NTA (nitrilotriacetic acid) | 1.2 g |
| Yeast extract (DIFCO) | 6 g |
| K₂SO₄ | 1.2 g |
| NaCl | 0.6 g |
| MgSO₄, 7H₂O | 1.2 g |
| CaCl₂2H₂O | 840 mg |
| FeCl₃ | 108 mg |
| glutamic acid | 4.44 g |
| HYCASE SF (Sheffield Products) | 30 g |
| leucine | 2.16 g |
| histidine | 600 mg |
| methionine | 1.2 g |
| oligoelements I (see hereinafter) | 5 ml |
| uracil | 1.2 g |

| List of oligoelements I | |
|---|---|
| | for 1 l of ultra purified water |
| CuSO₄, 5H₂O | 780 mg |
| H₃BO₃ | 5 g |
| ZnSO₄, 7H₂O | 3 g |
| KI | 1 g |
| MnSO₄, 2H₂O | 3.5 g |
| Na₂MO₄. 2H₂O | 2 g |
| FeCl₃, 6H₂O | 4.8 g |

Add 100 ml of concentrated hydrochloric acid to the solution and adjust to 1,000 ml.

| Growth medium MCPF (sterilized by ultra filteration) | |
|---|---|
| | for total 200 ml of ultra purified water |
| KH₂PO₄ | 4.8 g |
| Tryptophane | 420 mg |
| Vitamin I (see hereinafter) | 5 ml |
| glucose | 36 g |

Heat to dissolve, return to ambient temperature, add the vitamins I and filter through 0.2 μm filter.

| List of vitamins I | |
|---|---|
| | for total 100 ml of ultra purified water |
| biotine | 1.2 mg |
| folic acid | 1 mg |
| niacine (nicotinic acid) | 144 mg |
| pyridoxine.HCl | 60 mg |

-continued

List of vitamins I

| | for total 100 ml of ultra purified water |
|---|---|
| thiamine.HCl | 240 mg |
| calcium pantothenate | 1.2 g |
| mesoinositol | 2.4 g |

Fill to 100 ml after dissolving
Sterile filter, cold, at 0.2 μm

Expression medium MEPA (sterilizable by autoclave)

| | for total 100 ml of ultra purified water |
|---|---|
| NTA | 1.2 g |
| K2 so4 | 2.08 g |
| glutamic acid | 6 g |
| HYCASE SF (Sheffield Products) | 24 g |
| leucine | 2.16 g |
| histidine | 600 mg |
| methionine | 1.2 g |
| MgSO$_4$, 7H$_2$O | 720 mg |
| CaCl$_2$, 2H$_2$O | 840 mg |
| FeCl$_3$, 6H$_2$O | 108 mg |
| oligoelements I | 5 ml |
| uracil | 1.2 g |

Adjust the pH to 5.5 with concentrated H$_2$SO$_4$ or concentrated KOH
Autoclave for 20 mins at 120° C.

Expression medium MEPF (sterilized by ultra filtration)

| | for total 150 ml of ultra purified water |
|---|---|
| KH$_2$PO$_4$ | 2.4 g |
| tryptophane | 420 mg |
| vitamins I | 5 ml |
| glycerol | 36 g |
| galactose | 45 g |

Heat to dissolve, return to ambient temperature, add the vitamins and filter.

2) Grinding of the cells

After 20 hours of induction, the OD of the culture, measured at 600 nm, is 98. 800 g of the fermentation wort are centrifugated for 5 minutes at 10,000 g and the cell cake is taken up in 80 ml of a lysis buffer (glycine 20 mM pH 8.5). The cells are then ground twice at 4° C., for 2.5 minutes in a grinding device (Vibrogenic Zellmühle mill V14) in the presence of a volume of beads (0.50 mm in diameter) equal to that of the solution of cells to be lysed. After grinding, the supernatant is taken up and the beads are washed twice with 80 ml of a lysis buffer. 210 ml of a lysate are recovered; said lysate has a total protein content of about 3 mg/ml and a urate oxydase activity of about 7.7 U/ml (namely a urate oxidase percentage towards the total protein of about 8.5%, considering a specific activity of that protein of 30 U/mg).

3) Purification of the recombinant urate oxidase a) Purification protocol

The above lysate is submitted to the two-step purification protocol disclosed hereinafter.

Step 1: Anionic chromatography
Support
DEAE (diethylaminosulphate) sepharose fast flow (Pharmacia ref. 17.07.09.91)
The compressed gel occupies a volume of 70 ml.
The separation is carried out at ambient temperature, the recovered fractions being preserved at 0° C.
Separation conditions A gradient of a chloride ionic force between buffer 1 (sodium borate 10 mM, pH 9.2) and buffer 2 (sodium borate 10 mM, sodium chloride 1M) is used. The buffers are previously degased and preserved at O° C. during the elution. In each buffer 0.02% of azide are added.

The raw extract is deposited (10 ml) and eluted with buffer 1 up to the complete recovery of the urate oxidase (by fractions of 10 ml) which is not retained on the column.

The pigments and the contaminating proteins are thereafter removed by an elution with buffer 2.

The purification is followed by measuring of the OD of the eluate at 214 nm.

Step 2: High pressure and inverse phase liquid chromatography
Support
Grafted C8 silica column, Aquapore OD-300 (100×2.1 mm) (Brownlee-Applied Biosystems)
Operating conditions
Eluent 1: ultrapurified water (filtered through a Millipore system) containing 0.1% of trifluoroacetic acid.
Eluent 2: Acetonitrile (of spectrophotometric quality or similar) containing 0.08% of trifluoroacetic acid.
Flow rate: 0.3 ml/min.

The gradient is of 35% of acetonitrile/TFA to 70% of acetonitrile/TFA for 20 minutes and is maintained at 70% for 5 minutes. The injected quantity is of 1 ml per run.

Recovery of the fractions
The separation is followed by measurement of the optical density at 218 nm. The acetonitrile is evaporated during the centrifugation under vacuum.

b) Results

The sample before and after the first step of purification was analysed by liquid chromatography on a grafted C8 silica column, the Aquapore OD-300 previously disclosed with the same gradient, with an injected quantity of 50 μl. Purified urate oxidase from *A flavus* is used as an external control.

In the starting lysate, the urate oxidase represents 63% of the total proteins. After the first step of purification, the urate oxidase represents 84% of the total proteins.

The whole sample obtained after step 2 was used for the following partial characterization. Said sample certainly contains more than 84% of urate oxidase.

4) Partial characterization of the recombinant urate oxidase a) Analysis of the amino acids The analysis of the amino acids of the acid hydrolysate of the purified recombinant urate oxidase was carried out in an analyser from Applied Biosystems model 420-130A. The distribution of the quantified amino acids is compatible (there exists no significant difference) with the supposed sequence. The same result was observed for the purified urate oxidase extracted from *A. flavus* (obtained in example 4)

b) Tryptic peptidic map

A tryptic peptidic map was established for the purified recombinant urate oxidase and for the purified urate oxidase extract obtained in example 4) under the following conditions:

A urate oxidase solution having a concentration of 1 mg/ml is prepared. Extemporaneously a trypsin solution having a concentration of 1 mg/ml is prepared.

The two solutions are mixed together in a proportion of 1/30 enzyme/substrate for 8 hours at ambient temperature. The tryptic hydrolysate is then chromatographied (liquid phase chromatography) on a C18 grafted silica column (5 μm; lichrosorb 250×4.6 mm Hichromref. RP 18-5-250A) provided with a UV detector coupled with a recorder. The gradient applied is of 1% acetonitrile/TFA to 60% acetonitrile/TFA for 120 minutes and then the gradient is maintained at 60% for 5 minutes.

The peptidic maps obtained have a very narrow profile.

5) Determination of the blocked character of the amino-terminal sequence

The amino-terminal sequence was analysed by means of the sequencer, Applied Biosystem model 470A, coupled with an analyser of phenylthiohydantoic derivatives, Applied Biosystems model 120A. The purified recombinant urate oxidase (200 pmoles detected by analysis of the amino acids) was put on the sequencer in the presence of 20 pmoles of β-lactoglobuline (control protein).

No amino-terminal sequence corresponding to the sequence of the urate oxidase was detected, whereas the amino-terminal sequence of the control protein was detected.

Therefore, the recombinant urate oxidase of the invention, as well as the urate oxidase extract, has a blocked amino-terminal end.

EXAMPLE 16: Construction of an expression vector for urate oxidase cDNA in animal cells: plasmid pSV860

This vector was obtained by ligation of the small AccI-SnaBI fragment containing a sequence coding for urate oxidase with the exception of the first 16 amino acids, said fragment being derived from plasmid p466 (an expression vector for *A. flavus* urate oxidase in *E. coli*, available in the laboratory and described below), with a synthetic HindIII-AccI fragment, which made it possible to obtain a HindIII-SnaBI fragment containing a complete sequence coding for *A. flavus* urate oxidase and a non-translated 5' sequence favoring expression in animal cells; and insertion of the HindIII-SnaBI fragment between the HindIII and SnaBI sites of the multiple cloning site (also called polylinker) of the expression vector for animal cells, namely plasmid pSE₁.

The following account will successively describe the construction of plasmid p466, plasmid pSE₁ and plasmid pSV860.

1) Construction of plasmid p466

Plasmid p466, an expression vector for urate oxidase cDNA in *E. coli*, was prepared. It comprises a fragment of pBR327 including the origin of replication and the ampicillin resistance gene; it also comprises a synthetic promoter of *E. coli* (R. RODRIGUEZ and M. CHAMBERLIN, "Promoters-Structure and function (1982), Preager), a Shine-Dalgarno sequence followed by a polylinker containing the unique NdeI and KpnI sites, a transcription terminator (derived from phage fd) and the lac i gene.

This plasmid was constructed from an expression plasmid for hGH in *E. coli* (p462) by replacing a fragment carrying the hGH gene with urate oxidase cDNA.

The construction of plasmid p466 was described in detail in Example 7 above.

2) Construction of an expression vector for animal cells: plasmid pSE₁

The strategy employed uses fragments obtained from pre-existing plasmids available to the public, and fragments prepared synthetically by the techniques now in common use. The cloning techniques employed are those described by T. MANIATIS, E. F. FRITSCH and J. SAMBROOK in "Molecular Cloning, a laboratory manual" (Cold Spring Harbor Laboratory, 1984). The oligonucleotides are synthesized with the aid of a Biosearch 4600 DNA synthesizer.

Figure 13:
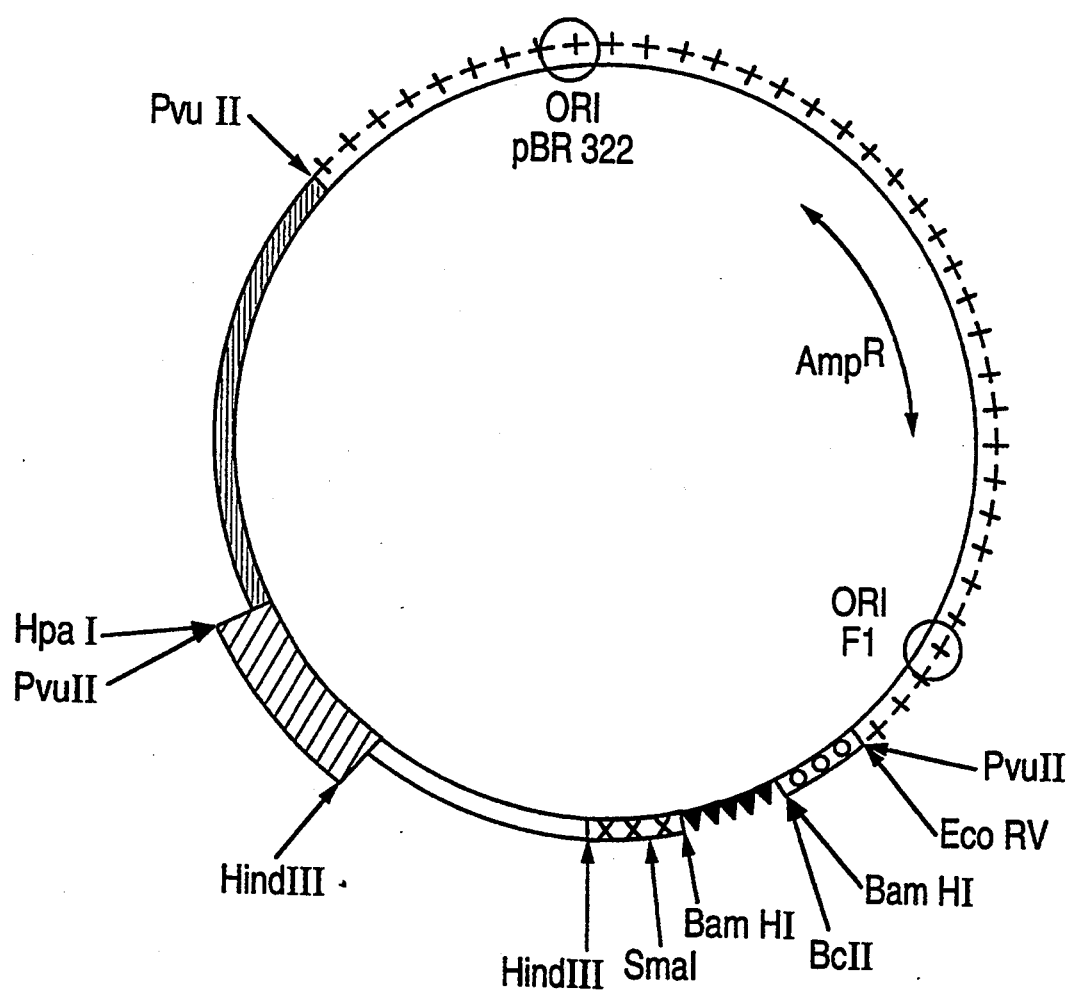
FIG. 13 shows plasmid $PSE_1$.

The following description will be understood more clearly with reference to FIG. 13, which shows a restriction map of plasmid pSE₁, the sites which have disappeared due to ligation being indicated in brackets. The symbols used in this Figure will be specified in the description below.

This plasmid was constructed by successive ligations of the following components:

1)—a PvuII-PvuII fragment—symbolized by +++ in FIG. 13—of 2525 bp, obtained by complete digestion of plasmid pTZ18R (Pharmacia) with the restriction enzyme PvuII. This fragment contains the origin of replication of phage F1 (denoted by ORI F1 in FIG. 13), a gene (denoted by Amp$^R$ in FIG. 13) carrying ampicillin resistance, and the origin of replication (denoted by ORI pBR322 in FIG. 13) permitting the replication of this plasmid in *E. coli*. The first PvuII blunt site disappears on ligation with the EcoRV blunt site (which also disappears) of the fragment described in 7).

2)—a PvuII-HpaI fragment—symbolized by ▅▅▅ in FIG. 13—of 1060 bp, of type 5 adenovirus DNA between position 11299 (PvuII restriction site) and position 10239 (HpaI restriction site) (DEKKER & VAN ORMONDT, Gene 27, 1984, 115-120), containing the information for VA-I and VA-II RNA's. The HpaI blunt site disappears on ligation with the PvuII blunt site (which also disappears) of the fragment described in 3).

3)—a PvuII-HindIII fragment—symbolized by ▨▨▨ in FIG. 13—of 344 bp, derived from SV40 virus DNA and obtained by complete digestion with the restriction enzymes PvuII and HindIII. This fragment contains the origin of replication and the early promoter of SV40 virus DNA (ref. B. J. BYRNE et al., PNAS-USA (1983) 80, 721-725).

The HindIII site disappears on ligation with the site binding to HindIII of the fragment described in 4).

4)—a synthetic "site binding to HindIII"-HindIII fragment—symbolized by ═══ in FIG. 13—of 419 bp, whose sequence, given below (SEQUENCE ID. NO. 33), is similar to the nontranslated 5' sequence of the HTLV1 virus (ref. WEISS et al., "Molecular Biology of Tumor Viruses"-part 2-2nd edition-1985-Cold Spring Harbor Laboratory-p. 1057).

site binding to HindIII
▼

```
      AGCTGGCTCGCATCTCTCCTTCACGCGCCCGCCGCCCTACCTGAGGCCGCCATCCACGCC
  1   ————————+————————+————————+————————+————————+————————+         60
      CCGAGCGTAGAGAGGAAGTGCGCGGGCGGCGGGATGGACTCCGGCGGTAGGTGCGG

GGTGAGTCGCGTTCTGCCGCCTCCCGCCTGTGGTGCCTCCTGAACTGCGTCCGCCGTCTA
 61   ————————+————————+————————+————————+————————+————————+        120
      CCACTCAGCGCAAGACGGCGGAGGGCGGACACCACGGAGGACTTGACGCAGGCGGAGAT

GGTAGGCTCCAAGGGAGCCGGACAAAGGCCCGGTCTCGACCTGAGCTCTAAACTTACCTA
121   ————————+————————+————————+————————+————————+————————+        180
      CCATCCGAGGTTCCCTCGGCCTGTTTCC,GGCCAGAGCTGGACTCGAGATTTGAATGGAT

GACTCAGCCGGCTCTCCACGCTTTGCCTGACCCTGCTTGCTCAACTCTACGTCTTTGTTT
181   ————————+————————+————————+————————+————————+————————+        240
      CTGAGTCGGCCGAGAGGTGCGAAACGGACTGGGACGAACGAGTTGAGATGCAGAAACAAA

CGTTTTCTGTTCTGCGCCGTTACAACTTCAAGGTATGCGCTGGGACCTGGCAGGCGGCAT
241   ————————+————————+————————+————————+————————+————————+        300
      GCAAAAGACAAGACGCGGCAATGTTGAAGTTCCATACGCGACCCTGGACCGTCCGCCGTA

CTGGGACCCCTAGGAAGGGCTTGGGGGTCCTCGTGCCCAAGGCAGGGAACATAGTGGTCC
301   ————————+————————+————————+————————+————————+————————+        360
      GACCCTGGGGATCCTTCCCGAACCCCCAGGAGCACGGGTTCCGTCCCTTGTATCACCAGG

CAGGAAGGGGAGCAGAGGCATCAGGGTGTCCACTTTGTCTCCGCAGCTCCTGAGCCTGCA
361   ————————+————————+————————+————————+————————+————————+        420
      GTCCTTCCCCTCGTCTCCGTAGTCCCACAGGTGAAACAGAGGCGTCGAGGACTCGGACGT

GA
      ——————
      CTTCGA
            ▲
            HindIII
```

5)—a synthetic HindIII-"site binding to BamHI" fragment—symbolized by ✕✕✕✕ in FIG. 13—containing the promoter of the RNA polymerase of phage T7 and also a polylinker containing the SmaI cloning site and having the sequence below (SEQUENCE ID NO. 34).

```
AGCTTGTCGACTAATACGACTCACTATAGGGCGGCCGCGGGCCCCTGCAGGAATTC

ACAGCTGATTATGCTGAGTGATATCCCGCCGGCGCCCGGGGACGTCCTTAAG
     ▲
     HindIII

SmaI              site binding to BamHI
            ▼                         ▼
GGATCCCCCGGGTGACTGACT

CCTAGGGGGCCCACTGACTGACTAG
```

6)—a BamHI-BclI fragment of 240 bp—represented by ▼▼▼▼ in FIG. 13—which is a small fragment obtained by complete digestion of the SV40 virus with the enzymes BclI and BamHI and containing the late polyadenylation site of said virus (M. FITZGERALD et al., Cell, 24, 1981, 251–260). The BamHI and BclI sites disappear on ligation respectively with the site binding to BamHI of the fragment described in 5) and the BamHI site (which also disappears) of the fragment described in 7).

7)—a BamHI-EcoRV fragment—symbolized by ▭▭▭▭ in FIG. 13—of 190 bp, which is a small fragment derived from plasmid pBR322 after complete digestion with the enzymes EcoRV and BamHI.

3) Construction of plasmid pSV860

Plasmid p466 (cf. FIG. 9) was completely digested with the enzymes AccI and SnaBI. The small AccI-SnaBI fragment, which contains a DNA sequence coding for urate oxidase with the exception of the first 16 amino-terminal acids, was purified and ligated with the synthetic HindIII-AccI fragment having the following sequence (SEQUENCE ID NO. 35):

```
  HindIII                                                          AccI
    ▼                                                               ▼
    AGCTTGCCGCCACTATGTCCGCAGTAAAAGCAGCCCGCTACGGCAAGGACAATGTCCGCGT
    ————————+————————+————————+————————+————————+————————+
         ACGGCGGTGATACAGGCGTCATTTTCGTCGGGCGATGCCGTTCCTGTTACAGGCGCAGA
```

This ligation makes it possible to obtain the HindIII-SnaBI fragment containing a sequence, coding for urate oxidase, which is identical to that of clone 9C and a non-translated 5' sequence favoring expression in animal cells (KOZAK, M., Nucl. Acids Res., 12, 2, 1984, 857–872).

The HindIII-SnaBI fragment contains the following sequence (SEQUENCE ID NO. 36):

| | | | | |
|---|---|---|---|---|
| 5'-AGCTTGCCG | CCACTATGTC | CGCAGTAAAA | GCAGCCCGCT | ACGGCAAGGA |
| CAATGTCCGC | GTCTACAAGG | TTCACAAGGA | CGAGAAGACC | GGTGTCCAGA |
| CGGTGTACGA | GATGACCGTC | TGTGTGCTTC | TGGAGGGTGA | GATTGAGACC |
| TCTTACACCA | AGGCCGACAA | CAGCGTCATT | GTCGCAACCG | ACTCCATTAA |
| GAACACCATT | TACATCACCG | CCAAGCAGAA | CCCCGTTACT | CCTCCCGAGC |
| TGTTCGGCTC | CATCCTGGGC | ACACACTTCA | TTGAGAAGTA | CAACCACATC |
| CATGCCGCTC | ACGTCAACAT | TGTCTGCCAC | CGCTGGACCC | GGATGGACAT |
| TGACGGCAAG | CCACACCCTC | ACTCCTTCAT | CCGCGACAGC | GAGGAGAAGC |
| GGAATGTGCA | GGTGGACGTG | GTCGAGGGCA | AGGGCATCGA | TATCAAGTCG |
| TCTCTGTCCG | GCCTGACCGT | GCTGAAGAGC | ACCAACTCGC | AGTTCTGGGG |
| CTTCCTGCGT | GACGAGTACA | CCACACTTAA | GGAGACCTGG | GACCGTATCC |
| TGAGCACCGA | CGTCGATGCC | ACTTGGCAGT | GGAAGAATTT | CAGTGGACTC |
| CAGGAGGTCC | GCTCGCACGT | GCCTAAGTTC | GATGCTACCT | GGGCCACTGC |
| TCGCGAGGTC | ACTCTGAAGA | CTTTTGCTGA | AGATAACAGT | GCCAGCGTGC |
| AGGCCACTAT | GTACAAGATG | GCAGAGCAAA | TCCTGGCGCG | CCAGCAGCTG |
| ATCGAGACTG | TCGAGTACTC | GTTGCCTAAC | AAGCACTATT | TCGAAATCGA |
| CCTGAGCTGG | CACAAGGGCC | TCCAAAACAC | CGGCAAGAAC | GCCGAGGTCT |
| TCGCTCCTCA | GTCGGACCCC | AACGGTCTGA | TCAAGTGTAC | CGTCGGCCGG |
| TCCTCTCTGA | AGTCTAAATT | G | | |

Figure 14:
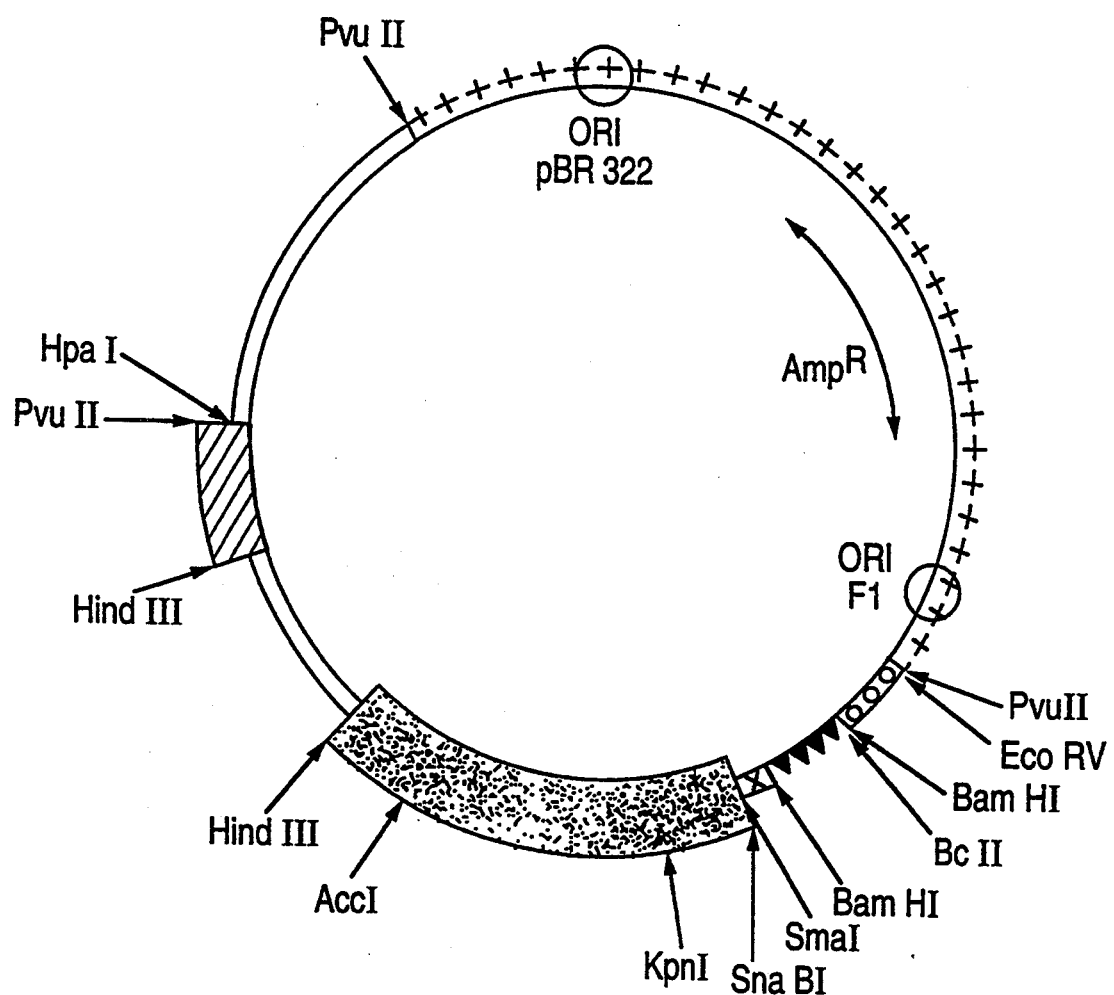
FIG. 14 shows plasmid pSV860.

The HindIII-SnaBI fragment was then inserted into vector pSE₁, which had first been incubated with the enzymes HindIII and SmaI. This gave plasmid pSV860 shown in FIG. 14, in which the symbols have the same meanings as in FIG. 13, the novel HindIII-SnaBI fragment being symbolized by ▒▒▒▒. (The SnaBI and SmaI sites disappeared on ligation.)

EXAMPLE 17: Transient expression of urate oxidase cDNA in COS cells-Assay of the urate oxidase activity in the cell lyzate COS cells are monkey kidney cells expressing the T-antigen of the SV40 virus (Gluzman, Y., Cell 23, 1981, 175-182). These cells, which permit the replication of vectors containing the origin of replication of SV40 virus DNA, are preferred hosts for studying the expression of genes in animal cells.

1) Transfection of COS cells and transient expression of urate oxidase cDNA $4.10^5$ COS cells are plated out in a Petri dish of diameter 6 cm (Corning) in 5 ml of Dulbecco's modified Eagle's medium (from Gibco), hereafter called DMEM, which contains 0.6 g/l of glutamine and 3.7 g/l of $NaHCO_3$ and is complemented with fetal calf serum (GIBCO) at a rate of 5%. After about 16 h of culture at 37° C. in an atmosphere containing 5% of carbon dioxide, the culture medium is sucked off and the cells are washed with 3 ml of PBS (phosphate buffered saline from GIBCO). The following mixture is then added: 1000 μl of (DMEM+10% of fetal calf serum (GIBCO)), 110 μl of diethylaminoethyldextran of average molecular weight 500,000 at a concentration of 2 mg/ml (Pharmacia), 1.1 μl of chloroquine 100 mM (Sigma) and 3 μg of DNA of either plasmid pSV860 or plasmid pSE₁ (for the control). After incubation for 5 h at 37° C. in an atmosphere containing 5% of carbon dioxide, the mixture is withdrawn from the cells. 2 ml of PBS containing 10% of dimethyl sulfoxide (spectroscopic grade, Merck) are then added. After incubation for 1 min at room temperature, the mixture is withdrawn and the cells are washed twice with PBS. 5 ml of DMEM complemented with fetal calf serum at a rate of 2% are added. Incubation is continued for 4 days at 37° C. under an atmosphere containing 5% of carbon dioxide.

2) Preparation of the samples

The culture medium is sucked off and the COS cells are rinsed twice with 3 ml of PBS. The cells are then collected by scratching with a rubber spatula (policeman) in 1 ml of PBS. After scratching, the dish is rinsed with 1 ml of PBS. The two cell suspensions are combined and centrifuged for 10 min at 1000 rpm. The supernatant is removed and the cell residue is resuspended in 1 ml of triethylammonium (TEA) 0.05M of pH 8.9/EDTA buffer.

The cells are lyzed by sonication (on ice) by means of 10 s pulses with a sonicator (Vibra Cell from Sonics and Materials Inc. USA) set to a power of 12 W. The cell lyzate is centrifuged for 10 min at 10,000 rpm and the supernatant is recovered for assay of the urate oxidase.

3) Assay of the urate oxidase activity

The urate oxidase activity was assayed as described in Example 9.

The results are collated in the Table below:

| COS cells transfected by | Urate oxidase activity U/ml |
|---|---|
| pSVS60 | 0.105 |
| pSE₁ | <0.01 |

It is found that the COS cells transfected by plasmid pSV860 carrying urate oxidase cDNA express an appreciable level of urate oxidase activity, whereas no urate oxidase activity is detectable in the control. There is therefore expression of urate oxidase cDNA.

SEQUENCE LISTING ( 1 ) GENERAL INFORMATION:

( i i i ) NUMBER OF SEQUENCES: 36

( 2 ) INFORMATION FOR SEQ ID NO:1:

(  i  ) SEQUENCE CHARACTERISTICS:
    (  A  ) LENGTH: 301 amino acids
    (  B  ) TYPE: amino acid
    (  D  ) TOPOLOGY: linear (  i i  ) MOLECULE TYPE: protein (  i i i  ) HYPOTHETICAL: NO (  v i  ) ORIGINAL SOURCE:
    (  A  ) ORGANISM: Aspergillus flavus (  v i i  ) IMMEDIATE SOURCE:
    (  B  ) CLONE: Urate oxidase (  x i  ) SEQUENCE DESCRIPTION: SEQ ID NO:1:

```
Ser Ala Val Lys Ala Ala Arg Tyr Gly Lys Asp Asn Val Arg Val Tyr
  1               5                  10                  15
Lys Val His Lys Asp Glu Lys Thr Gly Val Gln Thr Val Tyr Glu Met
             20                  25                  30
Thr Val Cys Val Leu Leu Glu Gly Glu Ile Glu Thr Ser Tyr Thr Lys
         35                  40                  45
Ala Asp Asn Ser Val Ile Val Ala Thr Asp Ser Ile Lys Asn Thr Ile
     50                  55                  60
Tyr Ile Thr Ala Lys Gln Asn Pro Val Thr Pro Pro Glu Leu Phe Gly
 65                  70                  75                  80
Ser Ile Leu Gly Thr His Phe Ile Glu Lys Tyr Asn His Ile His Ala
                 85                  90                  95
Ala His Val Asn Ile Val Cys His Arg Trp Thr Arg Met Asp Ile Asp
             100                 105                 110
Gly Lys Pro His Pro His Ser Phe Ile Arg Asp Ser Glu Glu Lys Arg
         115                 120                 125
Asn Val Gln Val Asp Val Val Glu Gly Lys Gly Ile Asp Ile Lys Ser
     130                 135                 140
Ser Leu Ser Gly Leu Thr Val Leu Lys Ser Thr Asn Ser Gln Phe Trp
145                 150                 155                 160
Gly Phe Leu Arg Asp Glu Tyr Thr Thr Leu Lys Glu Thr Trp Asp Arg
                 165                 170                 175
Ile Leu Ser Thr Asp Val Asp Ala Thr Trp Gln Trp Lys Asn Phe Ser
             180                 185                 190
Gly Leu Gln Glu Val Arg Ser His Val Pro Lys Phe Asp Ala Thr Trp
         195                 200                 205
Ala Thr Ala Arg Glu Val Thr Leu Lys Thr Phe Ala Glu Asp Asn Ser
     210                 215                 220
Ala Ser Val Gln Ala Thr Met Tyr Lys Met Ala Gln Gln Ile Leu Ala
225                 230                 235                 240
Arg Gln Gln Leu Ile Glu Thr Val Glu Tyr Ser Leu Pro Asn Lys His
                 245                 250                 255
Tyr Phe Glu Ile Asp Leu Ser Trp His Lys Gly Leu Gln Asn Thr Gly
             260                 265                 270
Lys Asn Ala Glu Val Phe Ala Pro Gln Ser Asp Pro Asn Gly Leu Ile
         275                 280                 285
Lys Cys Thr Val Gly Arg Ser Ser Leu Lys Ser Lys Leu
         290                 295                 300
```

(  2  ) INFORMATION FOR SEQ ID NO:2:

(  i  ) SEQUENCE CHARACTERISTICS:
    (  A  ) LENGTH: 302 amino acids
    (  B  ) TYPE: amino acid
    (  C  ) STRANDEDNESS: single
    (  D  ) TOPOLOGY: linear (ii) MOLECULE TYPE: protein (iii) HYPOTHETICAL: NO (vi) ORIGINAL SOURCE:
    (A) ORGANISM: Aspergillus flavus (vii) IMMEDIATE SOURCE:
    (B) CLONE: Met-Urate oxidase (xi) SEQUENCE DESCRIPTION: SEQ ID NO:2:

```
Met Ser Ala Val Lys Ala Ala Arg Tyr Gly Lys Asp Asn Val Arg Val
 1               5                  10                 15
Tyr Lys Val His Lys Asp Glu Lys Thr Gly Val Gln Thr Val Tyr Glu
                20                  25                 30
Met Thr Val Cys Val Leu Leu Glu Gly Glu Ile Glu Thr Ser Tyr Thr
            35                  40                 45
Lys Ala Asp Asn Ser Val Ile Val Ala Thr Asp Ser Ile Lys Asn Thr
    50                  55                  60
Ile Tyr Ile Thr Ala Lys Gln Asn Pro Val Thr Pro Pro Glu Leu Phe
65                  70                  75                  80
Gly Ser Ile Leu Gly Thr His Phe Ile Glu Lys Tyr Asn His Ile His
                85                  90                  95
Ala Ala His Val Asn Ile Val Cys His Arg Trp Thr Arg Met Asp Ile
            100                 105                110
Asp Gly Lys Pro His Pro His Ser Phe Ile Arg Asp Ser Glu Glu Lys
            115                 120                125
Arg Asn Val Gln Val Asp Val Val Glu Gly Lys Gly Ile Asp Ile Lys
    130                 135                 140
Ser Ser Leu Ser Gly Leu Thr Val Leu Lys Ser Thr Asn Ser Gln Phe
145                 150                 155                 160
Trp Gly Phe Leu Arg Asp Glu Tyr Thr Thr Leu Lys Glu Thr Trp Asp
                165                 170                 175
Arg Ile Leu Ser Thr Asp Val Asp Ala Thr Trp Gln Trp Lys Asn Phe
            180                 185                 190
Ser Gly Leu Gln Glu Val Arg Ser His Val Pro Lys Phe Asp Ala Thr
            195                 200                 205
Trp Ala Thr Ala Arg Glu Val Thr Leu Lys Thr Phe Ala Glu Asp Asn
    210                 215                 220
Ser Ala Ser Val Gln Ala Thr Met Tyr Lys Met Ala Glu Gln Ile Leu
225                 230                 235                 240
Ala Arg Gln Gln Leu Ile Glu Thr Val Glu Tyr Ser Leu Pro Asn Lys
                245                 250                 255
His Tyr Phe Glu Ile Asp Leu Ser Trp His Lys Gly Leu Gln Asn Thr
            260                 265                 270
Gly Lys Asn Ala Glu Val Phe Ala Pro Gln Ser Asp Pro Asn Gly Leu
        275                 280                 285
Ile Lys Cys Thr Val Gly Arg Ser Ser Leu Lys Ser Lys Leu
    290                 295                 300
```

(2) INFORMATION FOR SEQ ID NO:3:

(i) SEQUENCE CHARACTERISTICS:
        (A) LENGTH: 906 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:

(B) CLONE: Preferred sequence for expression in prokaryotes (xi) SEQUENCE DESCRIPTION: SEQ ID NO:3:

| | | | | | |
|---|---|---|---|---|---|
| ATGTCTGCGG | TAAAAGCAGC | GCGCTACGGC | AAGGACAATG | TTCGCGTCTA | CAAGGTTCAC | 60 |
| AAGGACGAGA | AGACCGGTGT | CCAGACGGTG | TACGAGATGA | CCGTCTGTGT | GCTTCTGGAG | 120 |
| GGTGAGATTG | AGACCTCTTA | CACCAAGGCC | GACAACAGCG | TCATTGTCGC | AACCGACTCC | 180 |
| ATTAAGAACA | CCATTTACAT | CACCGCCAAG | CAGAACCCCG | TTACTCCTCC | CGAGCTGTTC | 240 |
| GGCTCCATCC | TGGGCACACA | CTTCATTGAG | AAGTACAACC | ACATCCATGC | CGCTCACGTC | 300 |
| AACATTGTCT | GCCACCGCTG | GACCCGGATG | GACATTGACG | GCAAGCCACA | CCCTCACTCC | 360 |
| TTCATCCGCG | ACAGCGAGGA | GAAGCGGAAT | GTGCAGGTGG | ACGTGGTCGA | GGGCAAGGGC | 420 |
| ATCGATATCA | AGTCGTCTCT | GTCCGGCCTG | ACCGTGCTGA | AGAGCACCAA | CTCGCAGTTC | 480 |
| TGGGGCTTCC | TGCGTGACGA | GTACACCACA | CTTAAGGAGA | CCTGGGACCG | TATCCTGAGC | 540 |
| ACCGACGTCG | ATGCCACTTG | GCAGTGGAAG | AATTTCAGTG | GACTCCAGGA | GGTCCGCTCG | 600 |
| CACGTGCCTA | AGTTCGATGC | TACCTGGGCC | ACTGCTCGCG | AGGTCACTCT | GAAGACTTTT | 660 |
| GCTGAAGATA | ACAGTGCCAG | CGTGCAGGCC | ACTATGTACA | AGATGGCAGA | GCAAATCCTG | 720 |
| GCGCGCCAGC | AGCTGATCGA | GACTGTCGAG | TACTCGTTGC | CTAACAAGCA | CTATTTCGAA | 780 |
| ATCGACCTGA | GCTGGCACAA | GGGCCTCCAA | AACACCGGCA | AGAACGCCGA | GGTCTTCGCT | 840 |
| CCTCAGTCGG | ACCCCAACGG | TCTGATCAAG | TGTACCGTCG | GCCGGTCCTC | TCTGAAGTCT | 900 |
| AAATTG | | | | | | 906 |

(2) INFORMATION FOR SEQ ID NO:4:

(i) SEQUENCE CHARACTERISTICS:
(A) LENGTH: 906 base pairs
(B) TYPE: nucleic acid
(C) STRANDEDNESS: single
(D) TOPOLOGY: linear (ii) MOLECULE TYPE: DNA (genomic)

(vii) IMMEDIATE SOURCE:
(B) CLONE: Preferred sequence for expression in eukaryotes (xi) SEQUENCE DESCRIPTION: SEQ ID NO:4:

| | | | | | |
|---|---|---|---|---|---|
| ATGTCTGCTG | TTAAGGCTGC | TAGATACGGT | AAGGACAACG | TTAGAGTCTA | CAAGGTTCAC | 60 |
| AAGGACGAGA | AGACCGGTGT | CCAGACGGTG | TACGAGATGA | CCGTCTGTGT | GCTTCTGGAG | 120 |
| GGTGAGATTG | AGACCTCTTA | CACCAAGGCC | GACAACAGCG | TCATTGTCGC | AACCGACTCC | 180 |
| ATTAAGAACA | CCATTTACAT | CACCGCCAAG | CAGAACCCCG | TTACTCCTCC | CGAGCTGTTC | 240 |
| GGCTCCATCC | TGGGCACACA | CTTCATTGAG | AAGTACAACC | ACATCCATGC | CGCTCACGTC | 300 |
| AACATTGTCT | GCCACCGCTG | GACCCGGATG | GACATTGACG | GCAAGCCACA | CCCTCACTCC | 360 |
| TTCATCCGCG | ACAGCGAGGA | GAAGCGGAAT | GTGCAGGTGG | ACGTGGTCGA | GGGCAAGGGC | 420 |
| ATCGATATCA | AGTCGTCTCT | GTCCGGCCTG | ACCGTGCTGA | AGAGCACCAA | CTCGCAGTTC | 480 |
| TGGGGCTTCC | TGCGTGACGA | GTACACCACA | CTTAAGGAGA | CCTGGGACCG | TATCCTGAGC | 540 |
| ACCGACGTCG | ATGCCACTTG | GCAGTGGAAG | AATTTCAGTG | GACTCCAGGA | GGTCCGCTCG | 600 |
| CACGTGCCTA | AGTTCGATGC | TACCTGGGCC | ACTGCTCGCG | AGGTCACTCT | GAAGACTTTT | 660 |
| GCTGAAGATA | ACAGTGCCAG | CGTGCAGGCC | ACTATGTACA | AGATGGCAGA | GCAAATCCTG | 720 |
| GCGCGCCAGC | AGCTGATCGA | GACTGTCGAG | TACTCGTTGC | CTAACAAGCA | CTATTTCGAA | 780 |
| ATCGACCTGA | GCTGGCACAA | GGGCCTCCAA | AACACCGGCA | AGAACGCCGA | GGTCTTCGCT | 840 |

| CCTCAGTCGG | ACCCCAACGG | TCTGATCAAG | TGTACCGTCG | GCCGGTCCTC | TCTGAAGTCT | 900 |
| AAATTG | | | | | | 906 |

( 2 ) INFORMATION FOR SEQ ID NO:5:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i i ) IMMEDIATE SOURCE:
        ( B ) CLONE: Preferred non-translated 5'sequence for
            animal cells ( x i ) SEQUENCE DESCRIPTION: SEQ ID NO:5:

| AGCTTGCCGC | CACT | 14 |

( 2 ) INFORMATION FOR SEQ ID NO:6:

( i ) SEQUENCE CHARACTERISTICS:
        ( A ) LENGTH: 906 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i i ) IMMEDIATE SOURCE:
        ( B ) CLONE: Preferred sequence for expression in animal
            cells ( x i ) SEQUENCE DESCRIPTION: SEQ ID NO:6:

| ATGTCCGCAG | TAAAAGCAGC | CCGCTACGGC | AAGGACAATG | TCCGCGTCTA | CAAGGTTCAC | 60 |
| AAGGACGAGA | AGACCGGTGT | CCAGACGGTG | TACGAGATGA | CCGTCTGTGT | GCTTCTGGAG | 120 |
| GGTGAGATTG | AGACCTCTTA | CACCAAGGCC | GACAACAGCG | TCATTGTCGC | AACCGACTCC | 180 |
| ATTAAGAACA | CCATTTACAT | CACCGCCAAG | CAGAACCCCG | TTACTCCTCC | CGAGCTGTTC | 240 |
| GGCTCCATCC | TGGGCACACA | CTTCATTGAG | AAGTACAACC | ACATCCATGC | CGCTCACGTC | 300 |
| AACATTGTCT | GCCACCGCTG | GACCCGGATG | GACATTGACG | GCAAGCCACA | CCCTCACTCC | 360 |
| TTCATCCGCG | ACAGCGAGGA | GAAGCGGAAT | GTGCAGGTGG | ACGTGGTCGA | GGGCAAGGGC | 420 |
| ATCGATATCA | AGTCGTCTCT | GTCCGGCCTG | ACCGTGCTGA | AGAGCACCAA | CTCGCAGTTC | 480 |
| TGGGGCTTCC | TGCGTGACGA | GTACACCACA | CTTAAGGAGA | CCTGGGACCG | TATCCTGAGC | 540 |
| ACCGACGTCG | ATGCCACTTG | GCAGTGGAAG | AATTTCAGTG | GACTCCAGGA | GGTCCGCTCG | 600 |
| CACGTGCCTA | AGTTCGATGC | TACCTGGGCC | ACTGCTCGCG | AGGTCACTCT | GAAGACTTTT | 660 |
| GCTGAAGATA | ACAGTGCCAG | CGTGCAGGCC | ACTATGTACA | AGATGGCAGA | GCAAATCCTG | 720 |
| GCGCGCCAGC | AGCTGATCGA | GACTGTCGAG | TACTCGTTGC | CTAACAAGCA | CTATTTCGAA | 780 |
| ATCGACCTGA | GCTGGCACAA | GGGCCTCCAA | AACACCGGCA | AGAACGCCGA | GGTCTTCGCT | 840 |
| CCTCAGTCGG | ACCCCAACGG | TCTGATCAAG | TGTACCGTCG | GCCGGTCCTC | TCTGAAGTCT | 900 |
| AAATTG | | | | | | 906 |

( 2 ) INFORMATION FOR SEQ ID NO:7:

( i ) SEQUENCE CHARACTERISTICS:
        ( A ) LENGTH: 23 base pairs
        ( B ) TYPE: nucleic acid (C) STRANDEDNESS: single
(D) TOPOLOGY: linear (i i) MOLECULE TYPE: DNA (genomic)

(i i i) HYPOTHETICAL: NO (v i i) IMMEDIATE SOURCE:
    (B) CLONE: reverse transcription primer (x i) SEQUENCE DESCRIPTION: SEQ ID NO:7:

GATCCGGGCC CTTTTTTTT TTT                                                                           23

(2) INFORMATION FOR SEQ ID NO:8:

(i) SEQUENCE CHARACTERISTICS:
        (A) LENGTH: 10 amino acids
        (B) TYPE: amino acid
        (C) STRANDEDNESS: single
        (D) TOPOLOGY: linear (i i) MOLECULE TYPE: peptide (i i i) HYPOTHETICAL: NO (v i i) IMMEDIATE SOURCE:
        (B) CLONE: Hydrolysis product T 17

(x i) SEQUENCE DESCRIPTION: SEQ ID NO:8:

Asn Val Gln Val Asp Val Val Glu Gly Lys
1               5                   10

(2) INFORMATION FOR SEQ ID NO:9:

(i) SEQUENCE CHARACTERISTICS:
        (A) LENGTH: 8 amino acids
        (B) TYPE: amino acid
        (C) STRANDEDNESS: single
        (D) TOPOLOGY: linear (i i) MOLECULE TYPE: peptide (i i i) HYPOTHETICAL: NO (v i i) IMMEDIATE SOURCE:
        (B) CLONE: Hydrolysis product T 20

(x i) SEQUENCE DESCRIPTION: SEQ ID NO:9:

Asn Phe Ser Gly Leu Gln Glu Val
1               5

(2) INFORMATION FOR SEQ ID NO:10:

(i) SEQUENCE CHARACTERISTICS:
        (A) LENGTH: 6 amino acids
        (B) TYPE: amino acid
        (C) STRANDEDNESS: single
        (D) TOPOLOGY: linear (i i) MOLECULE TYPE: peptide (i i i) HYPOTHETICAL: NO (v i i) IMMEDIATE SOURCE:
        (B) CLONE: Hydrolysis product T 23

(x i) SEQUENCE DESCRIPTION: SEQ ID NO:10:

Phe Asp Ala Thr Trp Ala
1               5

(2) INFORMATION FOR SEQ ID NO:11:

(i) SEQUENCE CHARACTERISTICS:
        (A) LENGTH: 8 amino acids

-continued (B) TYPE: amino acid
   (C) STRANDEDNESS: single
   (D) TOPOLOGY: linear (ii) MOLECULE TYPE: peptide (iii) HYPOTHETICAL: NO (vii) IMMEDIATE SOURCE:
   (B) CLONE: Hydrolysis product T 27

(xi) SEQUENCE DESCRIPTION: SEQ ID NO:11:

```
His  Tyr  Phe  Glu  Ile  Asp  Leu  Ser
 1                    5
```

(2) INFORMATION FOR SEQ ID NO:12:

(i) SEQUENCE CHARACTERISTICS:
   (A) LENGTH: 13 amino acids
   (B) TYPE: amino acid
   (C) STRANDEDNESS: single
   (D) TOPOLOGY: linear (ii) MOLECULE TYPE: peptide (iii) HYPOTHETICAL: NO (vii) IMMEDIATE SOURCE:
   (B) CLONE: Hydrolysis product T 28

(xi) SEQUENCE DESCRIPTION: SEQ ID NO:12:

```
Ile  Leu  Ser  Thr  Asp  Val  Asp  Ala  Thr  Trp  Gln  Trp  Lys
 1                    5                              10
```

(2) INFORMATION FOR SEQ ID NO:13:

(i) SEQUENCE CHARACTERISTICS:
   (A) LENGTH: 11 amino acids
   (B) TYPE: amino acid
   (C) STRANDEDNESS: single
   (D) TOPOLOGY: linear (ii) MOLECULE TYPE: peptide (iii) HYPOTHETICAL: NO (vii) IMMEDIATE SOURCE:
   (B) CLONE: Hydrolysis product T 29

(xi) SEQUENCE DESCRIPTION: SEQ ID NO:13:

```
His  Tyr  Phe  Glu  Ile  Asp  Leu  Ser  Trp  His  Lys
 1                    5                        10
```

(2) INFORMATION FOR SEQ ID NO:14:

(i) SEQUENCE CHARACTERISTICS:
   (A) LENGTH: 11 amino acids
   (B) TYPE: amino acid
   (C) STRANDEDNESS: single
   (D) TOPOLOGY: linear (ii) MOLECULE TYPE: peptide (iii) HYPOTHETICAL: NO (vii) IMMEDIATE SOURCE:
   (B) CLONE: Hydrolysis product T 31

(xi) SEQUENCE DESCRIPTION: SEQ ID NO:14:

```
Ser  Thr  Asn  Ser  Gln  Phe  Trp  Gly  Phe  Leu  Arg
 1                    5                        10
```

(2) INFORMATION FOR SEQ ID NO:15:

( i ) SEQUENCE CHARACTERISTICS:
 ( A ) LENGTH: 16 amino acids
 ( B ) TYPE: amino acid
 ( C ) STRANDEDNESS: single
 ( D ) TOPOLOGY: linear ( i i ) MOLECULE TYPE: peptide ( i i i ) HYPOTHETICAL: NO ( v i i ) IMMEDIATE SOURCE:
 ( B ) CLONE: Hydrolysis product T 32

( x i ) SEQUENCE DESCRIPTION: SEQ ID NO:15:

```
Gln Asn Pro Val Thr Pro Pro Glu Leu Phe Gly Ser Ile Leu Gly Thr
 1               5                  10                  15
```

( 2 ) INFORMATION FOR SEQ ID NO:16:

( i ) SEQUENCE CHARACTERISTICS:
  ( A ) LENGTH: 16 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( v i i ) IMMEDIATE SOURCE:
  ( B ) CLONE: Hydrolysis product T 33

( x i ) SEQUENCE DESCRIPTION: SEQ ID NO:16:

```
Gln Asn Pro Val Thr Pro Pro Glu Leu Phe Gly Ser Ile Leu Gly Thr
 1               5                  10                  15
```

( 2 ) INFORMATION FOR SEQ ID NO:17:

( i ) SEQUENCE CHARACTERISTICS:
  ( A ) LENGTH: 17 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( v i i ) IMMEDIATE SOURCE:
  ( B ) CLONE: Hydrolysis product V 1

( x i ) SEQUENCE DESCRIPTION: SEQ ID NO:17:

```
Tyr Ser Leu Pro Asn Lys His Tyr Phe Glu Ile Asp Leu Ser Trp His
 1               5                  10                  15
Lys
```

( 2 ) INFORMATION FOR SEQ ID NO:18:

( i ) SEQUENCE CHARACTERISTICS:
  ( A ) LENGTH: 16 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( v i i ) IMMEDIATE SOURCE:
  ( B ) CLONE: Hydrolysis product V 2

( x i ) SEQUENCE DESCRIPTION: SEQ ID NO:18:

```
Val Thr Leu Lys Thr Phe Ala Glu Asp Asn Ser Ala Ser Val Gln Ala
 1               5                  10                  15
```

( 2 ) INFORMATION FOR SEQ ID NO:19:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v i i ) IMMEDIATE SOURCE:
        ( B ) CLONE: Hydrolysis product V 3

( x i ) SEQUENCE DESCRIPTION: SEQ ID NO:19:

```
Thr Ser Tyr Thr Lys Ala Asp Asn Ser Val Ile Val Asp Thr Asp Ser
 1               5                  10                 15

Ile Lys Asn Thr Ile Tyr Ile Thr
             20
```

( 2 ) INFORMATION FOR SEQ ID NO:20:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v i i ) IMMEDIATE SOURCE:
        ( B ) CLONE: Hydrolysis product V 5

( x i ) SEQUENCE DESCRIPTION: SEQ ID NO:20:

```
Gly Lys Gly Ile Asp Ile Lys Ser Ser Leu Ser Gly Leu Thr Val Leu
 1               5                  10                 15

Lys Ser Thr Asn Ser Gln Phe Trp Gly Phe Leu Arg
             20                  25
```

( 2 ) INFORMATION FOR SEQ ID NO:21:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v i i ) IMMEDIATE SOURCE:
        ( B ) CLONE: Hydolysis product V 6

( x i ) SEQUENCE DESCRIPTION: SEQ ID NO:21:

```
Gly Lys Gly Ile Asp Ile Lys Ser Ser Leu Ser Gly Leu Thr Val Leu
 1               5                  10                 15

Lys
```

( 2 ) INFORMATION FOR SEQ ID NO:22:

( i ) SEQUENCE CHARACTERISTICS:
        ( A ) LENGTH: 1236 base pairs
        ( B ) TYPE: nucleic acid
        ( C ) STRANDEDNESS: single
        ( D ) TOPOLOGY: linear ( i i ) MOLECULE TYPE: DNA (genomic)

(iii) HYPOTHETICAL: NO (vii) IMMEDIATE SOURCE:
    (B) CLONE: Fragment 3

(xi) SEQUENCE DESCRIPTION: SEQ ID NO:22:

| | | | | | |
|---|---|---|---|---|---|
| GATCCGCGGA | AGCATAAAGT | GTAAAGCCTG | GGGTGCCTAA | TGAGTGAGCT | AACTTACATT | 60
| AATTGCGTTG | CGCTCACTGC | CCGCTTTCCA | GTCGGGAAAC | CTGTCGTGCC | AGCTGCATTA | 120
| ATGAATCGGC | CAACGCGCGG | GGAGAGGCGG | TTTGCGTATT | GGGCGCCAGG | GTGGTTTTTC | 180
| TTTTCACCAG | TGAGACGGGC | AACAGCTGAT | TGCCCTTCAC | CGCCTGGCCC | TGAGAGAGTT | 240
| GCAGCAAGCG | GTCCACGCTG | GTTTGCCCCA | CCACCCGAAA | ATCCTGTTTG | ATGGTGGTTA | 300
| ACGGCGGGAT | ATAACATGAG | CTGTCTTCGG | TATCGTCGTA | TCCCACTACC | GAGATATCCG | 360
| CACCAACGCG | CAGCCCGGAC | TCGGTAATGG | CGCGCATTGC | GCCCAGCGCC | ATCTGATCGT | 420
| TGGCAACCAG | CATCGCAGTG | GAACGATGC | CCTCATTCAG | CATTTGCATG | GTTTGTTGAA | 480
| AACCGGACAT | GGCACTCCAG | TCGCCTTCCC | GTTCCGCTAT | CGGCTGAATT | TGATTGCGAG | 540
| TGAGATATTT | ATGCCAGCCA | GCCAGACGCA | GACGCGCCGA | GACAGAACTT | AATGGGCCCG | 600
| CTAACAGCGC | GATTTGCTGG | TGACCCAATG | CGACCAGATG | CTCCACGCCC | AGTCGCGTAC | 660
| CGTCTTCATG | GGAGAAAATA | ATACTGTTGA | TGGGTGTCTG | GTCAGAGACA | TCAAGAAATA | 720
| ACGCCGGAAC | ATTAGTGCAG | GCAGCTTCCA | CAGCAATGGC | ATCCTGGTCA | TCCAGCGGAT | 780
| AGTTAATGAT | CAGCCCACTG | ACGCGTTGCG | CGAGAAGATT | GTGCACCGCC | GCTTTACAGG | 840
| CTTCGACGCC | GCTTCGTTCT | ACCATCGACA | CCACCACGCT | GGCACCCAGT | TGATCGGCGC | 900
| GAGATTTAAT | CGCCGCGACA | ATTTGCGACG | GCGCGTGCAG | GGCCAGACTG | GAGGTGGCAA | 960
| CGCCAATCAG | CAACGACTGT | TTGCCCGCCA | GTTGTTGTGC | CACGCGGTTG | GAATGTAAT | 1020
| TCAGCTCCGC | CATCGCCGCT | TCCACTTTTT | CCCGCGTTTT | CGCAGAAACG | TGGCTGGCCT | 1080
| GGTTCACCAC | GCGGGAAACG | GTCTGATAAC | AGACACCGGC | ATACTCTGCG | ACATCGTATA | 1140
| ACGTTACTGG | TTTCACATTC | ACCACCCTGA | ATTGACTCTC | TTCCGGGCGC | TATCATGCCA | 1200
| TACCGCGAAA | GGTTTTGCGC | CATTCGATGG | TGTCCG | | | 1236

(2) INFORMATION FOR SEQ ID NO:23:

(i) SEQUENCE CHARACTERISTICS:
        (A) LENGTH: 321 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vii) IMMEDIATE SOURCE:
        (B) CLONE: Fragment 4

(ix) FEATURE:
        (A) NAME/KEY: CDS
        (B) LOCATION: 107..316
        (D) OTHER INFORMATION: /product="regulatory signal aa
            1-44 human growth hormone precursor"

(xi) SEQUENCE DESCRIPTION: SEQ ID NO:23:

| | | | | | |
|---|---|---|---|---|---|
| TCGAGCTGAC | TGACCTGTTG | CTTATATTAC | ATCGATAGCG | TATAATGTGT | GGAATTGTGA | 60
| GCGATAACAA | TTTCACACAG | TTTAACTTTA | AGAAGGAGAT | ATACAT ATG GCT ACC | | 115

Met Ala Thr
                                                                 1

GGA TCC CGG ACT AGT CTG CTC CTG GCT TTT GGC CTG CTC TGC CTG CCC    163

|  | Gly | Ser | Arg | Thr | Ser | Leu | Leu | Leu | Ala | Phe | Gly | Leu | Leu | Cys | Leu | Pro |  |
|---|---|---|---|---|---|---|---|---|---|---|---|---|---|---|---|---|---|
|  |  | 5 |  |  |  |  | 10 |  |  |  |  | 15 |  |  |  |  |  |
| TGG | CTT | CAA | GAG | GGC | AGT | GCC | TTC | CCA | ACC | ATT | CCC | TTA | TCT | AGA | CTT |  | 211 |
| Trp | Leu | Gln | Glu | Gly | Ser | Ala | Phe | Pro | Thr | Ile | Pro | Leu | Ser | Arg | Leu |  |  |
| 20 |  |  |  |  | 25 |  |  |  |  | 30 |  |  |  |  | 35 |  |  |
| TTT | GAC | AAC | GCT | ATG | CTC | CGC | GCC | CAT | CGT | CTG | CAC | CAG | CTG | GCC | TTT |  | 259 |
| Phe | Asp | Asn | Ala | Met | Leu | Arg | Ala | His | Arg | Leu | His | Gln | Leu | Ala | Phe |  |  |
|  |  |  |  | 40 |  |  |  |  | 45 |  |  |  |  | 50 |  |  |  |
| GAC | ACC | TAC | CAG | GAG | TTT | GAA | GAA | GCC | TAT | ATC | CCA | AAG | GAA | CAG | AAG |  | 307 |
| Asp | Thr | Tyr | Gln | Glu | Phe | Glu | Glu | Ala | Tyr | Ile | Pro | Lys | Glu | Gln | Lys |  |  |
|  |  |  | 55 |  |  |  |  | 60 |  |  |  |  | 65 |  |  |  |  |
| TAT | TCA | TTC | CTGCA |  |  |  |  |  |  |  |  |  |  |  |  |  | 321 |
| Tyr | Ser | Phe |  |  |  |  |  |  |  |  |  |  |  |  |  |  |  |
|  |  | 70 |  |  |  |  |  |  |  |  |  |  |  |  |  |  |  |

( 2 ) INFORMATION FOR SEQ ID NO:24:

( i ) SEQUENCE CHARACTERISTICS:
        ( A ) LENGTH: 70 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

| Met | Ala | Thr | Gly | Ser | Arg | Thr | Ser | Leu | Leu | Leu | Ala | Phe | Gly | Leu | Leu |
|---|---|---|---|---|---|---|---|---|---|---|---|---|---|---|---|
| 1 |  |  |  | 5 |  |  |  |  | 10 |  |  |  |  | 15 |  |
| Cys | Leu | Pro | Trp | Leu | Gln | Glu | Gly | Ser | Ala | Phe | Pro | Thr | Ile | Pro | Leu |
|  |  | 20 |  |  |  |  | 25 |  |  |  |  | 30 |  |  |  |
| Ser | Arg | Leu | Phe | Asp | Asn | Ala | Met | Leu | Arg | Ala | His | Arg | Leu | His | Gln |
|  |  | 35 |  |  |  |  | 40 |  |  |  |  | 45 |  |  |  |
| Leu | Ala | Phe | Asp | Thr | Tyr | Gln | Glu | Phe | Glu | Glu | Ala | Tyr | Ile | Pro | Lys |
|  | 50 |  |  |  |  | 55 |  |  |  |  | 60 |  |  |  |  |
| Glu | Gln | Lys | Tyr | Ser | Phe |  |  |  |  |  |  |  |  |  |  |
| 65 |  |  |  |  | 70 |  |  |  |  |  |  |  |  |  |  |

( 2 ) INFORMATION FOR SEQ ID NO:25:

( i ) SEQUENCE CHARACTERISTICS:
        ( A ) LENGTH: 74 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i i ) IMMEDIATE SOURCE:
        ( B ) CLONE: ClaI-NdeI fragment ( x i ) SEQUENCE DESCRIPTION: SEQ ID NO:25:

CGATAGCGTA TAATGTGTGG AATTGTGAGC GGATAACAAT TTCACACAGT TTTTCGCGAA    60

GAAGGAGATA TACA    74

( 2 ) INFORMATION FOR SEQ ID NO:26:

( i ) SEQUENCE CHARACTERISTICS:
        ( A ) LENGTH: 190 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i i ) IMMEDIATE SOURCE:

(B) CLONE: Plasmid p373,2 fragment (xi) SEQUENCE DESCRIPTION: SEQ ID NO:26:

| GATCTTCAAG | CAGACCTACA | GCAAGTTCGA | CACAAACTCA | CACAACGATG | ACGCACTACT | 60 |
| CAAGAACTAC | GGGCTGCTCT | ACTGCTTCAG | GAAGGACATG | GACAAGGTCG | AGACATTCCT | 120 |
| GCGCATCGTG | CAGTGCCGCT | CTGTGGAGGG | CAGCTGTGGC | TTCTAGTAAG | GTACCCTGCC | 180 |
| CTACGTACCA | | | | | | 190 |

(2) INFORMATION FOR SEQ ID NO:27:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vii) IMMEDIATE SOURCE:
        (B) CLONE: AccI-NdeI synthetic fragment (xi) SEQUENCE DESCRIPTION: SEQ ID NO:27:

| TATGTCTGCG | GTAAAAGCAG | CGCGCTACGG | CAAGGACAAT | GTTCGCGT | 48 |

(2) INFORMATION FOR SEQ ID NO:28:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vii) IMMEDIATE SOURCE:
        (B) CLONE: Plasmid pEMR469 fragment (xi) SEQUENCE DESCRIPTION: SEQ ID NO:28:

| GGGACGCGTC | TCCTCTGCCG | GAACACCGGG | CATCTCCAAC | TTATAAGTTG | GAGAAATAAG | 60 |
| AGAATTTCAG | ATTGAGAGAA | TGAAAAAAAA | AAAAAAAAA | AAGGCAGAGG | AGAGCATAGA | 120 |
| AATGGGGTTC | ACTTTTTGGT | AAAGCTATAG | CATGCCTATC | ACATATAAAT | AGAGTGCCAG | 180 |
| TAGCGACTTT | TTTCACACTC | GAGATACTCT | TACTACTGCT | CTCTTGTTGT | TTTTATCACT | 240 |
| TCTTGTTTCT | TCTTGGTAAA | TAGAATATCA | AGCTACAAAA | AGCATACAAT | CAACTATCAA | 300 |
| CTATTAACTA | TATCGATACC | ATATGGATCC | GTCGACTCTA | GAGGATCGTC | GACTCTAGAG | 360 |

(2) INFORMATION FOR SEQ ID NO:29:

(i) SEQUENCE CHARACTERISTICS:
        (A) LENGTH: 58 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vii) IMMEDIATE SOURCE:
        (B) CLONE: Fragment C (xi) SEQUENCE DESCRIPTION: SEQ ID NO:29:

| CGATATACAC | AATGTCTGCT | GTTAAGGCTG | CTAGATACGG | TAAGGACAAC | GTTAGAGT | 58 |

( 2 ) INFORMATION FOR SEQ ID NO:30:

( i ) SEQUENCE CHARACTERISTICS:
        ( A ) LENGTH: 1013 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i i ) IMMEDIATE SOURCE:
        ( B ) CLONE: Fragment D ( x i ) SEQUENCE DESCRIPTION: SEQ ID NO:30:

```
CTACAAGGTT CACAAGGACG AGAAGACCGG TGTCCAGACG GTGTACGAGA TGACCGTCTG      60
TGTGCTTCTG GAGGGTGAGA TTGAGACCTC TTACACCAAG GCCGACAACA GCGTCATTGT     120
CGCAACCGAC TCCATTAAGA ACACCATTTA CATCACCGCC AAGCAGAACC CCGTTACTCC     180
TCCCGAGCTG TTCGGCTCCA TCCTGGGCAC ACACTTCATT GAGAAGTACA CCACATCCA      240
TGCCGCTCAC GTCAACATTG TCTGCCACCG CTGGACCCGG ATGGACATTG ACGGCAAGCC     300
ACACCCTCAC TCCTTCATCC GCGACAGCGA GGAGAAGCGG AATGTGCAGG TGGACGTGGT     360
CGAGGGCAAG GGCATCGATA TCAAGTCGTC TCTGTCCGGC CTGACCGTGC TGAAGAGCAC     420
CAACTCGCAG TTCTGGGGCT TCCTGCGTGA CGAGTACACC ACACTTAAGG AGACCTGGGA     480
CCGTATCCTG AGCACCGACG TCGATGCCAC TTGGCAGTGG AAGAATTTCA GTGGACTCCA     540
GGAGGTCCGC TCGCACGTGC CTAAGTTCGA TGCTACCTGG GCCACTGCTC GCGAGGTCAC     600
TCTGAAGACT TTTGCTGAAG ATAACAGTGC CAGCGTGCAG GCCACTATGT ACAAGATGGC     660
AGAGCAAATC CTGGCGCGCC AGCAGCTGAT CGAGACTGTC GAGTACTCGT TGCCTAACAA     720
GCACTATTTC GAAATCGACC TGAGCTGGCA CAAGGGCCTC CAAAACACCG GCAAGAACGC     780
CGAGGTCTTC GCTCCTCAGT CGGACCCCAA CGGTCTGATC AAGTGTACCG TCGGCCGGTC     840
CTCTCTGAAG TCTAAATTGT AAACCAACAT GATTCTCACG TTCCGGAGTT TCCAAGGCAA     900
ACTGTATATA GTCTGGGATA GGGTATAGCA TTCATTCACT TGTTTTTTAC TTCCAAAAAA     960
AAAAAAAAAA AAAAAAAAAA AAAAAAAAAA AAAAAAAAAA AAAAAGGGC CCG            1013
```

( 2 ) INFORMATION FOR SEQ ID NO:31:

( i ) SEQUENCE CHARACTERISTICS:
        ( A ) LENGTH: 207 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i i ) IMMEDIATE SOURCE:
        ( B ) CLONE: Synthetic GAL7 fragment ( x i ) SEQUENCE DESCRIPTION: SEQ ID NO:31:

```
CGCGTCTATA CTTCGGAGCA CTGTTGAGCG AAGGCTCATT AGATATATTT TCTGTCATTT      60
TCCTTAACCC AAAAATAAGG GAGAGGGTCC AAAAAGCGCT CGGACAACTG TTGACCGTGA     120
TCCGAAGGAC TGGCTATACA GTGTTCACAA AATAGCCAAG CTGAAAATAA TGTGTAGCCT     180
TTAGCTATGT TCAGTTAGTT TGGCATG                                         207
```

( 2 ) INFORMATION FOR SEQ ID NO:32:

( i ) SEQUENCE CHARACTERISTICS:

(A) LENGTH: 23 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vii) IMMEDIATE SOURCE:
(B) CLONE: Modified XbaI-MluI adapter (xi) SEQUENCE DESCRIPTION: SEQ ID NO:32:

```
CTAGGCTAGC GGGCCCGCAT GCA                                              23
```

(2) INFORMATION FOR SEQ ID NO:33:

(i) SEQUENCE CHARACTERISTICS:
(A) LENGTH: 422 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vii) IMMEDIATE SOURCE:
(B) CLONE: Plasmid pSE1 "site binding to HindIII"
fragment (xi) SEQUENCE DESCRIPTION: SEQ ID NO:33:

```
AGCTGGCTCG CATCTCTCCT TCACGCGCCC GCCGCCCTAC CTGAGGCCGC CATCCACGCC      60
GGTGAGTCGC GTTCTGCCGC CTCCCGCCTG TGGTGCCTCC TGAACTGCGT CCGCCGTCTA     120
GGTAGGCTCC AAGGGAGCCG GACAAAGGCC CGGTCTCGAC CTGAGCTCTA AACTTACCTA     180
GACTCAGCCG GCTCTCCACG CTTTGCCTGA CCCTGCTTGC TCAACTCTAC GTCTTTGTTT     240
CGTTTTCTGT TCTGCGCCGT TACAACTTCA AGGTATGCGC TGGGACCTGG CAGGCGGCAT     300
CTGGGACCCC TAGGAAGGGC TTGGGGGTCC TCGTGCCCAA GGCAGGGAAC ATAGTGGTCC     360
CAGGAAGGGG AGCAGAGGCA TCAGGGTGTC CACTTTGTCT CCGCAGCTCC TGAGCCTGCA     420
GA                                                                   422
```

(2) INFORMATION FOR SEQ ID NO:34:

(i) SEQUENCE CHARACTERISTICS:
(A) LENGTH: 77 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (vii) IMMEDIATE SOURCE:
(B) CLONE: Synthetic HindIII-"site binding to BamHI"
fragment (xi) SEQUENCE DESCRIPTION: SEQ ID NO:34:

```
AGCTTGTCGA CTAATACGAC TCACTATAGG GCGGCCGCGG GCCCCTGCAG GAATTCGGAT      60
CCCCGGGTG ACTGACT                                                      77
```

(2) INFORMATION FOR SEQ ID NO:35:

(i) SEQUENCE CHARACTERISTICS:
(A) LENGTH: 61 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (vii) IMMEDIATE SOURCE:
(B) CLONE: Synthetic HindIII-AccI fragment (xi) SEQUENCE DESCRIPTION: SEQ ID NO:35:

| | | | | | |
|---|---|---|---|---|---|
| AGCTTGCCGC | CACTATGTCC | GCAGTAAAAG | CAGCCCGCTA | CGGCAAGGAC | AATGTCCGCG | 60 |
| T | | | | | | 61 |

(2) INFORMATION FOR SEQ ID NO:36:

(i) SEQUENCE CHARACTERISTICS:
(A) LENGTH: 920 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vii) IMMEDIATE SOURCE:
(B) CLONE: HindIII-SnaBI fragment (xi) SEQUENCE DESCRIPTION: SEQ ID NO:36:

| | | | | | | |
|---|---|---|---|---|---|---|
| AGCTTGCCGC | CACTATGTCC | GCAGTAAAAG | CAGCCCGCTA | CGGCAAGGAC | AATGTCCGCG | 60 |
| TCTACAAGGT | TCACAAGGAC | GAGAAGACCG | GTGTCCAGAC | GGTGTACGAG | ATGACCGTCT | 120 |
| GTGTGCTTCT | GGAGGGTGAG | ATTGAGACCT | CTTACACCAA | GGCCGACAAC | AGCGTCATTG | 180 |
| TCGCAACCGA | CTCCATTAAG | AACACCATTT | ACATCACCGC | CAAGCAGAAC | CCCGTTACTC | 240 |
| CTCCCGAGCT | GTTCGGCTCC | ATCCTGGGCA | CACACTTCAT | TGAGAAGTAC | AACCACATCC | 300 |
| ATGCCGCTCA | CGTCAACATT | GTCTGCCACC | GCTGGACCCG | GATGGACATT | GACGGCAAGC | 360 |
| CACACCCTCA | CTCCTTCATC | CGCGACAGCG | AGGAGAAGCG | GAATGTGCAG | GTGGACGTGG | 420 |
| TCGAGGGCAA | GGGCATCGAT | ATCAAGTCGT | CTCTGTCCGG | CCTGACCGTG | CTGAAGAGCA | 480 |
| CCAACTCGCA | GTTCTGGGGC | TTCCTGCGTG | ACGAGTACAC | CACACTTAAG | GAGACCTGGG | 540 |
| ACCGTATCCT | GAGCACCGAC | GTCGATGCCA | CTTGGCAGTG | GAAGAATTTC | AGTGGACTCC | 600 |
| AGGAGGTCCG | CTCGCACGTG | CCTAAGTTCG | ATGCTACCTG | GGCCACTGCT | CGCGAGGTCA | 660 |
| CTCTGAAGAC | TTTTGCTGAA | GATAACAGTG | CCAGCGTGCA | GGCCACTATG | TACAAGATGG | 720 |
| CAGAGCAAAT | CCTGGCGCGC | CAGCAGCTGA | TCGAGACTGT | CGAGTACTCG | TTGCCTAACA | 780 |
| AGCACTATTT | CGAAATCGAC | CTGAGCTGGC | ACAAGGGCCT | CCAAAACACC | GGCAAGAACG | 840 |
| CCGAGGTCTT | CGCTCCTCAG | TCGGACCCCA | ACGGTCTGAT | CAAGTGTACC | GTCGGCCGGT | 900 |
| CCTCTCTGAA | GTCTAAATTG | | | | | 920 |

What is claimed is:

1. A protein possessing a specific urate oxidase activity of at least 16 U/mg and having the following sequence (SEQ ID NO:1):

| Ser | Ala | Val | Lys | Ala | Ala | Arg | Tyr | Gly | Lys |
|---|---|---|---|---|---|---|---|---|---|
| Asp | Asn | Val | Arg | Val | Tyr | Lys | Val | His | Lys |
| Asp | Glu | Lys | Thr | Gly | Val | Gln | Thr | Val | Tyr |
| Glu | Met | Thr | Val | Cys | Val | Leu | Leu | Glu | Gly |
| Glu | Ile | Glu | Thr | Ser | Tyr | Thr | Lys | Ala | Asp |
| Asn | Ser | Val | Ile | Val | Ala | Thr | Asp | Ser | Ile |
| Lys | Asn | Thr | Ile | Tyr | Ile | Thr | Ala | Lys | Gln |
| Asn | Pro | Val | Thr | Pro | Pro | Glu | Leu | Phe | Gly |
| Ser | Ile | Leu | Gly | Thr | His | Phe | Ile | Glu | Lys |
| Tyr | Asn | His | Ile | His | Ala | Ala | His | Val | Asn |
| Ile | Val | Cys | His | Arg | Trp | Thr | Arg | Met | Asp |
| Ile | Asp | Gly | Lys | Pro | His | Pro | His | Ser | Phe |
| Ile | Arg | Asp | Ser | Glu | Glu | Lys | Arg | Asn | Val |
| Gln | Val | Asp | Val | Val | Glu | Gly | Lys | Gly | Ile |
| Asp | Ile | Lys | Ser | Ser | Leu | Ser | Gly | Leu | Thr |
| Val | Leu | Lys | Ser | Thr | Asn | Ser | Gln | Phe | Trp |
| Gly | Phe | Leu | Arg | Asp | Glu | Tyr | Thr | Thr | Leu |
| Lys | Glu | Thr | Trp | Asp | Arg | Ile | Leu | Ser | Thr |
| Asp | Val | Asp | Ala | Thr | Trp | Gln | Trp | Lys | Asn |
| Phe | Ser | Gly | Leu | Gln | Glu | Val | Arg | Ser | His |
| Val | Pro | Lys | Phe | Asp | Ala | Thr | Trp | Ala | Thr |
| Ala | Arg | Glu | Val | Thr | Leu | Lys | Thr | Phe | Ala |
| Glu | Asp | Asn | Ser | Ala | Ser | Val | Gln | Ala | Thr |
| Met | Tyr | Lys | Met | Ala | Glu | Gln | Ile | Leu | Ala |
| Arg | Gln | Gln | Leu | Ile | Glu | Thr | Val | Glu | Tyr |

-continued

| Ser | Leu | Pro | Asn | Lys | His | Tyr | Phe | Glu | Ile |
| Asp | Leu | Ser | Trp | His | Lys | Gly | Leu | Gln | Asn |
| Thr | Gly | Lys | Asn | Ala | Glu | Val | Phe | Ala | Pro |
| Gln | Ser | Asp | Pro | Asn | Gly | Leu | Ile | Lys | Cys |
| Thr | Val | Gly | Arg | Ser | Ser | Leu | Lys | Ser | Lys |
| Leu | | | | | | | | | | preceded, if appropriate, by a methionine.

2. A protein according to claim 1, wherein said protein is produced by recombinant methods.

3. A protein according to claim 1, which represents, by analysis on a bidimensional Laemmli/SDS-Agarose gel, a spot of molecular mass of about 33.5 kDa, representing at least 90% of the protein mass.

4. A protein according to claim 1, having a purity degree, determined by liquid chromatography on a C8 grafted silica column, higher than 80%.

5. A protein according to claim 1, having an isoelectric point around 8.0.

6. A protein according to claim 1, which carries a blocking group on the amino-terminal serine.

7. A pharmaceutical composition comprising a protein according to claim 1.

8. A protein according to claim 6, wherein said blocking group is an acetyl group.

9. A protein according to claim 2, possessing a specific urate oxidase activity of about 30 U/mg.

* * * * *

UNITED STATES PATENT AND TRADEMARK OFFICE

(12)          CERTIFICATE EXTENDING PATENT TERM
UNDER 35 U.S.C. § 156

(68) PATENT NO. : 5,382,518

(45) ISSUED : January 17, 1995

(75) INVENTOR : Daniel Caput, et al.

(73) PATENT OWNER : Sanofi-Adventis

(95) PRODUCT : ELITEK® (rasburicase)

This is to certify that an application under 35 U.S.C. § 156 has been filed in the United States Patent and Trademark Office, requesting extension of the term of U.S. Patent No. 5,382,518 based upon the regulatory review of the product ELITEK® (rasburicase) by the Food and Drug Administration. Since it appears that the requirements of the law have been met, this certificate extends the term of the patent for the period of

(94)          1,638 days from January 17, 2012, the original expiration date of the patent, subject to the payment of maintenance fees as provided by law, with all rights pertaining thereto as provided by 35 U.S.C. § 156(b).

I have caused the seal of the United States Patent and Trademark Office to be affixed this 12th day of October 2005.

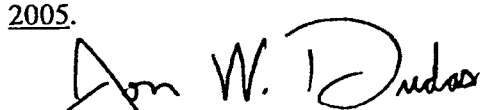

Jon W. Dudas
Under Secretary of Commerce for Intellectual Property and Director of the United States Patent and Trademark Office

UNITED STATES PATENT AND TRADEMARK OFFICE

(12)  CERTIFICATE EXTENDING PATENT TERM
UNDER 35 U.S.C. § 156

| | | | |
|---|---|---|---|
| (68) | PATENT NO. | : | 5,382,518 |
| (45) | ISSUED | : | January 17, 1995 |
| (75) | INVENTOR | : | Daniel Caput, et al. |
| (73) | PATENT OWNER | : | Sanofi-Adventis |
| (95) | PRODUCT | : | ELITEK® (rasburicase) |

This is to certify that an application under 35 U.S.C. § 156 has been filed in the United States Patent and Trademark Office, requesting extension of the term of U.S. Patent No. 5,382,518 based upon the regulatory review of the product ELITEK® (rasburicase) by the Food and Drug Administration. Since it appears that the requirements of the law have been met, this certificate extends the term of the patent for the period of

(94)  1,638 days from January 17, 2012, the original expiration date of the patent, subject to the payment of maintenance fees as provided by law, with all rights pertaining thereto as provided by 35 U.S.C. § 156(b).

I have caused the seal of the United States Patent and Trademark Office to be affixed this 12th day of October 2005.

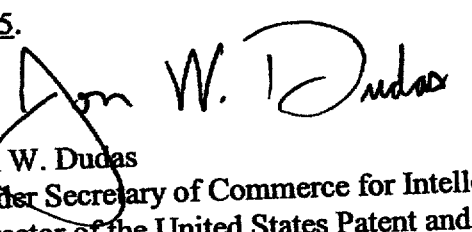

Jon W. Dudas
Under Secretary of Commerce for Intellectual Property and
Director of the United States Patent and Trademark Office